United States Patent
Fox et al.

(10) Patent No.: US 8,945,902 B2
(45) Date of Patent: Feb. 3, 2015

(54) COMBINATORIAL DISCOVERY OF ENZYMES WITH UTILITY IN BIOMASS TRANSFORMATION

(75) Inventors: Brian G. Fox, Madison, WI (US); Nathaniel L. Elsen, Chalfont, PA (US)

(73) Assignee: Wisconsin Alumni Research Foundation, Madison, WI (US)

(*) Notice: Subject to any disclaimer, the term of this patent is extended or adjusted under 35 U.S.C. 154(b) by 318 days.

(21) Appl. No.: 12/792,156

(22) Filed: Jun. 2, 2010

(65) Prior Publication Data

US 2010/0304405 A1 Dec. 2, 2010

Related U.S. Application Data

(60) Provisional application No. 61/183,243, filed on Jun. 2, 2009.

(51) Int. Cl.
  *C12N 9/42* (2006.01)
  *C12N 15/82* (2006.01)
  *C12N 15/10* (2006.01)

(52) U.S. Cl.
  CPC ........ *C12N 15/8261* (2013.01); *C12N 15/1079* (2013.01)
  USPC ....................................... 435/209

(58) Field of Classification Search
  None
  See application file for complete search history.

(56) References Cited

U.S. PATENT DOCUMENTS

| 8,043,839 | B2 | 10/2011 | Weiner et al. |
| 2006/0105442 | A1 | 5/2006 | Wu et al. |

FOREIGN PATENT DOCUMENTS

| WO | 02/079403 A2 | 10/2002 |
| WO | 2004/096999 A2 | 11/2004 |
| WO | 2007/139608 A1 | 12/2007 |

OTHER PUBLICATIONS

Arias et al., J. Bacteriol. 285 (2):504-512, 2003.*
Zverlov et al., FEMS Microbiology Letters, 249, 353-358, 2005.*
Haimovitz, R. et al., "Cohesin-dockerin Microarray: Diverse specificities between two complementary families of interacting protein modules" 2008 Proteomics 8: 968-979.
Fierobe, H.P. et al., "Controlled Incorporation of Three Distinct Enzymes into a Defined Trifunctional Scaffoldin" 2005 J. Biol. Chem. 280: 16325-16334.
Heyman, et al., "Multiple display of catalytic modules on a protein scaffold: Nano Fabrication of enzyme particles" 2007 Journal of Biotechnology 131: 433-439.
Hughes, Stephen R., et al., "High-throughput screening of cellulose F mutants from multiplexed plasmid sets using an automated plate assay on a functional proteomic robotic workcell," Proteome Science, Biomed Central, London, Great Britain, DOI:10.1186/1477-5956-4-10; vol. 4, No. 1, May 2, 2006, pp. 1-14.
International Searching Authority, "PCT International Search Report," International application No. PCT/US2010/037094, European Patent Office, Jan. 13, 2011, pp. 1-8.

* cited by examiner

*Primary Examiner* — Nancy T Vogel
(74) *Attorney, Agent, or Firm* — Quarles & Brady LLP

(57) ABSTRACT

Methods for the cell-free identification of polypeptide and polypeptide combinations with utility in biomass transformation, as well as specific novel polypeptides and cell-free systems containing polypeptide combinations discovered by such methods are disclosed.

3 Claims, 24 Drawing Sheets scaffoldins 80 kDa 42 kDa 39 kDa 58 kDa

COMBINATORIAL DISCOVERY OF ENZYMES WITH UTILITY IN BIOMASS TRANSFORMATION

CROSS-REFERENCE TO RELATED APPLICATIONS

This application claims the benefit of U.S. Provisional Patent Application No. 61/183,243, filed on Jun. 2, 2009, which is incorporated by reference herein in its entirety.

STATEMENT CONCERNING FEDERALLY SPONSORED RESEARCH OR DEVELOPMENT

This invention was made with United States government support awarded by the Department of Energy, DOE grant No. DE-FC02-07ER64494. The United States government has certain rights in this invention.

FIELD OF THE INVENTION

This invention is related to the biochemical arts, and is directed to expression systems and methods for combinatorial discovery of enzymes with utility in biomass transformation, such as the transformation of biomass into solubilized organic material.

BACKGROUND OF THE INVENTION

The biofuels industry uses biomass, primarily from plants, to produce soluble sugars that are subsequently fermented to create fuels such as ethanol, butanol, adipate, methylfuran, isoprenes, and biodiesel for human use. The complex structure of biomass, particularly the diversity of cellulosic structures that make up a large portion of plant materials, make the efficient and economical deconstruction of biomass into soluble sugars a difficult challenge for the industry.

Currently, biomass may be chemically pretreated to facilitate the partial decomposition of biomass structure. Specifically, chemical treatment allows for more complete contact of enzymes or microbes to the biomass structure. Chemicals used for such treatments may include acids, steam, ionic liquids, alkaline hydrogen peroxide, or high pressure liquid ammonia (AFEX).

After any chemical pretreatment, the biomass undergoes enzymatic hydrolysis to produce solubilized sugars suitable for fermentation. Because of the complex structure of biomass, many different enzymes are necessary for complete biomass deconstruction, including cellulases, glycohydrolases, xylanases, and xylobiosidases, mannases and mannosidases, arabinofuranosidases, lichinases, esterases, pectinases, and other enzyme types. Enzymes used in biomass deconstruction exist naturally in bacteria and other organisms, and researchers are currently engaged in extensive enzyme discovery efforts to characterize and isolate previously unknown enzymes that may prove useful in biomass deconstruction.

In nature, many approaches have evolved for the enzymatic deconstruction of cellulose. One class of natural cellulolytic enzymes are freely diffusible enzymes that bind to cellulose only in the sense that an enzyme active site will recognize the substrate and bind to a specific arrangement of chemical bonds in order to perform catalysis, the hydrolytic cleavage of the glycosidic bond.

A second class of natural cellulolytic enzymes bind to cellulose through carbohydrate binding domains, cellulose binding domains, cellulose binding modules, or other binding domains on the enzyme surface. The binding domains facilitate the attachment of the enzyme to the cellulose to effect the deconstruction of cellulose. Such enzymes are not attached to the cell, and must exist outside of the cell to have function.

A third class of natural cellulolytic enzymes also interact with cellulose to effect its deconstruction, but are additionally bound to a bacterial cell wall. Such enzymes are found on the outer surface of bacterial cells.

A fourth class of natural cellulolytic enzymes include cellulolytic, hemicellulolytic, pectinolytic, and/or esterolytic enzymes that are assembled into multiprotein complexes called cellulosomes, which are complexes of enzymes created by bacteria such as *Clostridium* and *Bacteroides*. Cellulosomes assemble and function outside of the bacterial cells that create the component enzymes. The cellulosomal enzymes are attached to a large, multimodular, noncatalytic subunit called scaffoldin. Scaffoldin has domains known as cohesins, which interact with other domains called dockerins. Cohesins integrate dockerin-tagged enzymes into the cellulosome complex. Scaffoldin and some cellulosomal enzymes also contain carbohydrate binding domains, cellulose binding domains, cellulose binding modules, or other binding domains which bind to cellulose, hemicellulose, starch, pectin, chitin or other polysaccharide structures.

Cellulosome architecture is the consequence of the types and specificities of the interacting cohesin and dockerin domains, borne by the different cellulosomal subunits (Haimovitz et al., 2008, *Proteomics* 8: 968-979), and is further affected by the presence of carbohydrate binding domains. It has been shown that it is possible to create designer chimeric cellulosomes through the modification of cohesin and dockerin domains (Fierobe et al., 2005, *J. Biol. Chem.* 280: 16325-16334). It has also been shown that artificial scaffoldin proteins can be created to accomplish the function of the scaffoldin while not relying on the domain structure or order of the natural scaffoldin to achieve this function.

As illustrated by the great diversity cellulolytic enzymes, many combinations of enzymes and proteins are involved in natural cellulose deconstruction. Further evidence of the great complexity and diversity of possible cellulose degradation pathways is provided by the genomic sequencing of microbes and fungi, and by bioinformatic analysis of the metagenomic sequences isolated from all organisms present in a natural environment. For example, recent whole genome sequencing studies of *Streptomyces* sp. ActE isolated from the Sirex wood wasp revealed 127 separate genes that are plausibly involved in the breakdown of carbohydrates (C. Currie, et al., *Streptomyces* sp. ACTE, whole genome shotgun sequencing project, NCBI. Reference Sequence: NZ_A-DFD00000000.1). In another recent study assaying gene expression during growth on cellulose in *C. thermocellum* ATCC 27405 using controlled growth rate microarrays, 348 of the organism's 3191 genes were expressed, and 34 of the expressed genes had uncharacterized export signals (Riederer, Takasuka, Makino, Stevenson, Bukhman, Fox, unpublished work).

The complexity of biomass deconstruction as a biological problem makes conventional single enzyme assays inadequate for devising new and more efficient methods needed to develop a sustainable and economical biofuels industry. Although many new organisms containing useful enzymes may be discovered and the resulting genomes may be sequenced, the successful selection of the most promising new organisms for such purposes is difficult at best, and effective tools are not currently available to effectively focus proteomics efforts using any newly discovered gene sequences. Furthermore, conventional single enzyme studies do not adequately address the complexity of the biological problem. Thus, there is a need in the art for methods to efficiently and quickly discover effective combinations of enzymes and/or coordinated enzyme complexes for use in facilitating biomass transformation.

BRIEF SUMMARY OF THE INVENTION

The inventors disclose herein a method for using cell-free translation to identify polypeptides or combinations of polypeptides for modulating biomass transformation. In addition, the inventors disclose novel fusion proteins having utility as enzymes that facilitate biomass transformation. Furthermore, the inventors disclose herein cell-free expression systems containing combinations of polypeptides that effectively modulate biomass transformation.

Accordingly, in a first aspect, the invention encompasses a method for identifying a polypeptide that modulates biomass transformation. The method includes the steps of transcribing a nucleic acid fragment to make the corresponding mRNA; translating the mRNA in a cell-free environment comprising a cell-free extract to produce a polypeptide; contacting the polypeptide with biomass; and assaying the effect of the polypeptide on transformation of the biomass to determine whether the polypeptide modulates biomass transformation.

In certain embodiments, the method further includes the step of amplifying a first nucleic acid fragment to obtain the nucleic acid fragment that is transcribed. The method is not limited to the identification of a single polypeptide, and includes methods wherein more than polypeptide is produced within the same cell-free environment to thereby identify a combination of polypeptides that modulate biomass transformation.

Although the cell-free environment in which translation takes place may include a number of cell-free extracts, a preferred cell-free extract is wheat germ extract. In certain embodiments, the step of transcribing the nucleic acid fragment also occurs in a cell-free environment that includes a cell-free extract.

Optionally, the nucleic acid is transcribed from a linear template. In certain embodiments, the nucleic acid is incorporated into an expression vector before it is transcribed. The steps of transcribing the nucleic acid fragment and translating the corresponding mRNA may in some embodiments occur within the same cell-free environment. Preferably, the cell free environment used in the method further contains amino acids, creatine phosphate, creatine kinase, liposomes, and nucleosides.

In some embodiments, the polypeptide is not purified before contact with the biomass. The biomass transformation that is assayed by the method is not limited to a specific type of biomass transformation, but includes without limitation the degradation of one or more of cellulose, hemicellulose, starch, pectin, lignin, and chitin. Similarly, the biomass contacted with the polypeptide is not limited to any particular type of biomass, but may include without limitation one or more of corn stover, switchgrass, paper, cellulose, a monosaccharide, a disaccharide, a polysaccharide, or animal feed.

In certain embodiments, the polypeptide is fused with a dockerin domain, a cellulose binding domain, or both. The step of assaying the effect of the polypeptide on biomass transformation is not limited to any particular method, but includes without limitation one or more of high pressure liquid chromatography (HPLC), an enzyme coupled colorimetric or fluorometric assay, a filter paper assay, and a gas evolution assay.

In a second aspect, the invention encompasses novel cc_CBM fusion polypeptides, including one or more of the amino acid sequences of the fusion proteins CelAcc_CBM (SEQ ID NO:1), CelKcc_CBM (SEQ ID NO:2), CelLcc_CBM (SEQ ID NO:3), CelRcc_CBM (SEQ ID NO:4), ChiAcc_CBM (SEQ ID NO:5), LicBcc_CBM (SEQ ID NO:6), ManAcc_CBM (SEQ ID NO:7), XynCcc_CBM (SEQ ID NO:8), or XynYcc_CBM (SEQ ID NO:9), as well as nucleic acids comprising a sequence coding for one or more of the amino acid sequences set forth in SEQ ID NO:1, SEQ ID NO:2, SEQ ID NO:3, SEQ ID NO:4, SEQ ID NO:4, SEQ ID NO:5, SEQ ID NO:6, SEQ ID NO:7, SEQ ID NO:8, or SEQ ID NO:9.

In a third aspect, the invention encompasses cell-free expression systems including a cell-free extract for synthesizing a desired target polypeptide, and a nucleotide sequence encoding one or more of the amino acid sequences set forth in SEQ ID NO:1, SEQ ID NO:2, SEQ ID NO:3, SEQ ID NO:4, SEQ ID NO:4, SEQ ID NO:5, SEQ ID NO:6, SEQ ID NO:7, SEQ ID NO:8, or SEQ ID NO:9.

In a third aspect, the invention encompasses cell-free expression systems including a cell-free extract for synthesizing a desired target polypeptide, a first nucleotide sequence encoding a first fusion protein, the first fusion protein comprising a first cohesin domain and a first biomass binding domain, and a second nucleotide sequence encoding a second fusion protein, the second fusion protein comprising a first dockerin domain and a first target polypeptide that has a biological activity of catalyzing biomass transformation. When the first and second fusion proteins are expressed, the first cohesin domain can associate with the first dockerin domain.

In certain embodiments, the cell-free expression system further includes a third nucleotide sequence encoding a third fusion protein, the third fusion protein comprising a second mass binding domain and a second target polypeptide. In some such embodiments, the cell-free expression system further includes a fourth nucleotide sequence encoding a third target polypeptide. In some such embodiments, the expression system further includes a fifth nucleotide sequence encoding a second cohesin domain. This embodiment may further include a sixth nucleotide sequence encoding a fourth fusion protein that comprises a second dockerin domain and a fourth target polypeptide.

Optionally, a linker domain may separate the first cohesin domain and the first biomass binding domain, and/or a linker domain may separate the first dockerin domain and the target polypeptide. In certain embodiments of the cell-free expression system, the cohesin domain and/or the dockerin domain are isolated from *Clostridium thermocellum*.

These and other features of various exemplary embodiments of the systems and methods of the invention are described in, or are apparent from, the following detailed description and accompanying drawings.

DETAILED DESCRIPTION OF PREFERRED EMBODIMENTS

Figure 1:
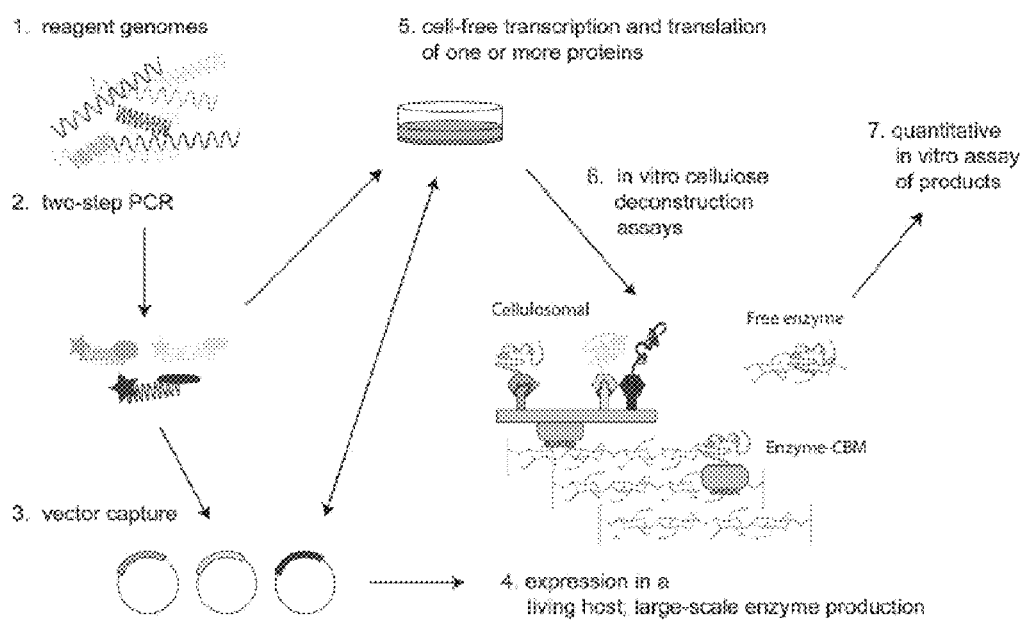
FIG. 1 is a schematic diagram illustrating a platform developed for the identification of target polypeptides and polypeptide combinations capable of modulating biomass transformation.

The invention encompasses methods of using cell free systems for identifying polypeptides that modulate biomass transformation. Genes coding target polypeptides are amplified and then expressed in cell-free systems to produce target polypeptides. The target polypeptides produced are then contacted with the biomass, and the effect of the target polypeptides on the biomass is assayed to thereby identify compounds that modulate biomass transformation. Using cell-free expression, there is no need to purify preparations of the target polypeptides before contacting the preparations with the biomass.

The methods may further include contacting a plurality of target polypeptides produced in cell-free expression systems with the biomass and determining the effect of the plurality of target polypeptides on the biomass to thereby identify a plurality of target polypeptides that modulate biomass transformation. In the practice of these methods, the biomass transformation may include without limitation deconstruction of cellulose, hemicellulose, starch, pectin, chitin or other polysaccharides, or changes in the makeup of animal feed. The biomass may be an untreated material, or in some manner be pre-treated. Methods of pre-treatment of biomass are known in the art, and include without limitation chemical pre-treatments with acid, steam, ionic liquids, alkaline hydrogen peroxide, and high pressure ammonia fiber explosion (AFEX).

In another aspect, the invention encompasses novel polypeptides having utility in biomass transformation and nucleic acid sequences coding for such polypeptides. In particular, the invention encompasses a polypeptide comprising one or more of the amino acid sequences of the fusion proteins CelAcc_CBM (SEQ ID NO:1), CelKcc_CBM (SEQ ID NO:2), CelLcc_CBM (SEQ ID NO:3), and CelRcc_CBM (SEQ ID NO:4), ChiAcc_CBM (SEQ ID NO:5), LicBc-c_CBM (SEQ ID NO:6), ManAcc_CBM (SEQ ID NO:7), XynCcc_CBM (SEQ ID NO:8), or XynYcc_CBM (SEQ ID NO:9), or a nucleic acid comprising a sequence coding for one or more of these fusion proteins.

The invention further encompasses cell-free expression systems, which include: cell-free extracts for synthesizing desired target polypeptides; nucleotide sequences encoding fusion proteins, the fusion proteins comprising a cohesin domain and a biomass binding domain; and nucleotide sequences encoding other fusion proteins, the fusion proteins comprising a first dockerin domain and a target polypeptide that has a biological activity of catalyzing said biomass transformation. When both types of fusion proteins are expressed, the cohesin domains can associate with the dockerins domains. In the systems, the target polypeptide need not be in a purified form. In other embodiments of the cell-free expression system, the system includes cell-free extracts for synthesizing desired target polypeptides and nucleotide sequences encoding one or more of the following fusion proteins: CelAcc_CBM (SEQ ID NO:1), CelKcc_CBM (SEQ ID NO:2), CelLcc_CBM (SEQ ID NO:3), and CelRcc_CBM (SEQ ID NO:4), ChiAcc_CBM (SEQ ID NO:5), LicBc-c_CBM (SEQ ID NO:6), ManAcc_CBM (SEQ ID NO:7), XynCcc_CBM (SEQ ID NO:8), or XynYcc_CBM (SEQ ID NO:9).

The systems may further include nucleotide sequences encoding a third type of fusion proteins, the third type of fusion proteins comprising other biomass binding domains and other target polypeptides. The systems may also include nucleotide sequence encoding yet other target polypeptides. The systems may include linker domains separating the cohesin domains and the biomass binding domains; the systems may also include linker domains separating the dockerin domains and the target polypeptides. The systems may include one or more nucleotide sequence encoding other cohesin domains. The systems may include one or more nucleotide sequence encoding other fusion proteins that comprise one or more other dockerin domains and other target polypeptides. In the systems, the expressed cohesin domains may be adsorbed onto a substrate. At least one of the cohesin and/or dockerin domains may be isolated from *Clostridium thermocellum*.

Preferred embodiment of the invention are described herein in considerable detail. Many modifications and variations to the preferred embodiment described will be apparent to a person of ordinary skill in the art. Therefore, the invention should not be limited to the embodiments described.

In one aspect, the compositions and methods of the present invention are made possible by the inventors' discovery of compositions and methods for the expression of enzymes in a combinatorial manner, and for assaying them without requirement for intermediate cloning steps and without purification of the protein products. The expressed target polypeptides may include without limitation one or more known enzymes or one or more unknown enzymes or proteins capable of binding to cellulose, hemicellulose, pectin, starch, chitin, or other polysaccharides, or may also include one or more known enzymes or one or more unknown enzymes or proteins capable of hydrolyzing glycoside bonds present in cellulose, hemicellulose, pectin, starch, chitin or other polysaccharides, or combinations of known and unknown enzymes and proteins capable of these properties. The compositions and methods of the present invention can be used with a variety of enzymes, proteins and enzymatic processes.

In one preferred embodiment of the invention, compositions and methods useful for the deconstruction of cellulose, hemicellulose, pectin, starch, chitin or other polysaccharides in the biomaterial area are provided, with application to production of soluble sugar hydrolysates suitable for fermentation or chemical conversion to products such as ethanol, butanol, hexanol, hexanes, heptanes, octanes, octanol, aromatic compounds, and the like.

Some advantages of the present invention relative to previous systems known in the art include: potential for high-throughput analysis; ability to evaluate genes in multiple expression systems and multiple classes of enzyme architectures; ability to make combinatorial arrangements of genes and proteins; reliability of analytical determinations because of the absence of competing cellular reactions; ability to perform quantitative detection and product analysis without obtaining purified preparations of target polypeptides; ability to determine the pH, ionic strength, solvent and thermal stability of the target polypeptides.

The practice of the present invention employs, unless otherwise indicated, conventional techniques of molecular biology (including recombinant techniques), microbiology, cell biology, biochemistry, immunology, protein kinetics, and mass spectroscopy, which are within the skill of art. Such techniques are explained fully in the literature, such as in Sambrook et al., 2000, *Molecular Cloning: A Laboratory Manual*, third edition, Cold Spring Harbor Laboratory Press, Cold Spring Harbor, N.Y.; Ausubel et al., 1987-2004, *Current Protocols in Molecular Biology*, Volumes 1-4, John Wiley & Sons, Inc., New York, N.Y.; Kriegler, 1990, *Gene Transfer and Expression: A Laboratory Manual*, Stockton Press, New York, N.Y.; Dieffenbach et al., 1995, *PCR Primer: A Laboratory Manual*, Cold Spring Harbor Laboratory Press, Cold Spring Harbor, N.Y., each of which is incorporated herein by reference in its entirety. Procedures employing commercially available assay kits and reagents typically are used according to manufacturer-defined protocols unless otherwise noted.

Generally, the nomenclature and the laboratory procedures in recombinant DNA technology described below are those well known and commonly employed in the art. Standard techniques are used for cloning, DNA, RNA, and protein isolation, nucleic acid amplification, and nucleic acid and protein purification. Generally enzymatic reactions involving DNA ligase, DNA polymerase, restriction endonucleases and the like are performed according to the manufacturer's specifications.

"Nucleic acid" or "polynucleotide sequence" refers to a single or double stranded polymer of deoxyribonucleotide or ribonucleotide bases read from the 5' to the 3' end. Nucleic acids may also include modified nucleotides that permit correct read-through by a polymerase and do not alter expression of a polypeptide encoded by that nucleic acid.

"Nucleic acid sequence encoding" refers to a nucleic acid that directs the expression of a specific protein or peptide. The nucleic acid sequences include both the DNA strand sequence that is transcribed into RNA, and the RNA sequence that is translated into protein. The nucleic acid sequences include both the full length nucleic acid sequences as well as non-full length sequences derived from the full length sequences. The sequences may includes the degenerate codons of the native sequence or sequences that may be introduced to provide codon preference in a specific host cell.

"Coding sequence" or "coding region" refers to a nucleic acid molecule having sequence information necessary to produce a gene product, when the sequence is expressed.

"Nucleic acid construct" or "DNA construct" refers to a coding sequence or sequences operably linked to appropriate regulatory sequences so as to enable expression of the coding sequence.

"Isolated," "purified," or "biologically pure" refer to material that is substantially or essentially free from components that normally accompany it as found in its native state. This state is typically obtained by laborious multi-step processing of biological fluids including cellular lysis, precipitation, centrifugation, chromatographic steps including adsorption, affinity, or size exclusion, filtration, crystallization, dissolution in denaturing substances and refolding by removal of the denaturants and other methods. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. One of skill will recognize that these values can be appropriately adjusted to determine corresponding identity of proteins encoded by two nucleotide sequences by taking into account codon degeneracy, amino acid similarity, reading frame positioning and the like.

"Substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%. Polypeptides that are "substantially identical" share sequences as noted above except that residue positions that are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

A protein "isoform" is a version of a protein with some small differences. For example, the small differences may be a result of a splice variant of the protein, or they may be the result of some post-translational modification. An isoform may also arise from a change in the nucleotide sequence of the corresponding gene. This change may include natural variation, changes introduced by low fidelity replication, transcription, or translation, or inadvertent or intentional introduction of changes into the gene coding sequence. Often, an isoform of an enzyme may have different properties than the native form of the enzyme.

"Fusion protein" refers to a protein created through genetic engineering from two or more proteins or polypeptides, or from domains of proteins or polypeptides. This is achieved by creating a fusion gene: removing the stop codon from the DNA sequence of the first protein; then appending the DNA sequence of the second protein in frame. That DNA sequence will then be translated by cellular or cell-free ribosomal enzymes as a single protein. An example of a fusion protein is one that includes: (i) a protein of interest as a first protein, (ii) optionally a linker, and (iii) a unique binding domain. Expression of the fusion protein results in accumulation of the protein of interest, linker, and the binding domain as a single entity. In fusion proteins, often "linker" (or "spacer") domain or peptide is also added between the first and the second protein or polypeptide. The linker typically makes it more likely that the expressed proteins fold independently and have biological activity or functionality. Especially in the case where the linkers enable protein purification, linkers in protein fusions are sometimes engineered with cleavage sites for proteases or chemical agents, which enable the liberation of the two separate proteins.

"Biological activity" is being used here in its broadest sense to denote function. For example, biological activity may refer to enzymatic activity. Sometimes it may be possible to correlate biological activity to structure.

"Biomass transformation" is being used here in its broadest sense and includes, but is not limited to, biomass deconstruction, biomass degradation, biomass processing, biomass fermentation, etc. One example of biomass transformation is the conversion of plant biomass such as cellulose to fermentable sugars. Another example of biomass transformation is degradation of plant material (e.g., corn stover, switchgrass, etc.) into relatively simpler organic compounds. A third example of biomass transformation is the partial breakdown of animal feed to produce a more efficient feedstock. Compositions and methods are provided to enhance the ability to make, express, and identify target polypeptides such as enzymes capable of enhancing deconstruction of biomass that includes of cellulose, hemicellulose, pectin, starch, chitin or other polysaccharides to fermentable sugars.

Thus, in one aspect, the invention relates to a system in which naturally occurring or artificial genes or gene combinations are incorporated into the platform for discovery of new enzyme combinations. For example, FIG. 1 illustrates how the system of the present invention can be used to discover new enzymes for biomass deconstruction or other biofuels processes. Reagent genomes (FIG. 1; step 1) such as those discovered by the US Department of Energy Joint Genome Institute (JGI), the Great Lakes Bioenergy Research Center (GLBRC), or others provide open reading frames suitable for incorporation by this method. A two-step PCR (FIG. 1; step 2) provides linear transcripts that can be directly evaluated by cell-free translation (FIG. 1; step 5). In one preferred embodiment, FlexiVector™ (Promega, Madison, Wis.) cloning can be used to capture the same PCR products into cell-free translation vectors or bacterial expression vectors for other research purposes (FIG. 1; step 3), including large-scale production of desired protein isoforms (FIG. 1; step 4).

Expression vectors are provided that permit the transcription and subsequent translation of a gene into target polypeptides that can act as free enzymes, as enzymes bound to cellulose or other polysaccharides, or as enzymes present in an engineered approximation of a cellulosomal architecture. These target polypeptides may be produced as individual proteins or as a combinatorial assembly in bacterial cells or other living expression hosts. Preferably, these target polypeptides may also be produced in cell-free translation. "Cell-free translation" is a method for the synthesis of target polypeptides. "Cell-free translation" refers to the synthesis of proteins in vitro, for example using cell-free extracts from rabbit reticulocytes, wheat germ, synthetic systems (e.g., protein synthesis by pure translation systems—PURE; New England Biolabs), *Escherichia coli*, etc.

Target polypeptides produced in bacterial cells or in other living expression hosts may be added to the deconstruction reactions assembled from the cell-free translation to increase the combinatorial capacity of the investigation, and thus reveal unique patterns of biomass transformation.

Assembly of target polypeptides in cell-free translation allows quantitative assay of reaction products, as these substances are shown herein to be relatively stable when expressed in cell-free preparations such as wheat germ extract. In some preferred embodiments it is not necessary to purify target polypeptides in order to determine their biomass transformation properties. In contrast, when conventional methods in the art are used, soluble sugars are rapidly consumed by living systems, which complicate or preclude detection and analysis of biomass transformation properties when using living systems as the expression host. Furthermore, preparation of bacterial cell lysates containing target polypeptides also contain contaminating bacterial proteins and enzymes capable of altering soluble sugars, demanding purification of target polypeptides before their biomass transformation properties can be determined. These requirements of living systems introduce undesirable complications, time constraints, and costs.

Figure 2:
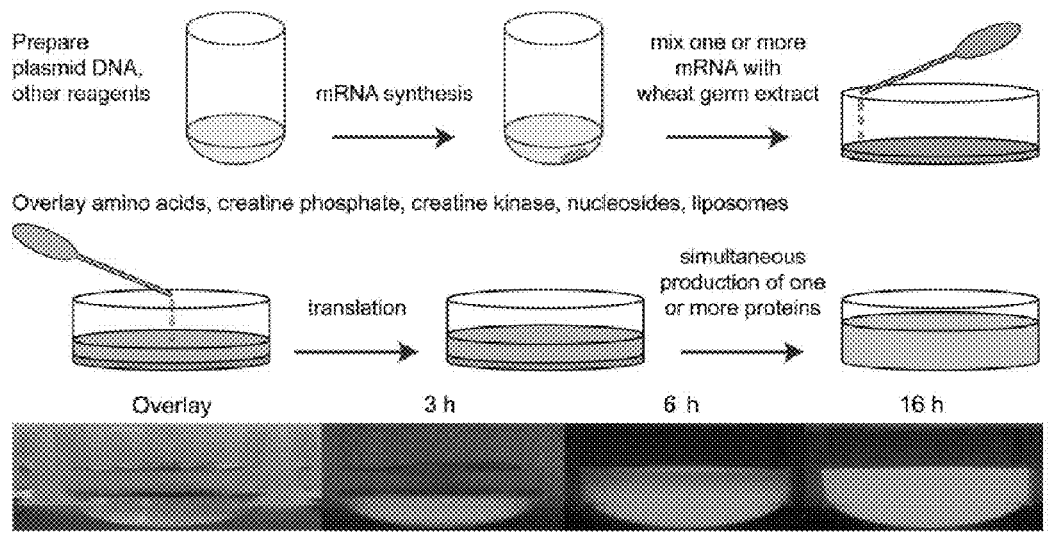
FIG. 2 is a schematic representation of a cell-free expression procedure.

In one embodiment of this system, cell-free translation of single genes can reveal new target polypeptides such as enzymes from reagent genomes. FIG. 2 shows a schematic representation of cell-free translation. These target polypeptides may have utility in biomass transformation. In another version, simultaneous cell-free translation of multiple genes in the presence of biomass can be used to identify optimal combinations of currently known enzymes (e.g., as indicated in FIG. 1; step 6) to yield biomass deconstruction. Thus the constructs of the present invention permit combinatorial studies of the role of synergy in deconstruction of biomass composed of cellulose, hemicellulose, pectin, starch, chitin, and other polysaccharides. In vitro assays developed for use in a multi-well format with natural cellulosic biomass substrates can provide quantitative assessments of this deconstruction (FIG. 1; step 7 and FIG. 3), and thus represent a powerful and conclusive approach relative to the use of small molecule substrate analogs typical in other discovery work currently undertaken for biomass deconstruction. Any biomass assay may be used in the present method; preferred assays include without limitation assays that measure solubilization of biomass, such as the use of high pressure liquid chromatography (HPLC) to identify (and optionally quantify) soluble sugars and other biomass deconstruction products or the use of enzyme coupled colorimetric or fluorometric assays to identify (and optionally quantify) biomass deconstruction reaction products and intermediates. When the method is used to assess feed additives, gas evolution assays can be used to evaluate given combinations for their ability to facilitate biomass transformation.

In one preferred example, schematically illustrated in FIG. 1, step 6, free target polypeptides are expressed without modification of the natural gene sequence.

In another preferred example, schematically illustrated in FIG. 1, step 6, target polypeptides are expressed as a fusion with a carbohydrate binding domain, cellulose binding domain, cellulose binding module, or other binding domain.

In another preferred example, schematically illustrated in FIG. 1, step 6, target polypeptides are expressed as a fusion with a dockerin domain, permitting assembly into cellulosomal architecture.

In one preferred embodiment, cell-free protein (or polypeptide) expression systems are provided, which provide expressed proteins (or polypeptides) with relatively higher stability in comparison to other proteins expressed using conventional comparable protein expression methods known in the art. In other preferred embodiments, products of the enzymatic reactions of the above polypeptides are provided, which products also have relatively higher stability in comparison to other products obtained using conventional comparable enzymatic methods known in the art.

One utility of the present invention is that the same gene can be simultaneously placed into each of the contexts described above, e.g. without modification of the natural gene sequence, and expressed in cell-free translation allowing rapid evaluation of the natural biological contexts known for biomass deconstruction.

Figure 11:
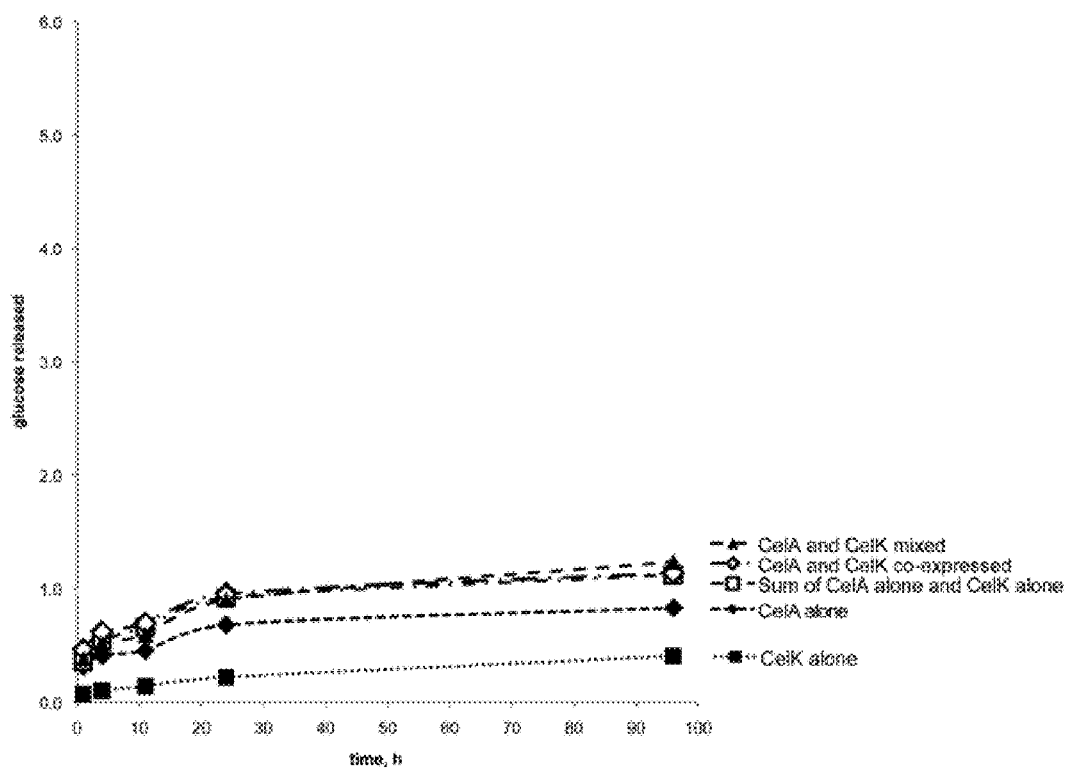
FIG. 11 is a graph of glucose released as a function of time for the deconstruction of phosphoric acid-treated cellulose for five different enzyme combinations/conditions.
Figure 12:
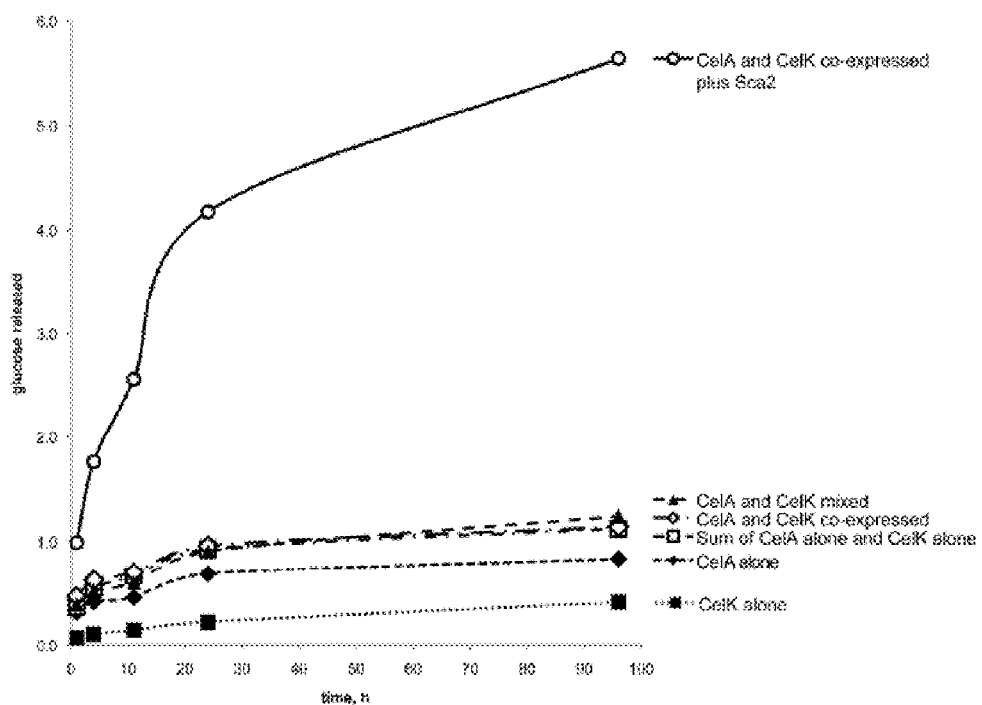
FIG. 12 is a graph of glucose released as a function of time with the same data as shown in FIG. 10, but additionally including the data for the combination of CelA and CelK co-expressed with exogenously added Sca2 protein.
Figure 14:
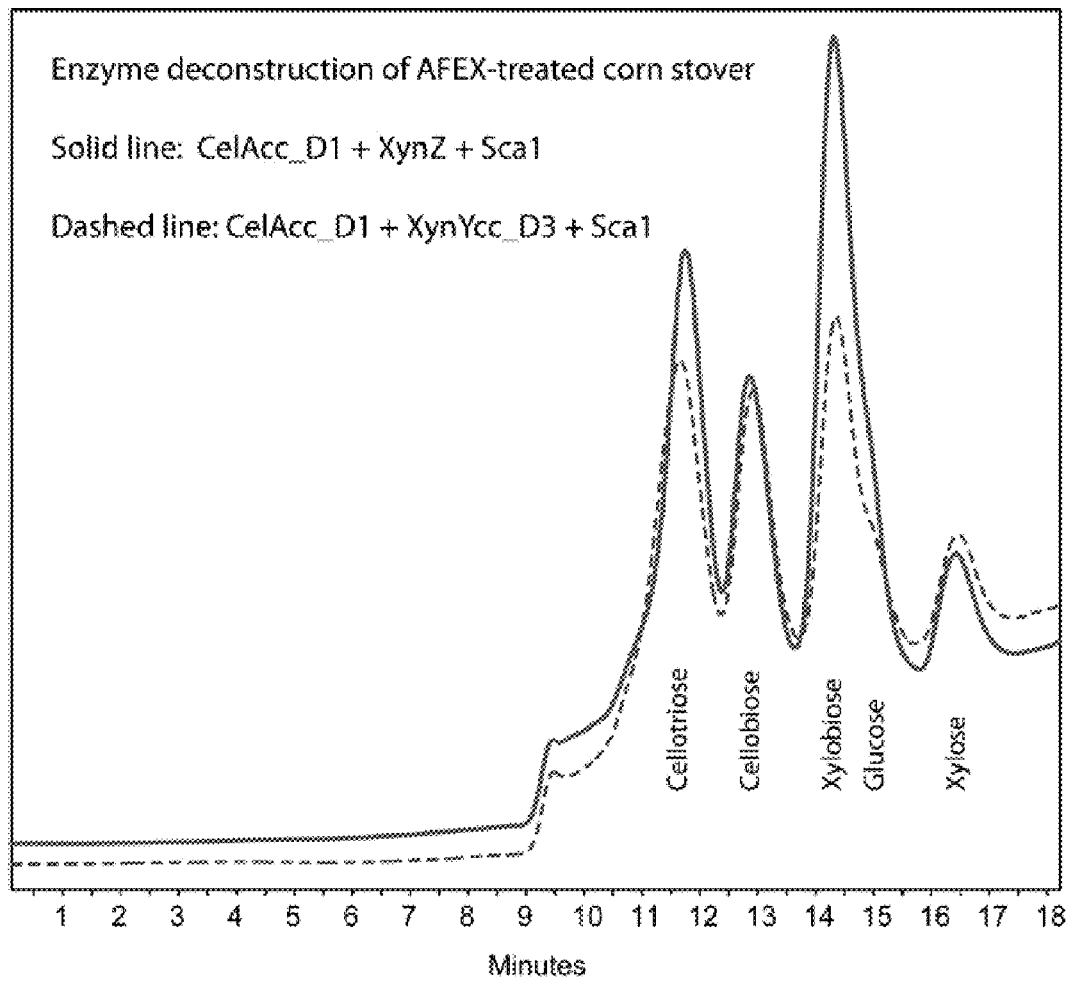
FIG. 14 is a graph of HPLC data for five soluble sugars from the endpoint of cellulose deconstruction of AFEX-treated corn stover using two different polypeptide combinations.

In another preferred example, schematically illustrated in FIG. 1, combinations of target polypeptides from all of the classes described herein, with known or unknown functions, can be simultaneously expressed and assayed for biomass deconstruction without need for purification of the individual target polypeptides. For example, FIG. 11 shows the results of an HPLC deconstruction assay using free enzymes alone (CelA or CelK), combinations of free enzymes (CelA plus CelK), and combinations of free enzymes that are additionally co-expressed. FIG. 12 shows the same results as FIG. 11, but additionally shows the result for the combination of enzymes co-expressed with the scaffoldin format (CelA and CelK plus Sca2). FIG. 14 shows the deconstruction of AFEX-corn stover with CelA and XynY in a scaffoldin format (CelAcc_D1+XynYcc_D3+Seal; dashed line) versus CelA in a scaffoldin format and XynZ produced from the vector shown in FIG. 4 (CelAcc_D1+XynZ+Sca1; solid line).

Expression of the target proteins envisioned by the present invention may be partly or wholly accomplished through the use of expression vectors, such as plasmids. Indeed, expression of target polypeptides in living hosts such as *E. coli* is obligate dependent on the production of an expression plasmid as an intermediate cloning step. However, expression vectors are not required to carry out cell-free translation, where methods to prepare linear, plasmid-free preparations as intermediates in expression of target polypeptide are known in the art. In some preferred embodiments, a single PCR reaction can simultaneously populate each of the vectors described herein.

The vector systems of the present invention are preferably built to allow expression of the target polypeptide alone, the target polypeptide enzyme fused to some manner of cellulose-binding domain, or the target polypeptide fused to a dockerin. These combinations allow dissection of the contributions of target polypeptides free in solution, directly bound to cellulose, or assembled into macromolecular complexes that may or may not be bound to biomass materials.

Figure 4:
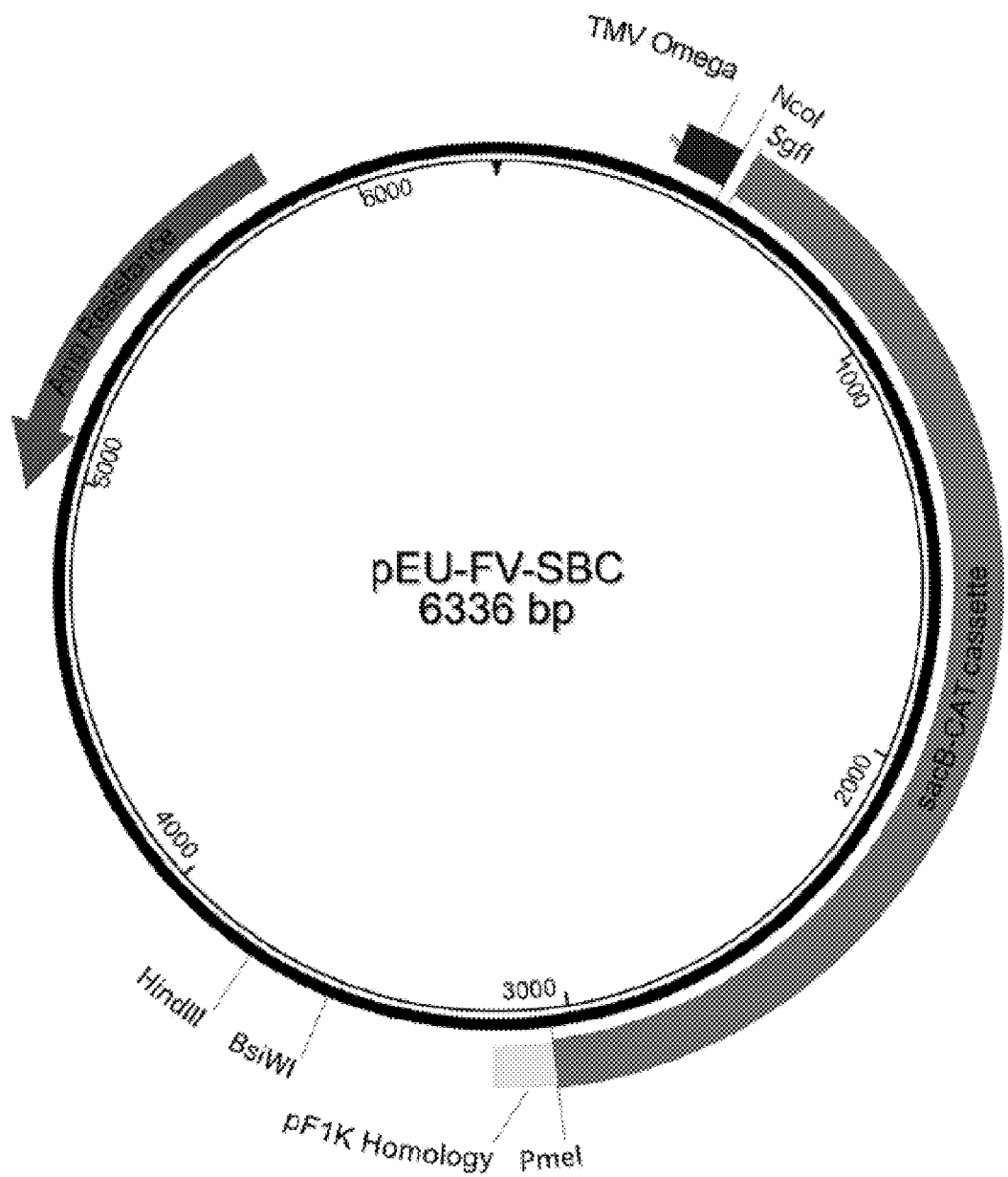
FIG. 4 is a schematic representation of an expression vector used for cell-free translation of a target polypeptide without modification of the natural coding nucleotide sequence.

An example of a vector created for the present invention to produce a targeted polypeptide without additional domains is shown in FIG. 4.

Figure 5:
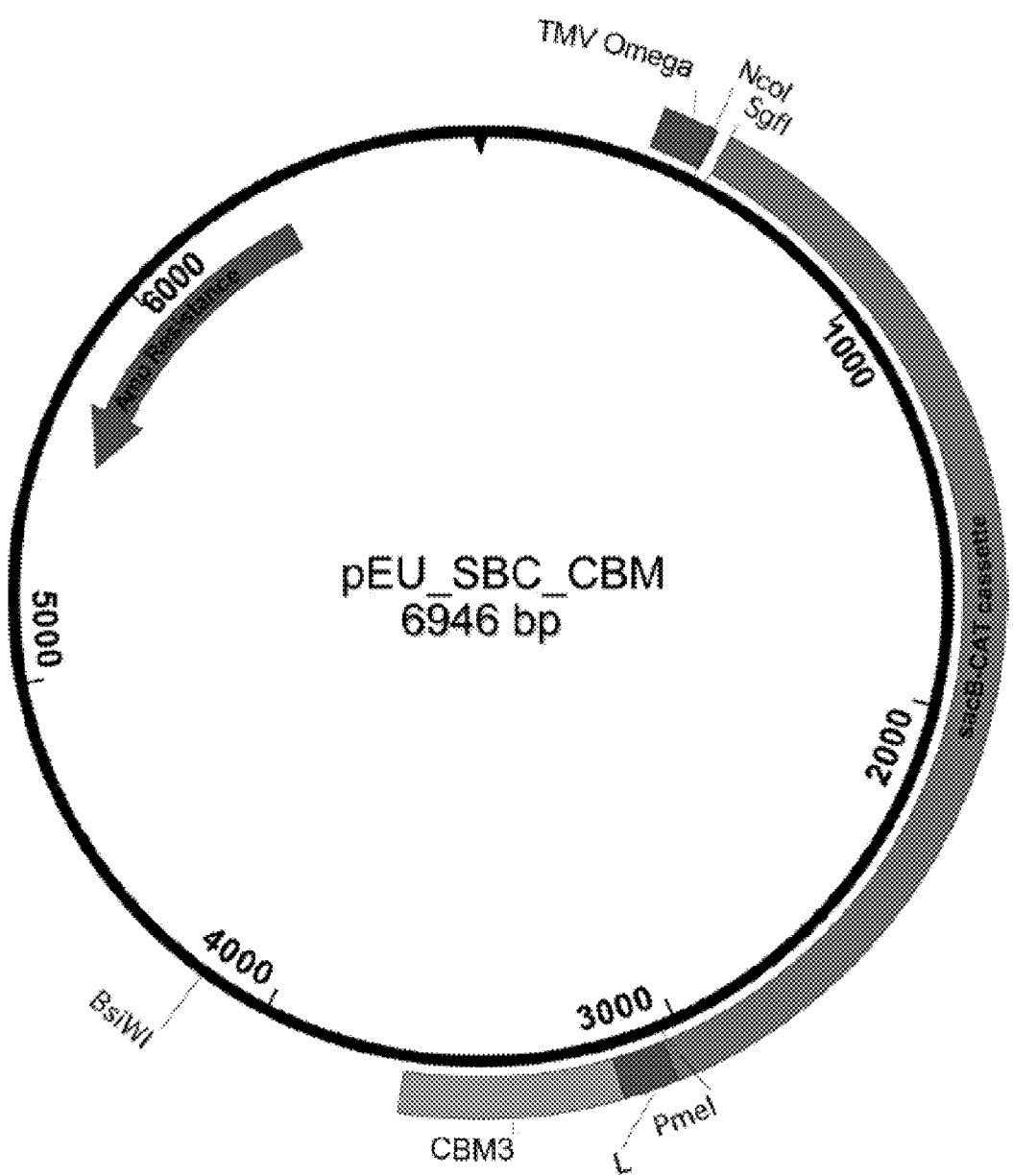
FIG. 5 is a schematic representation of an expression vector used for cell-free translation of a target polypeptide fused to an example carbohydrate-binding domain.

An example of a vector (Cbd vector) according to the present invention, to include a fusion of a cellulolytic enzyme and a cellulose-binding domain with a linker region interposed between them, is shown in FIG. 5. Other arrangements of enzymes and domains are anticipated.

Figure 6:
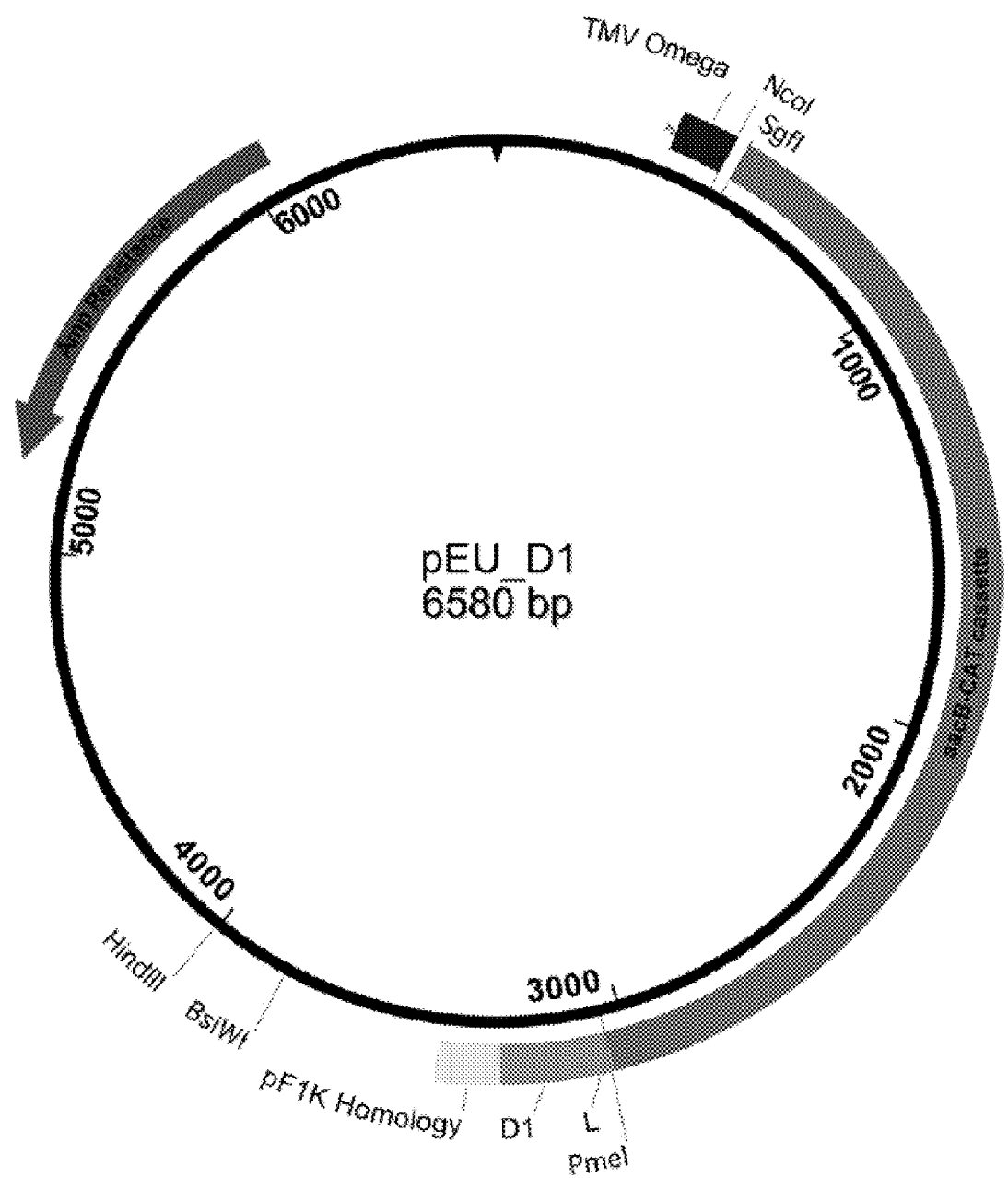
FIG. 6 is a schematic representation of an expression vector used for cell-free translation of a target polypeptide fused to an example dockerin domain.

An example of a vector according to the present invention, to include a fusion of a cellulolytic enzyme and a dockerin domain with a linker region interposed between them, is shown in FIG. 6. Other arrangements of enzymes and dockerin domains are possible as well, e.g. as shown in Table 2.

Figure 7:
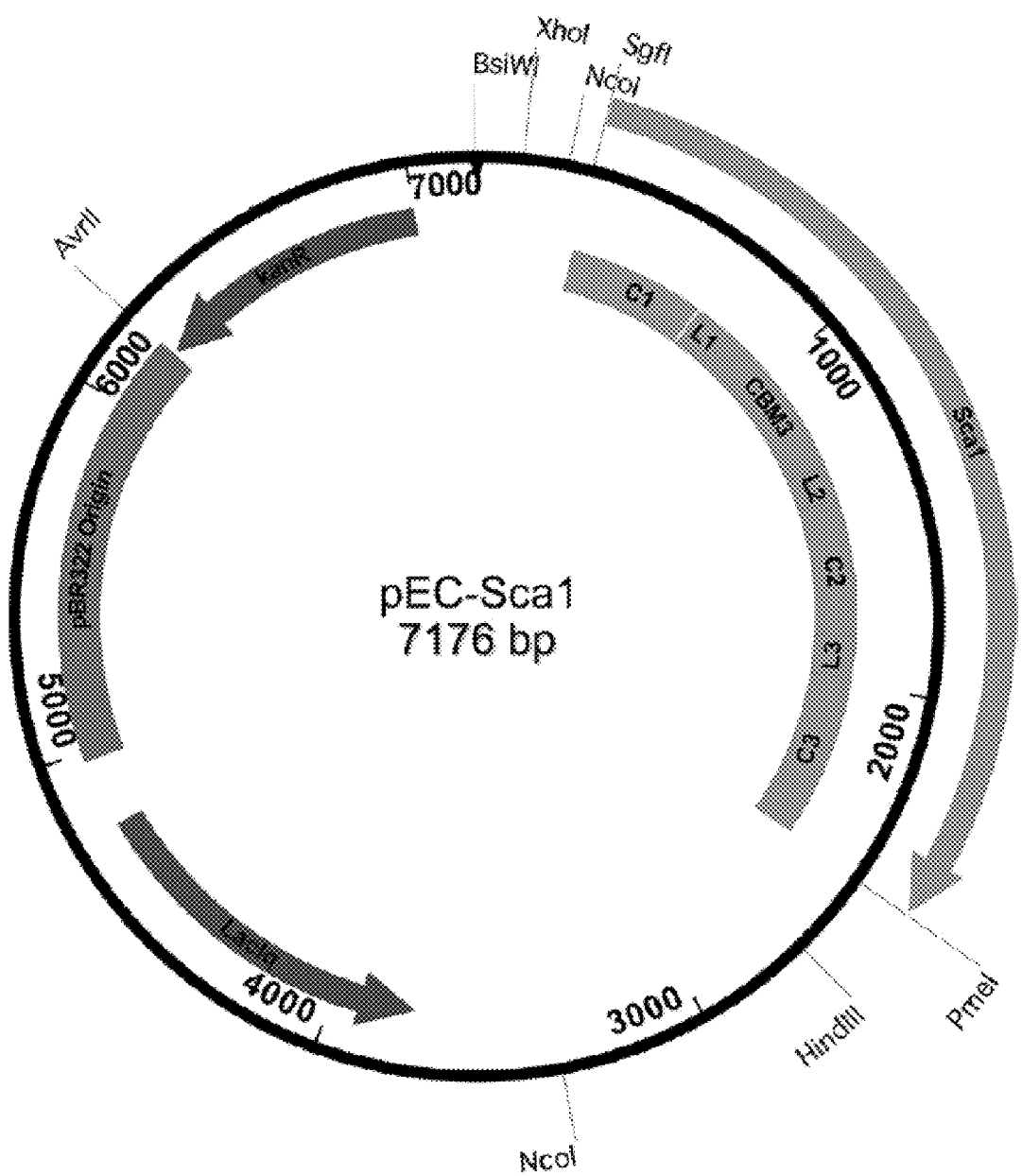
FIG. 7 is a schematic representation of an expression vector used for expression in E. coli of a fusion protein Sca1.
Figure 8:
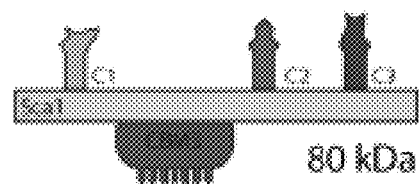
FIG. 8 is a schematic diagram of the scaffoldin fusion proteins Sca1 (top), Sca2 (second from the top), Sca3 (second from the bottom), and Sca4 (bottom).
Figure 8:
Figure 8:
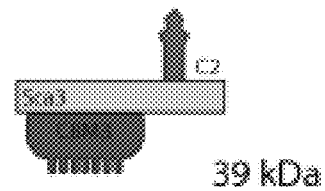
Figure 8:
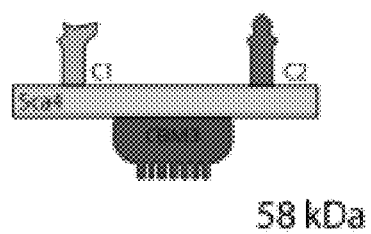

Another example of a vector according to the present invention is depicted in FIG. 7, which shows a vector used for expression in *E. coli* of a fusion protein Sca1, which comprises a type 1 cohesin domain C1, a linker region L1, a cellulose binding module CBM3, another linker region L2, a cohesin isoform domain C2, a linker region L3, and a type 2 cohesin domain C3. Likewise, Sca2 comprises a type 1 cohesin domain C1, a linker region L1, and a cellulose binding module CBM3; Sca3 comprises a cellulose binding module CBM3, a linker region L2, and a cohesion isoform domain C2; while Sca4 comprises a type 1 cohesin domain C1, a linker region L1, a cellulose binding module CBM3, another linker region L2, and a cohesion isoform domain C2. These combinations are shown in FIG. 8 as schematic representations.

In some embodiments, novel expression vectors, such as pSca1, pSca2, pSca3, pSca4, are provided. These were assembled from the *C. thermocellum* scaffoldin gene Cthe_3077. For example, pSca1 was assembled from the *C. thermocellum* scaffoldin gene Cthe_3077 by removing the first cohesin domain, taking the second cohesin domain and the cbm3 domain and the ensuing linker as is, mutagenizing the natural second cohesin domain to alter the specificity of the domain, repeating it after the cbm3 domain, adding another linker, and then taking the cohesin domain from another polypeptide, SdbA, which has a different specificity, to create Sca1. The arrangement in Sca1 is C1-L1-CBM3-L2-C2-L3-C3. C2 is engineered by mutagenesis to reverse the polarity of the binding interface. C3 is an orthogonal natural cohesin. All parts of Sca1 are from thermophilic organisms, so this is a thermostable complex. It provides three unique binding domains, which can be targeted to three unique dockerins, giving position specific placement of target polypeptides having unique dockerins. The dockerin tagged proteins are provided by the pDock vectors described herein (FIG. 6).

Cell-free protein translation is used in the compositions and methods of the present invention. FIG. 2 provides a schematic representation of the method of cell-free translation.

Cell-free protein translation is a powerful protein synthesis technique that uses extracts from either prokaryotic or eukaryotic sources, such as from rabbit reticulocytes, wheat germ, or *Escherichia coli*. Such compositions are prepared as crude extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract is supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.).

Cell-free expression systems offer an alternative to *E. coli* protein expression systems or other living cell-based expression platforms that are the mainstay of most enzyme discovery efforts. Because it decouples the production of difficult enzymes such as glycohydrolases from cellular homeostasis, cell-free translation can remove variability associated with the use of living expression hosts. A non-limiting example of the compositions, methods, and systems useful for cell-free translation is presented below.

In some aspects of the present invention, cell-free translation allows target polypeptides to be made independently of living systems, which readily consume glucose and other soluble sugars during cellular growth, causing loss of the products desired and needed for analysis. In this manner, the present invention simplifies the product detection and analysis process.

In some aspects of the present invention, target polypeptides obtained by cell-free translation can be reliably assayed for function directly in the cell-free translation reaction mixture without laborious purification procedures. In this manner, the present invention simplifies the enzyme discovery process.

Figure 9:
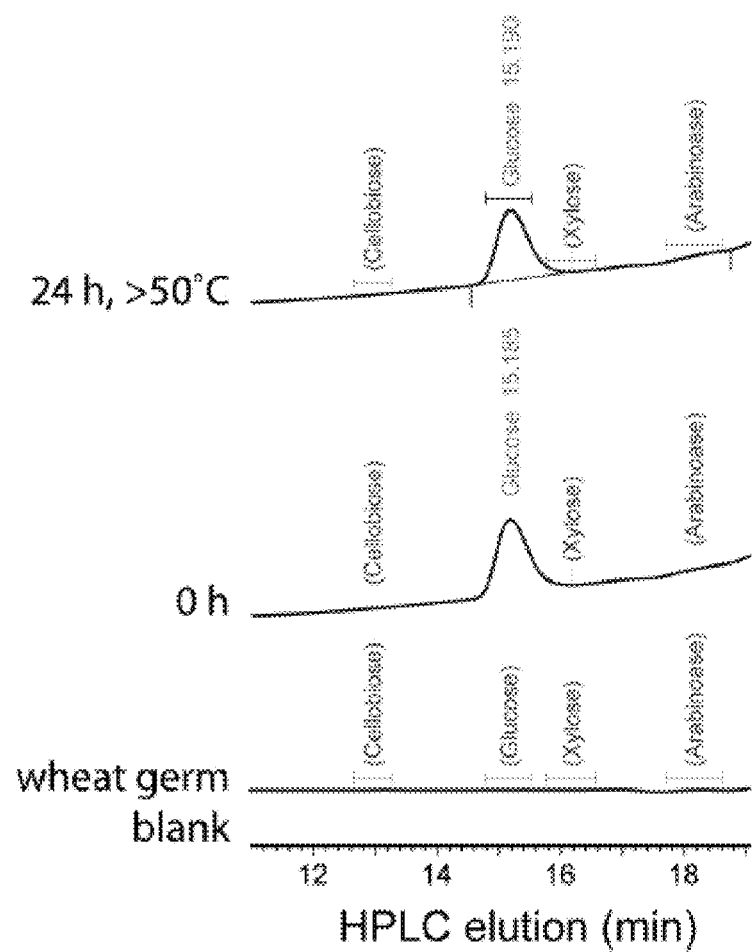
FIG. 9 is a graph of HPLC (high pressure liquid chromatography) data illustrating that glucose is not present in the cell-free extract blank sample (bottom line) and that added glucose is stable for an extended time period at elevated temperature in the cell-free extract.

In other aspects of the present invention, the soluble sugar products released from cellulose are stable over long time period in the cell-free extract (i.e. wheat germ extract). FIG. 9 is an HPLC trace demonstrating the stability of glucose over time in a cell-free system, and similar results were obtained for cellotetraose, cellotriose, cellobiose, xylobiose, and xylose. It is expected that other small molecular weight soluble sugars would also be stable in the cell-free translation reaction. Because of this, the present invention both improves the reliability of any soluble product-based detection and quantitative assay and also extends the time period available for detection and analysis.

Figure 10:
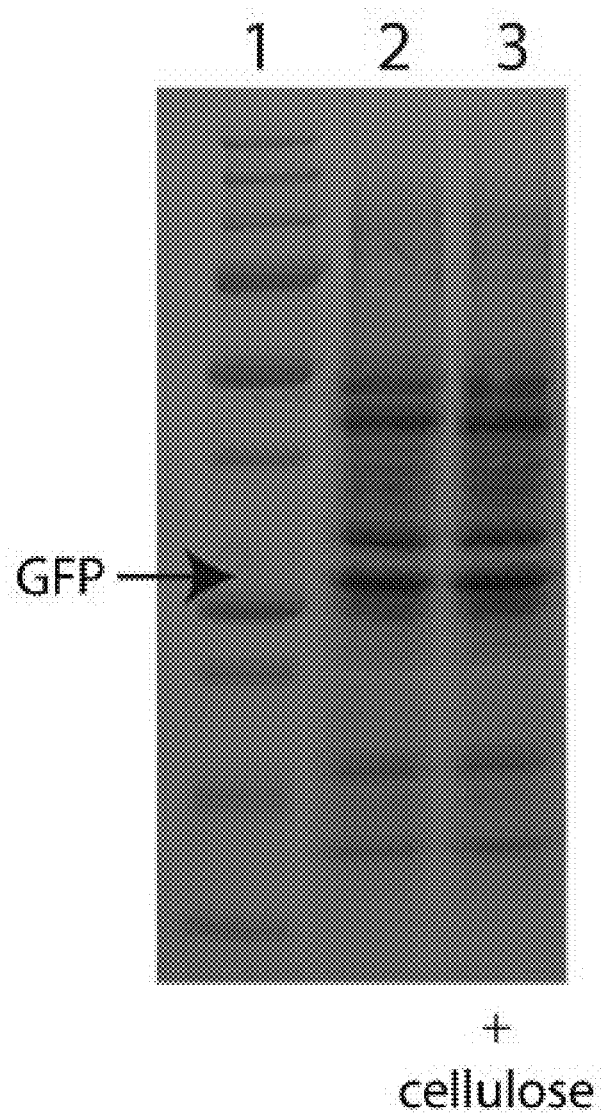
FIG. 10 shows an SDS-PAGE (sodium dodecyl sulfate polyacrylamide gel electrophoresis) analysis showing that cellulose can be added to the cell-free translation reaction (column 3) without inhibiting the protein synthesis reaction.

In yet other aspects of the present invention, cellulose or other natural or treated biomass substrates can be added directly to the cell-free translation reaction without affecting the efficiency of the protein synthesis carried out in the cell-free translation. FIG. 10 shows this result for expression of a control protein (GFP) in the presence of crystalline cellulose (lane 3). The inclusion of cellulose in the reaction stabilizes enzymes that bind to cellulose, and also permits immediate initiation and detection of catalytic activity studies without time delay or need for subsequent purification.

Figure 3:
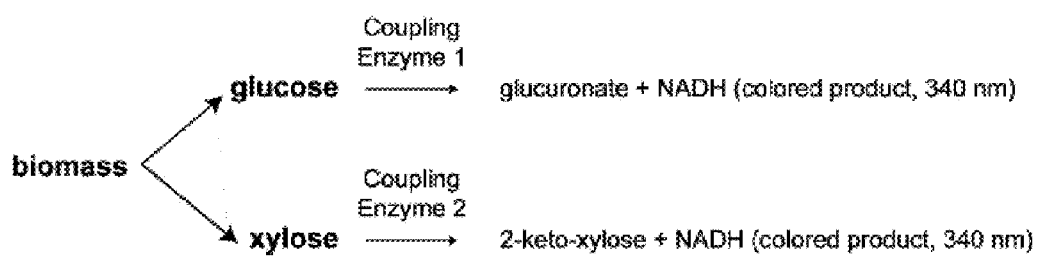
FIG. 3 is a schematic representation of two coupled enzyme reaction cascades (for glucose and xylose) that can be used in time-resolved detection of cellulose deconstruction after cell-free translation of target polypeptides.

Furthermore, in another aspect of the present invention, NADH is stable in the cell-free translation extract, so that coupling the enzyme reaction assays such as those shown in FIG. 3 will not be adversely influenced by adventitious degradation reactions.

Figure 13:
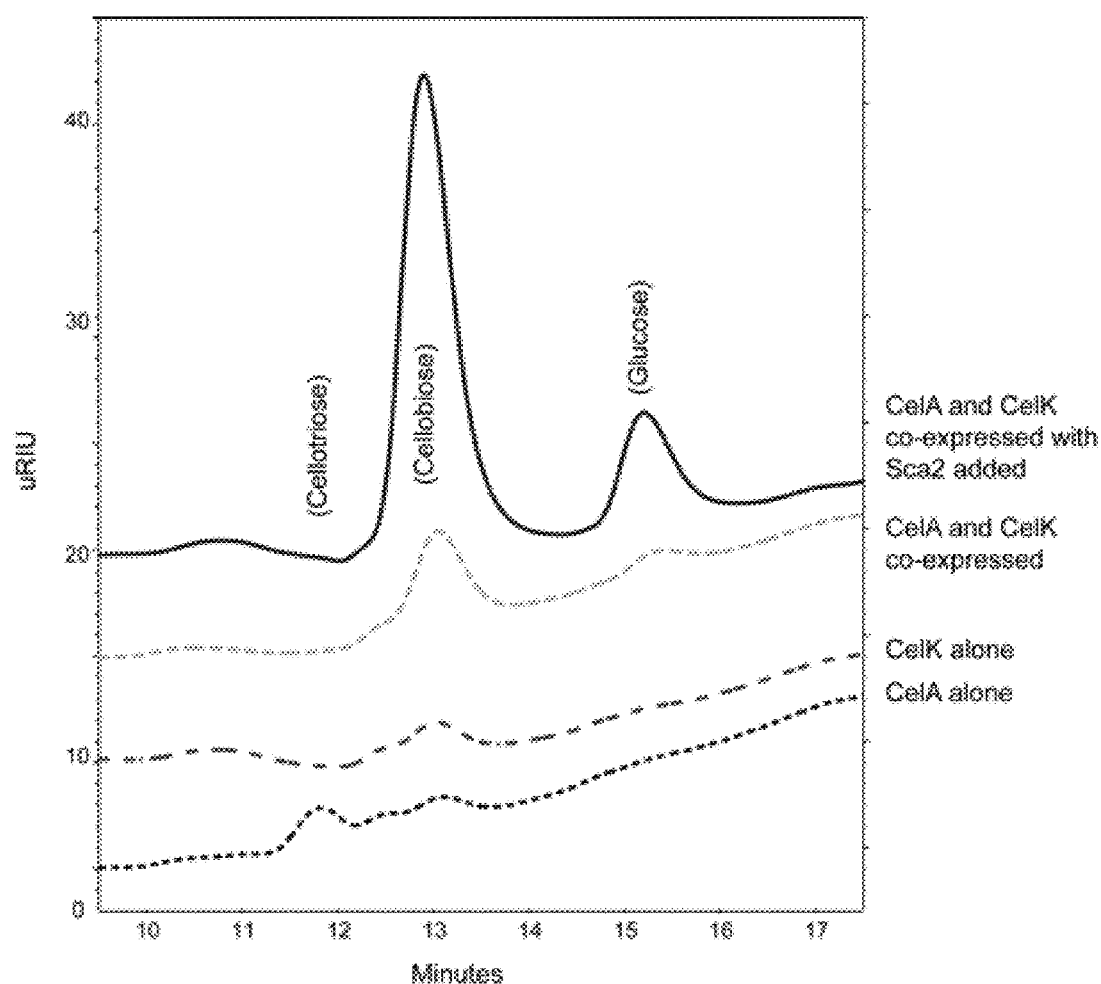
FIG. 13 is a graph of HPLC data for three soluble sugars from the 96 h endpoint of cellulose deconstruction reactions for four of the combinations shown in FIG. 12.

In yet another aspect of the present invention, it is demonstrated in FIG. 11, FIG. 12, and FIG. 13 that a cell-free translation of a minimal set of two example enzymes and an exogenously added engineered protein can convert phosphoric acid-treated cellulose to glucose in an efficient manner at a total enzyme loading ~10-fold lower than used in current state of the art methods.

FIG. 12 illustrates one utility of the discovery platform provided by the present invention, namely a demonstration of the influence of an exogenously added Sca2 protein in the deconstruction of phosphoric acid-treated cellulose. The graphs show cellulose deconstruction given by simultaneous cell-free translation of CelA and CelK (i.e., the same result as shown in FIG. 11). In this embodiment, the same cell-free translation of CelA and CelK of FIG. 11 was amended with Sca2 expressed in *E. coli*, purified by chromatographic approaches, and added to the assay of the cell-free translation reaction.

Figure 16:
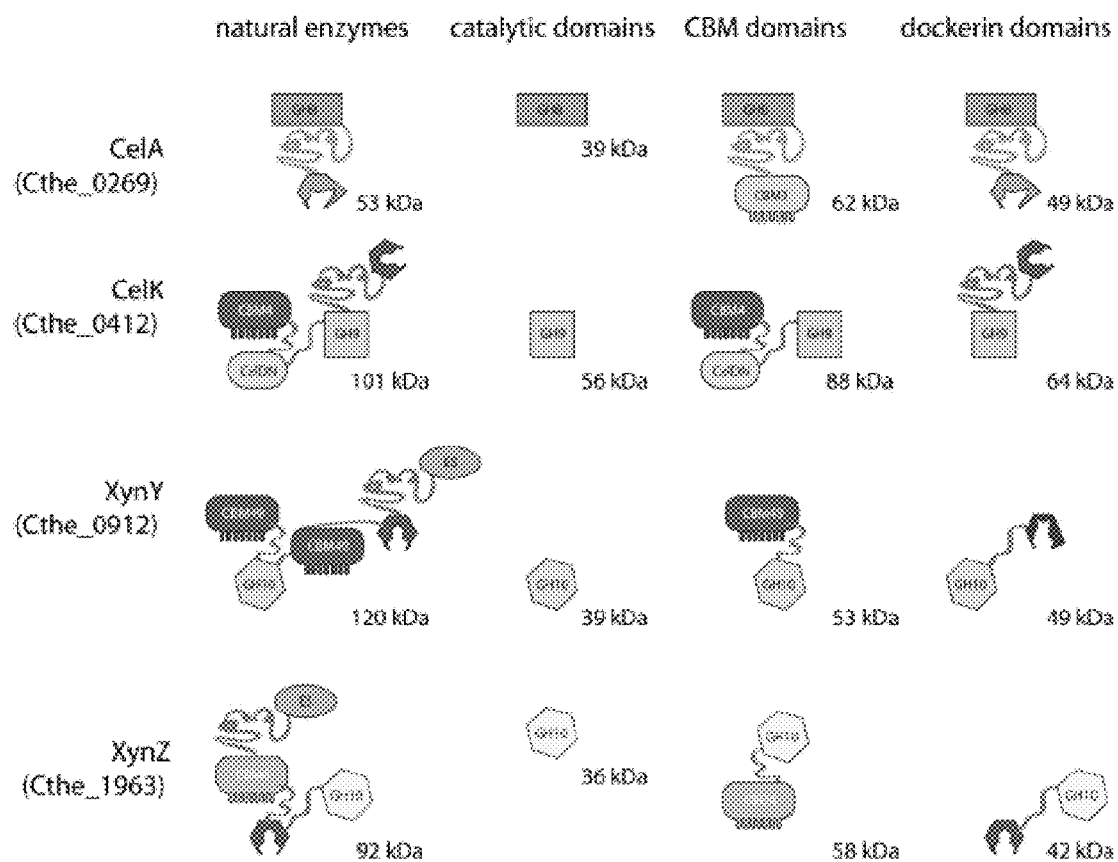
FIG. 16 includes schematic representations of the complete enzyme structure, the catalytic domains, the CBM (cellulose binding module) domains, and dockerin domains of the polypeptides coded by the CelA gene, the CelK gene, the XynY gene, and the XynZ gene of Clostridium thermocellum.
Figure 17:
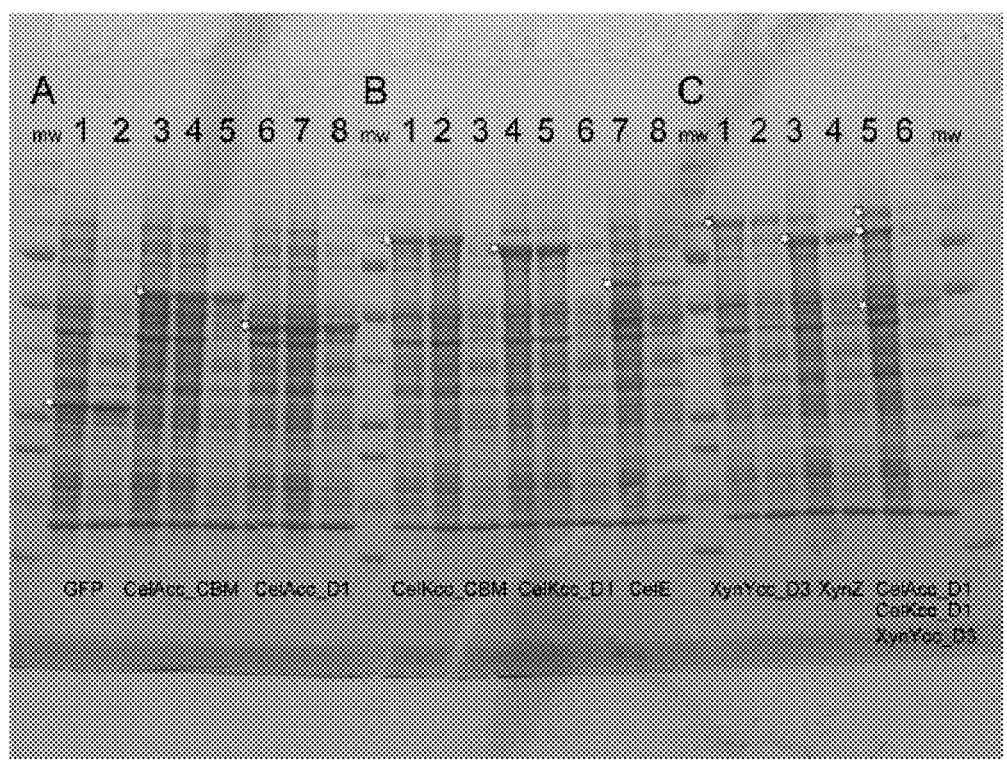
FIG. 17 is an SDS-PAGE analysis of cell-free translation results using various natural cellulolytic enzymes, fusion proteins, and fusion protein combinations.

FIG. 14 shows results from one embodiment of the present invention, where CelA and XynY were produced as fusions to dockerin domain, and were found to be capable of the deconstruction of AFEX-treated corn stover in the presence of Sca1. In another separate, preferred embodiment, CelA was produced as a fusion to dockerin, and XynZ was produced with the vector shown in FIG. 4. CelA and XynZ were found to have enhanced capacity for the deconstruction of AFEX-treated corn stover. This result demonstrates the utility of the present invention for identifying improved enzymes, and combinations thereof, for biomass deconstruction. In preferred embodiments, CelA refers to the protein product of Cthe_0269 gene from *Clostridium thermocellum*; CelK refers to the protein product of the Cthe_0412 gene from *Clostridium thermocellum*; XynZ refers to the protein product of the Cthe_1963 gene from *Clostridium thermocellum*; XynY refers to the protein product of the Cthe_0912 gene from *Clostridium thermocellum*. See FIG. 16 for a schematic drawing of these protein products and their included catalytic domains, CBM domains, and dockerin domains FIG. 17 shows an SDS-PAGE analysis of cell-free translation results for cellulolytic enzymes in different formats used in this invention. Lanes marked mw contain molecular weight markers. Expressed proteins of interest are marked with a star. Panel A shows expression of CelAcc. Lanes 1 and 2 show expression of a control protein. Lanes 3, 4, and 5, show expression of CelAcc_CBM, a fusion protein consisting of the catalytic core of CelA, a linker, and CBM3 from CipA. Lanes 6, 7, and 8 show expression of CelAcc_D1, a fusion protein consisting of the catalytic core of CelA, a linker, and D1. Panel B shows expression of CelKcc and CelE. Lanes 1, 2, and 3 show expression of CelKcc_CBM, a fusion protein consisting of the catalytic core of CelK, a linker, and CBM3 from CipA. Lanes 4, 5, and 6 show expression of CelKcc_D1, a fusion protein consisting of the catalytic core of CelK, a linker, and D1. Lanes 7 and 8 show expression of CelE as a natural enzyme. Panel C shows expression of XynYcc_D3, XynZ, and the simultaneous expression of CelAcc_D1, CelKcc_D1, and XynYcc_D3. Lanes 1 and 2 show expression of XynYcc_D3, a fusion protein consisting of the catalytic core of XynY, a linker, and D3. Lanes 3 and 4 show expression of XynZ as a natural enzyme. Lanes 5 and 6 show simultaneous expression of CelAcc_D1, CelKcc_D1, and XynYcc_D3.

In some embodiments of the present invention, expression plasmids are designed to facilitate simultaneous transfer of genes encoding all putative cellulose deconstruction enzymes into wheat germ cell-free and *E. coli* expression systems. For example, this capability can be obtained by incorporation of the FlexiVector cloning system (Promega, Madison, Wis.) into practice of the present invention. Other systems reported for the study of cellulose deconstruction do not permit this level of combinatorial assembly because of deficiencies in the cloning systems used.

In one embodiment of the present invention, the thermophilic bacterium *Clostridium thermocellum* (*C. thermocellum*) is used to apply this combinatorial approach to the discovery of enzymes and proteins. For example, it is possible to impart thermostability in fusion polypeptides by using *Clostridium thermocellum* proteins as domains. This design decision allows testing of target polypeptides isolated from thermophilic organisms as well as from organisms from more temperate environments.

The present invention facilitates high-throughput and combinatorial examination of existing, newly discovered, and engineered versions of enzymes capable of cellulose degradation. Thus, in one aspect, a platform is provided for the combinatorial assessment of enzymes and proteins from new genomes that are capable of cellulose deconstruction or of modulating biomass transformation. As genomes from a variety of known and newly identified organisms are sequenced and the genome sequence data becomes publicly available, it will be possible to utilize the compositions and methods of the present invention with a variety of organisms, including but not limited to: *Cellulomonas fimi* ATCC 484; *Cellvibrio gilvus* ATCC 13127; *Dictyoglomus turgidum* ATCC DSM 6724; *Ruminococcus albus* 7; *Ruminococcus albus* 8; *Bacillus* sp. ATCC 21833; *Fibrobacter succinogenes* S85 ATCC 19169; *Geobacillus* sp. strain C56-T3; *Geobacillus stearothermophilus* C56-N21_PLASMID; *Geobacillus thermoglucosidasius* strain C56-YS93; *Paenibacillus elgii* strain C56-YS68; *Streptomyces flavogriseus* ATCC 33331; Compost thermophile 3; ant pile organisms; *Anaerocellum thermophilum* DSM 6725; and others organisms are described at the US Department of Energy Joint Genome Institute, and at other similar genomic information databases.

In some embodiments of the present invention, the compositions and methods provide a cell-free, plasmid-clone independent way to test different combinations of targeted polypeptides (e.g., enzymes), preferably without requiring purification and assembly, preferably without refolding of some of the proteins from inclusion bodies, and other undesirable, time consuming steps. This embodiment follows the path of FIG. 1, steps 1, 2, 5, 6, and 7.

In other embodiments of the present invention, when the expressed systems are assembled, it is possible to remove one or more parts of the native gene (such as signal sequences, other domains) that might not be needed in the enzymatic assays that are targeted. For example, in the polypeptide designated CelAcc, "cc" means that only the catalytic core is used, instead of the whole CelA gene.

The methods described herein allow investigation of combinations of known genes from known genomes (standard biochemistry and enzymology), unknown genes from known genomes (proteomics), known genes from unknown genomes (metagenomics) and unknown genes from unknown genomes (metagenomics). The methods described herein are useful for discovering any new gene products that enhance benchmark catalytic activities, such as the ones that are exemplified in FIG. 11, FIG. 12, FIG. 13, and FIG. 14. Thus, in some aspects the present invention allows for the discovery of other presently unknown xylanases, polysaccharide deacetylases, esterases, arabinosidases, mannosidases, beta glycosidases, cellulose binding modules, cellulose binding domains, glycohydrolase family enzymes, pectinases, chitinases, lipases, swollenins, and the like. A survey of the scope of available genes of interest, which can be assembled by a skilled worker in the field of bioinformatic analysis, can be found at protein databases publicly accessible at a multitude of websites, including but not limited to the CaZY, Pfam, Swiss-Prot, and UniProt websites.

The methods described herein directly assess biomass deconstruction. By contrast, the complications of alternative assessment methods, such as substituting small molecule analogs for natural cellulose polymers, have been noted in the art. For example, faulty identification of enzymes capable of reacting with the non-natural analogs but subsequently found incapable of reacting with biomass substrates has been noted. The present invention avoids this failure of process in favor of direct studies of products derived from natural biomass, thus representing a transformative approach relative to the indirect use of small molecule substrate analogs typical of other biomass discovery work.

The invention encompasses enzyme discovery efforts that will be specifically undertaken for each new type of biomass under study. For example, switchgrass deconstruction will require discovery of a different set of enzymes than corn stover or poplar wood. Moreover, ammonia-fiber explosion (AFEX)-treated corn stover will respond to enzymatic deconstruction in a different manner than dilute acid-treated corn stover or alkaline peroxide-treated corn stover due to differences in the structural modifications produced in the treated biomass. In addition, biomass transformation includes other processes that are not exclusively deconstructive, as, for example, the processing of animal feed to optimize feed utilization, which would require yet a different combination of enzymes. The method may be used to discover specific enzyme compositions specific to each type of desired biomass substrate or each type of desired biomass transformation.

In one example, FIG. 11 illustrates the utility of the discovery platform of the present invention, applied to the deconstruction of phosphoric acid-treated cellulose. The graphs show one embodiment of the deconstruction reaction given by the example target polypeptides CelA and CelK separately produced by cell-free translation and then combined. This embodiment is compared with another embodiment of cellulose deconstruction given by simultaneous cell-free translation of CelA and CelK, also giving cellulose deconstruction. The results of FIG. 11 demonstrates that: 1) the two genes are simultaneously converted into catalytically active enzymes by the cell-free translation reaction; 2) the desired soluble sugar products are stable indefinitely in the non-living system, a situation that will not be true in living systems; 3) the product analysis can be done by HPLC (slow but conclusive), by optical methods (fast and amenable to high-throughput), or by fluorescence (also fast and amenable to high-throughput, but ~100-1000-fold more sensitive than the other methods); and 4) no laborious protein purification is needed because there is no existing biomass deconstruction activity present in the cell-free lysate.

FIG. 12 illustrates the utility of the discovery platform of the present invention, applied to the deconstruction of phosphoric acid-treated cellulose and the influence of an exogenously added protein. The graphs show one embodiment of cellulose deconstruction given by simultaneous cell-free translation of CelA and CelK, giving cellulose deconstruction. This is same result as shown in FIG. 11. In this additional embodiment, the same cell-free translation of CelA and CelK was performed with the addition of Sca2 expressed in *E. coli*, purified, and added to the assay of the cell-free translation reaction mixture. This exogenous protein was made in *E. coli* using vectors and an auto-induction protocol described in U.S. Patent Appl. Pub. No. 2008/0286749, which is herein incorporated by reference.

FIG. 13 shows HPLC analysis of the accumulation of soluble sugars from 96 h cellulose deconstruction reactions, whose complete time course is shown in FIGS. 11 and 12. In these reactions, it is clear that the combination of CelA, CelK and Sca2 has substantially increased capability for cellulose deconstruction relative to the other permutations lacking Sca2.

In another instructive embodiment of the present invention, FIG. 14 shows the simultaneous cell-free translation of CelA containing a fused dockerin domain and XynY, containing a different fused dockerin domain. The two translated proteins were found to catalyze the deconstruction of AFEX-treated corn stover without purification in the presence of exogenous Sca1. In a further embodiment of the present invention, substitution of XynZ prepared by cell-free translation for XynY on an equimolar basis gave increased biomass deconstruction by improving the conversion of hemicellulose to xylobiose and xylose. In this manner, the power of combinatorial assembly inherent in the present invention is demonstrated.

In some embodiments, compositions, methods, and systems are provided that can be used as versatile tools for a cloning process that allows testing of new genes in many contexts for improvements in biomass deconstruction. An example of a system for the deconstruction of a desired type of biomass (e.g. cellulose) includes a minimal set of: (i) one cohesin domain that is attached to one polypeptide that includes a biomass (e.g. cellulose) binding domain; and (ii) a target or desired polypeptide that is attached to a dockerin domain specific for said cohesin domain. The cohesin domain and the biomass (e.g. cellulose) binding domain may be expressed as a fusion protein, with or without linker between them. The target or desired polypeptide and the dockerin domain may be expressed as a fusion protein, with or without linker between them. The expressed cohesin domain and the expressed dockerin domain are specific for each other, so that they associate, i.e. interact with each other (as in a scaffoldin). The function of the expressed target polypeptide may be known or unknown. The expressed target polypeptide may have a biological activity (e.g. enzymatic activity) that is specific for the same type of biomass (e.g. cellulose). Alternatively, or in addition, the expressed target polypeptide may have a biological activity (e.g. enzymatic activity) that is specific for the different type of biomass (e.g. hemicellulose). Any number of cohesin domains, cohesin domain::biomass binding domain fusions, dockerin domains, and dockerin domain::target polypeptide fusions, may also be used in a variety of embodiments of the present invention. As well, a variety of biomass types can be used in the practice of the present invention, including but not limited to cellulose, hemicellulose, lignin, pectin, starch, chitin etc.

In some aspects of the invention, cell-free translation and in vitro assays for discovery of new cellulose deconstruction enzymes and proteins are included. According to this invention, the best candidate genes can then be easily transferred from cell-free discovery to cell-based expression systems for further research and use. Finally, the compositions and methods of the present invention can be easily linked to proven methods for making large quantities of enzymes, e.g. in *E. coli* using vectors and an auto-induction protocol described in U.S. Patent Appl. Pub. No. 2008/0286749, which is herein incorporated by reference.

A variety of expression vectors may be used for protein expression in *E. coli*, insect, yeast, or mammalian cells or in cell-free systems. Expression vectors that may be used for *E. coli* expression include, but are not limited to, the Gateway® Destination vectors (Invitrogen, Carlsbad, Calif.), pQE-30, pQE-40, and pQE-80 series (Qiagen, Valencia, Calif.), pUC19 (Yanisch-Perron et al., 1985, *Gene* 33: 103-119), pBluescript II SK+ (Stratagene, La Jolla, Calif.), the pET system (Novagen, Madison, Wis.), pLDR20 (ATCC 87205), pBTrp2, pBTac1, pBTac2 (Boehringer Ingelheim Co., Ingelheim, Germany), pLSA1 (Miyaji et al., 1989, *Agric. Biol. Chem.* 53: 277-279), pGEL1 (Sekine et al., 1985, *Proc. Natl. Acad. Sci. USA.* 82: 4306-4310), and pSTV28 (manufactured by Takara Shuzo Co., Japan). When a yeast strain is used as the host, examples of expression vectors that may be used include pYESTDES52 (Invitrogen), YEp13 (ATCC 37115), YEp24 (ATCC 37051), and YCp50 (ATCC 37419). When insect cells are used as the expression host, examples of expression vectors that may be used include pVL1393 (BD Biosciences, Franklin Lakes, N.J.) and pIEX (Novagen). When wheat germ cell-free translation is used, examples of expression vectors that may be used include pEU (Cell-Free Sciences, Yokohama, Japan), or derivatives such as pEU-His-FV. When *E. coli* cell-free translation is contemplated for use, examples of expression vectors that may be used include pET and others described above.

EXAMPLES

It is understood that the examples and embodiments described herein are for illustrative purposes, only and that various modifications or changes in light thereof will be suggested to persons skilled in the art and are to be included within the spirit and purview of this application and scope of the appended claims. It is also to be understood that the terminology used herein is for the purpose of describing particular embodiments only, and is not intended to limit the scope of the present invention, which is limited only by the claims. The following examples are offered to illustrate, but not to limit the claimed invention.

Example 1

Gene Cloning

Figure 15:
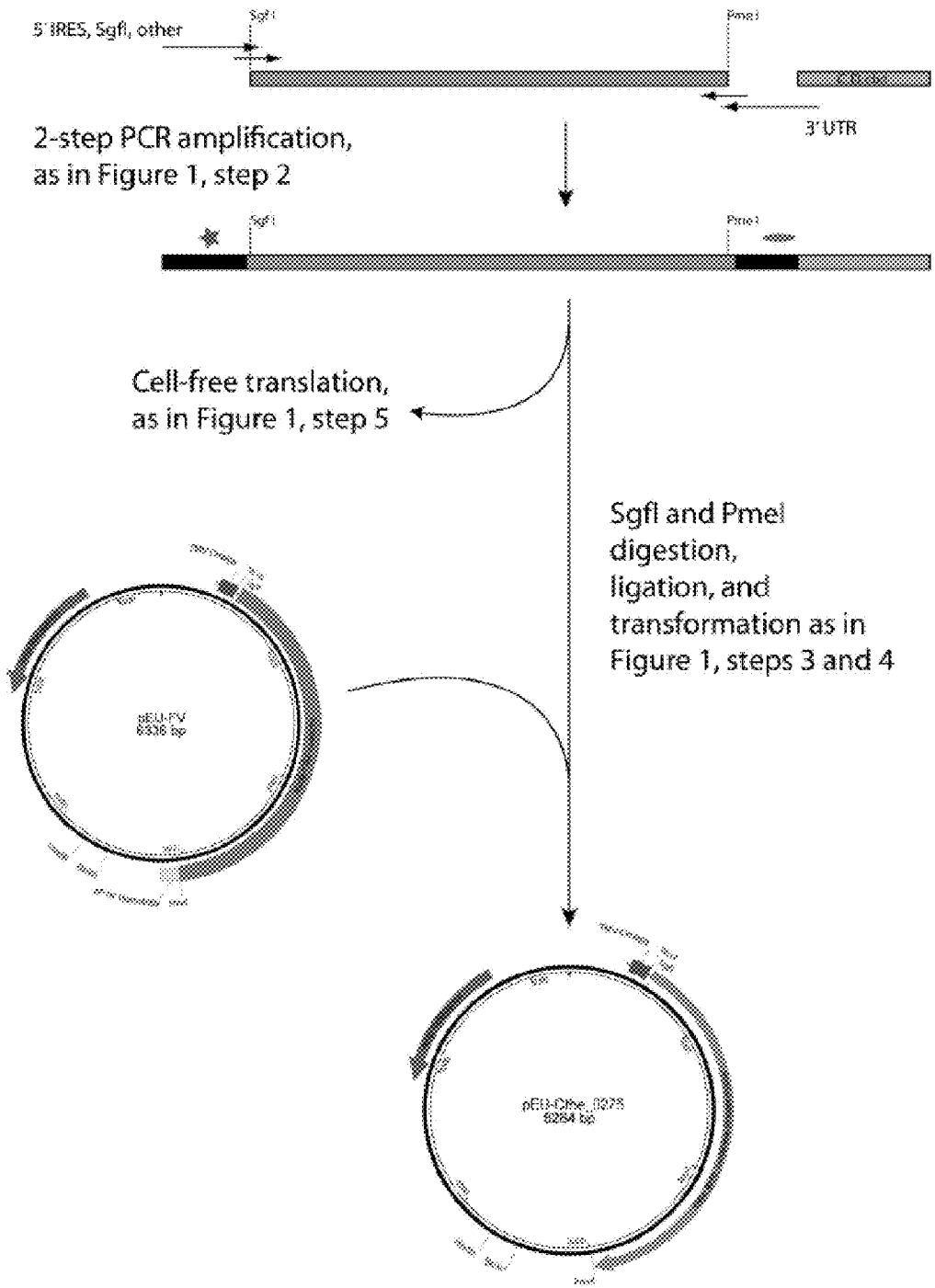
FIG. 15 is a schematic representation of cloning methods used to prepare genes for either vector free cell-free translation or for transfer into plasmid vectors for either cell-free or E. coli expression. The example enzyme gene Cthe_0275 from Clostridium thermocellum.

A 2-step PCR method was employed (see FIG. 15). The first step included matching the gene, and adding 5' SgfI and 3' PmeI. PCR primer design can be used to append a 5' internal ribosome entry sequence and a 3'-untranslated region to enhance cell-free translation. This assembly permits expression testing in cell-free translation without intermediate cloning into plasmid vectors. The second step includes cloning the gene into a compatible, engineered vector using the FlexiVector cloning system (Promega) and toxic (SacB) counter-selection.

TABLE 1

Examples of compositions of scaffoldin proteins used herein

| Abbreviation | Gene Locus | GenBank | Modular Structure | Plasmid Name |
|---|---|---|---|---|
| CipA | Cthe_3077 | L08665 | $(C1)_2$-CBM3-$(C1)_{11}$-$X_2$-D2 | |
| Sca1 | | | (C1)-CBM3-(C2)-(C3) | pEC-Sca1 |
| Sca2 | | | (C1)-CBM3 | pEC-Sca2 |
| Sca3 | | | CBM3-(C2) | pEC-Sca3 |
| Sca4 | | | (C1)-CBM3-(C2) | pEC-Sca4 |

Footnotes:
C1 is prepared from the second type 1 cohesin domain occurring in Cthe_3077.
C2 is an engineered isoform of type 1 cohesin prepared as indicated herein, from the second type 1 cohesin domain occurring in Cthe_3077.
C3 is prepared from the type 2 cohesin domain occurring in Cthe_1307.
CMB3 is the cellulose-binding module 3 occurring in Cthe_3077.
D2 is the natural type 2 dockerin found in CipA.

Table 2 lists vectors that incorporate *C. thermocellum* dockerin sequences. The different pDock vectors (e.g., pEC-D1, pEU-D1, and others) create fusions of a protein of interest with a unique dockerin at the C-terminus. The dockerins localize the expressed fusion proteins to the corresponding unique cohesins in the artificial scaffoldins. In the cell-free translation reaction, this combination along with the inclusion of cellulose can impart stability to the newly translated protein complex that cannot be achieved from use of living expression hosts.

The pDock vectors use FlexiVector™ (Promega, Madison, Wis.) to allow high-throughput cloning of genes. After sequence verification, the verified gene can be transferred in vitro to many different expression contexts, including cell-free translation and other cell-based systems. The same PCR product can be used for clone-free cell-free translation studies, or can be cloned into pEC-D1, pEC-D2, pECD3 or others. This cloning strategy has the distinct advantage of requiring only one nucleotide sequence verification before subsequent high-fidelity transfer of the verified gene to many other research contexts. The design principles for creation of compatible vectors for bacterial, cell-free, yeast, and insect cell expression systems have been previously reported in the art.

TABLE 2

Examples of dockerin domains used herein

| Vector | Protein designation | Description |
|---|---|---|
| pEU_SBC_D1 | Target-D1 | Creates a Target-D1 fusion; D1 binds to C1 indicated in Table 1. |
| pEU_SBC_D2 | Target-D2 | Creates a Target-D2 fusion; D2 binds to C2 indicated in Table 1. |
| pEU_SBC_D3 | Target-D3 | Creates a Target-D3 fusion; D2 binds to C3 indicated in Table 1. |

Footnotes.
D1 is prepared from the dockerin domain occurring in Cthe_0912.
D2 is an engineered isoform of dockerin prepared as indicated herein, occurring in Cthe_0912.
D3 is prepared from the type 2 dockerin domain occurring in Cthe_3077.

Example 2

Expression and Purification of Sca1

Expression. *E. coli* BL21 cells were transformed with the expression plasmid pSca1 and scaled up for protein production in terrific broth supplemented with 0.5% w/v glucose and 50 µg/mL kanamycin. The expression culture consisted of terrific broth supplemented with 0.025% w/v glucose, 0.8% w/v glycerol, 0.5% w/v lactose, and 0.375% w/v succinic acid. Cultures were incubated with constant shaking at 30° C. for 24 hours before harvest.

Purification. *E. coli* expressing Sca1 were resuspended in 2 mL/g purification Buffer A (25 mM HEPES pH 7.2, 500 mM NaCl, 40 mM imidazole, 2 mM $CaCl_2$ and lysed by sonication. After clarification by centrifugation, supernatant was loaded onto an IMAC affinity column equilibrated in purification Buffer A. After loading, the column was washed with 1 column volume of Buffer A followed by a linear gradient of 6 column volumes from 100% Buffer A to 100% Buffer B (Buffer A+460 mM imidazole). Fractions containing Sca1 were identified by SDS-PAGE, pooled, concentrated and frozen.

Example 3

Expression and Purification of Sca2

Expression. *E. coli* BL21 cells were transformed with the expression plasmid pSca2 and scaled up for protein production in terrific broth supplemented with 0.5% w/v glucose and 50 µg/mL kanamycin. The expression culture consisted of terrific broth supplemented with 0.025% w/v glucose, 0.8% w/v glycerol, 0.5% w/v lactose, and 0.375% w/v succinic acid. Cultures were incubated with constant shaking at 30° C. for 24 hours before harvest.

Purification. *E. coli* expressing Sca2 were resuspended in 2 mL/g purification Buffer A (25 mM HEPES pH 7.2, 500 mM NaCl, 40 mM imidazole, 2 mM $2CaCl_2$ and lysed by sonication. After clarification by centrifugation, supernatant was loaded onto an IMAC affinity column equilibrated in purification Buffer A. After loading, the column was washed with 1 column volume of Buffer A followed by a linear gradient of 6 column volumes from 100% Buffer A to 100% Buffer B (Buffer A+460 mM imidazole). Fractions containing Sca2 were identified by SDS-PAGE, pooled, concentrated and frozen.

Example 4

Expression and Purification of BglA

Expression. *E. coli* BL21 cells were transformed with the expression plasmid pEC_BglA and scaled up for protein production in terrific broth supplemented with 0.5% w/v glucose and 50 µg/mL kanamycin. The expression culture consisted of terrific broth supplemented with 0.025% w/v glucose, 0.8% w/v glycerol, 0.5% w/v lactose, and 0.375% w/v succinic acid. Cultures were incubated with constant shaking at 30° C. for 24 hours before harvest.

Purification. *E. coli* expressing BglA were resuspended in 2 mL/g purification Buffer A (25 mM HEPES pH 7.2, 500 mM NaCl, 40 mM imidazole, 2 mM $CaCl_2$ and lysed by sonication. After clarification by centrifugation, supernatant was loaded onto an IMAC affinity column equilibrated in purification Buffer A. After loading, the column was washed with 1 column volume of Buffer A followed by a linear gradient of 6 column volumes from 100% Buffer A to 100% Buffer B (Buffer A+460 mM imidazole). Fractions containing BglA were identified by SDS-PAGE, pooled, concentrated and frozen.

TABLE 3

Data from the expression and purification of Sca1, Sca2, Sca3, and BglA Polypeptides

| Enzyme | Culture (L) | Cell Paste (g) | Purified Protein (mg) | Yield (mg/L) | Activity (U/mg) |
|---|---|---|---|---|---|
| Sca1 | 1 | 25 | 400 | 400 | n.a. |
| Sca2 | 4 | 44 | ~600 | 150 | n.a. |
| Sca3 | 4 | 56 | ~800 | 200 | n.a. |
| BglA | 4 | 25.4 | ~50 | 12 | $1^c$ |

Example 5

Proteins Studied

Table 1 lists examples of vectors that incorporate *C. thermocellum* cohesin and cellulose binding domains. FIG. 7 shows a vector used for expression in *E. coli* of a fusion protein Sca1, which comprises a type 1 cohesin domain C1, a linker region L1, a cellulose binding module CBM3, another linker region L2, a cohesin isoform domain C2, a linker region L3, and a type 2 cohesin domain C3. Likewise, Sca2 comprises a type 1 cohesin domain C1, a linker region L1, and a cellulose binding module CBM3; Sca3 comprises a cellulose binding module CBM3, a linker region L2, and a cohesin isoform domain C2; while Sca4 comprises a type 1 cohesin domain C1, a linker region L1, a cellulose binding module CBM3, another linker region L2, and a cohesin isoform domain C2 (see FIG. 8).

As demonstrated elsewhere, it is possible to express these engineered proteins in *E. coli* and purify them using standard chromatographic methods. It is possible to add this purified protein to an assay of a cell-free translation and alter the catalytic performance, as shown by FIG. 12.

In embodiments described herein, it is possible to co-express the protein domains described herein (cohesins, dockerins) along with any other desired target polypeptides using cell-free translation. The simultaneous translation can act to stabilize target polypeptides containing dockerin domains, providing an unexpected advantage to the use of Sca1, Sca2, Sca3, or Sca4 constructs. The stability can be further enhanced by inclusion of cellulose in the cell-free translation reaction, which does not inhibit the protein synthesis reaction as indicated in FIG. 10.

FIG. 10 shows an SDS-PAGE analysis that cellulose can be added to the cell-free translation reaction without inhibiting the protein synthesis reaction. Lane 1 contains molecular weight markers. Lane 2 shows protein synthesis of a control protein using cell-free translation. Lane 3 shows protein synthesis of the same control protein performed in the presence of 2% w/v of Sigmacel, a commercial cellulose preparation. There is no difference in the level of control protein expressed in either lanes 2 or 3. All other protein bands are endogenous bands of the wheat germ extract used for cell-free translation.

Tables 4A and 4B shows examples of genes from *C. thermocellum* that can be used in the practice of the present invention, many of which were used in the Examples that follow. Results obtained from study of these target polypeptides can then be compared to results obtained with future enzyme assemblies.

TABLE 4A

Examples of *Clostridium thermocellum* genes that can be used in the practice of the present invention

| NCBI GeneID | gene_locus | Abbreviation | Protein name |
|---|---|---|---|
| 4808552 | Cthe_0269 | CelA | glycoside hydrolase family protein |
| 4808415 | Cthe_0412 | CelK | glycoside hydrolase family protein |
| 4810533 | Cthe_0912 | XynY | endo-1,4-beta-xylanase |
| 4810746 | Cthe_1963 | XynZ | glycoside hydrolase family protein |
| 4808805 | Cthe_0040 | CelI | cellulose 1,4-beta-cellobiosidase |
| 4808416 | Cthe_0413 | CbhA | glycoside hydrolase family 9 protein |
| 4811137 | Cthe_2989 | Cdp | Cellodextrin phosphorylase |
| 4808558 | Cthe_0275 | Cbp | Cellobiose phosphorylase |
| 4808630 | Cthe_0212 | BglA | Beta-glucosidase |

TABLE 4B

*C. Thermocellum* Enzyme Variants Produced by Cell-Free Translation

| *Clostridium thermocellum* Enzyme variants produced by cell-free translation | | | Wheat germ vectors | | | | | E. coli vectors | | | | |
|---|---|---|---|---|---|---|---|---|---|---|---|---|
| abbrv | gene_locus | Protein Name | native | cc | cc_CBM | cc_D1 | oc_D3 | native | cc | cc_CBM | cc_D1 | cc_D3 |
|  | Cthe_0032 | putative mannnase |  | x |  | x |  | x |  |  |  |  |
| CelI | Cthe_0040 | cellulose 1-4-beta-cellobiosidase |  |  |  |  | x | x |  | x | x | x |
| LlcB | Cthe_0211 | Bchenase |  |  | x |  |  |  |  | x |  |  |
| BglA | Cthe_0212 | cellobiase | x |  |  |  |  | x |  |  |  |  |
| CelA | Cthe_0269 | endoglucanase A | x |  | x | x |  | x | x | x | x |  |
| ChlA | Cthe_0270 | glucoside hydrolase family 18 protein |  | x | x |  |  | x |  |  |  |  |
|  | Cthe_0271 | unknown protein | x |  |  |  |  | x |  |  |  |  |
| Cbp | Cthe_0275 | cellobiose phosphorylase |  |  |  |  |  | x |  |  |  |  |
|  | Cthe_0399 | unknown protein | x |  |  |  |  | x |  |  |  |  |
| CelL | Cthe_0405 | glycoside hydrolase family 5 protein |  |  | x |  | x | x |  | x |  |  |
| CelK | Cthe_0412 | cellulose 1,4-beta-cellobiosidase | x | x | x | x |  | x | x | x |  |  |
| CbhA | Cthe_0413 | glycoside hydrolase family 9 protein | x | x |  |  |  | x |  | x |  |  |
|  | Cthe_0433 | glycoside hydrolase family 9 protein |  |  |  |  |  |  |  |  |  |  |
| CelB | Cthe_0536 | glycoside hydrolase family 5 protein |  |  |  |  |  |  |  |  |  |  |
| CelF | Cthe_0543 | glycoside hydrolase family 9 protein |  |  |  |  |  |  |  |  |  |  |
| CelR | Cthe_0578 | glycoside hydrolase family 9 protein |  | x | x |  |  |  | x |  |  |  |
| CelJ | Cthe_0624 | glycoside hydrolase, family 9-like Ig-like |  |  |  |  |  |  |  |  |  |  |
| CelQ | Cthe_0625 | glycoside hydrolase family 9 protein |  |  |  |  |  |  |  |  |  |  |
|  | Cthe_0640 | putative pectinase |  | x | x |  |  | x |  |  |  |  |
|  | Cthe_0736 | cellulosome anchoring protein, cohesin region |  |  |  |  |  |  |  |  |  |  |
| CelW | Cthe_0745 | glycoside hydrolase family 9 protein |  |  |  |  |  |  |  |  |  |  |
| CelE | Cthe_0797 | glycoside hydrolase family 5 protein | x |  | x |  |  | x | x | x | x |  |
|  | Cthe_0821 | unknown protein |  | x | x |  |  | x |  |  |  |  |
| XynY | Cthe_0912 | endo-1,4-beta-xylanase Y |  | x | x |  | x | x | x | x |  | x |
| BglB | Cthe_1256 | cellobiase |  |  |  |  |  | x |  |  |  |  |

TABLE 4B-continued

*C. Thermocellum* Enzyme Variants Produced by Cell-Free Translation

| *Clostridium thermocellum* Enzyme variants produced by cell-free translation | | | Wheat germ vectors | | | | | E. coli vectors | | | | |
|---|---|---|---|---|---|---|---|---|---|---|---|---|
| abbrv | gene_locus | Protein Name | native | cc | cc_CBM | cc_D1 | oc_D3 | native | cc | cc_CBM | cc_D1 | cc_D3 |
| PGM | Cthe_1265 | phosphoglucomutase | | | | | | | | | | |
| | Cthe_1271 | CBM6, GH43 | | | | | | | | | | |
| | Cthe_1273 | unknown protein | x | | | | | x | | | | |
| XghA | Cthe_1398 | cellulosome enzyme, dockerin type I | | x | x | | | | x | | | |
| | Cthe_1400 | glycosyl hydrolase 53 | | | | | | | | | | |
| XynC | Cthe_1838 | glycoside hydrolase family 10 protein | | x | x | | | | x | | | |
| XynZ | Cthe_1963 | endo-1,4-beta-xylanase Z | x | | | | | x | | x | | |
| CelS | Cthe_2089 | endo-1,4-beta-glucanase | | x | | x | | x | | x | x | |
| | Cthe_2193 | CBM6, GH5 | | | | | | | | | | |
| Ara | Cthe_2548 | Alpha-arabinofuranosidase | | | | | | | | | | |
| | Cthe_2590 | glycoside hydrolase family 10 protein | | | | | | | | | | |
| LecA | Cthe_2761 | glycoside hydrolase family 9 protein | | x | x | | | x | | | | |
| ManB | Cthe_2811 | glycoside hydrolase family 26 protein | | | | | | | | | | |
| CelT | Cthe_2812 | glycoside hydrolase family 9 protein | | | | | | | | | | |
| CelG | Cthe_2872 | endo-1,4-beta-glucanase G | | x | | | x | x | | x | | |
| GK | Cthe_2938 | glucokinase | x | | | | | | | | | |
| Cdp | Cthe_2989 | cellodextrin phosphorylase | | | | | | x | | | | |
| ClpA | Cthe_3077 | cellulosome anchoring protein cohesin region | | | | | | x | | | | |
| Sca1 | Cthe_3077.1 | artificial scaffolding prepared from CipA | | | | | | x | | | | |
| Sca2 | Cthe_3077.2 | artificial scaffolding prepared from CipA | | | | | | x | | | | |
| Sca3 | Cthe_3077.3 | artificial scaffolding prepared from CipA | | | | | | x | | | | |
| Sca4 | Cthe_3077.4 | artificial scaffolding prepared from CipA | | | | | | x | | | | |

Example 6

Substrates

Different types of substrates for carrying out the reactions and analysis can be used. These include, but are not limited to, glucose, glucose-1-phosphate, glucose-6-phosphate, arabinose, mannose, xylose, cellobiose, xylobiose, cellotriose, cellotetraose, MUC, MUX, phosphoric acid swollen cellulose, DMSO/$SO_2$ treated amorphous cellulose, crystalline cellulose, carboxymethyl cellulose, Avicell, or Blue cellulose. These above substrates can be purchased or prepared from commercial materials as described below. In additional, natural biomass materials include corn stover (ground to 5 mm or 1 mm particle size; untreated or AFEX-treated), switchgrass (ground to 5 mm or 1 mm particle size; untreated or treated), poplar, sugarcane, *Brachipodia*, or biomass prepared from other species, such as, for example, animal feed.

In some preferred embodiments, cellulose substrates are prepared by phosphoric acid treatment and DMSO/$SO_2$ treatment. Preparation of amorphous cellulose by the conventional phosphoric acid method causes cleavage of the polymer, thus producing strands of varying degrees of polymerization. This treatment may facilitate the detection of certain classes of deconstruction enzymes. Solubilizing crystalline cellulose by DMSO/$SO_2$ treatment does not cause chain cleavage and thus no additional reducing ends are produced. This treatment may facilitate the detection of certain classes of deconstruction enzymes.

Phosphoric acid-swelled cellulose was prepared by the method of Weimer et al., 1990, *Appl. Environ. Microbiol.* 56: 2421-2429. Sigmacell 50 microcrystalline cellulose (20 g, Sigma, St. Louis, Mo.) was swollen in 800 g of cold (0° C.) 80% phosphoric acid, with rapid stirring with a plastic rod. All samples were stirred for 1 h in an ice bath. After that time, the cellulose was diluted with 2 L of cold water, thoroughly mixed, and allowed to settle, after which the overlying liquid was removed by siphoning; this washing procedure was repeated several times to reduce the acid content. The cellulose slurries were then neutralized with solid $NaHCO_3$, rinsed, decanted as above, and then secured inside bags formed from nylon-reinforced paper toweling. These bags were filled with ~1 L of distilled water, and the excess liquid was squeezed off; this process was repeated 20 times. The bags were then sealed, suspended in buckets containing 5 L of cold deionized water, and dialyzed for 10 days, with frequent changes of water; prior to each change of water, the bags were tightly hand squeezed to facilitate removal of the equilibrated solutions. After completion of dialysis (when the phosphate content reached <1 μg/L) the cellulose was lyophilized.

Amorphous cellulose was prepared by a modification of the method of Isogai and Atalla, 1991, *J. Polymer. Sci.* A29: 113-119). Three g of fibrous crystalline cellulose CF-1 (Sigma) was vacuum dried to remove adsorbed water, swollen in 150 mL of DMSO for 1 h at 60° C. $SO_2$ in DMSO (6.75 mL containing 0.71 g $SO_2$/mL) was added, followed by 2.58 g of diethylamine, and the solution swirled briefly until complete solubilization was achieved (less than 1 min). The cellulose was regenerated by slowly pouring the solution into distilled water with rapid stirring. The regenerated amorphous cellulose was squeezed into a nylon mesh (30 μm)

screen to remove residual reactants. This process was repeated until the DMSO odor in the solids was almost completely removed. The solids were then washed with 2 L of deionized water, with filtration through the same nylon mesh screen in a Buchner funnel. The solids were resuspended in water, blended 1 min a Waring blender, and dialyzed (SpectraPor 1000 MWCO membrane, Spectrum, Rancho Dominguez, Calif.) for 3 d at 5° C., with frequent changes of water. After a final rinse, the amorphous cellulose was recovered by filtration and lypholized.

Example 7

Cell-Free Translation Methods and Results

Some examples of compositions, methods, and systems useful for cell free translation can be found in Michael A. Goren and Brian G. Fox, Protein Expression and Purification 62 (2008); 171-178, which is herein incorporated by reference. In general, the composition of the cell-free translation reaction is: pellet of mRNA prepared for a selected gene, 15 µL of wheat germ extract, 0.7 mg/mL of creatine kinase, RNAsin, 0.3 mM amino acids. The substrate (e.g., but not limited to amorphous cellulose, Avicel, natural corn stover, AFEX-treated corn stover, switchgrass, AFEX-treated switchgrass) is added at 2% w/v, i.e., 20 mg of cellulose per 1 mL of cell-free translation reaction. An individual cell-free translation reaction has a total volume of 50 µL.

FIG. 17 shows SDS-PAGE analysis of cell-free translation results for cellulolytic enzymes in different formats used in this invention. Lanes marked mw contain molecular weight markers. Expressed proteins of interest are marked with a star. Panel A, expression of CelAcc. Lanes 1 and 2, expression of a control protein. Lanes 3, 4, and 5, expression of CelAcc_CBM, a fusion protein consisting of the catalytic core of CelA, a linker, and CBM3 from CipA. Lanes 6, 7, and 8, expression of CelAcc_D1, a fusion protein consisting of the catalytic core of CelA, a linker, and D1. Panel B, expression of CelKcc and CelE. Lanes 1, 2, and 3, expression of CelKcc_CBM, a fusion protein consisting of the catalytic core of CelK, a linker, and CBM3 from CipA. Lanes 4, 5, and 6, expression of CelKcc_D1, a fusion protein consisting of the catalytic core of CelK, a linker, and D1. Lanes 7 and 8, expression of CelE as a natural enzyme. Panel C, expression of XynYcc_D3, XynZ, and the simultaneous expression of CelAcc_D1, CelKcc_D1, and XynYcc_D3. Lanes 1 and 2, expression of XynYcc_D3, a fusion protein consisting of the catalytic core of XynY, a linker, and D3. Lanes 4 and 5, expression of XynZ, as a natural enzyme. Lanes 5 and 6, simultaneous expression of CelAcc_D1, CelKcc_D1, and XynYcc_D3. This image illustrates the data from a cell-free translation gel. It shows expression of natural enzymes (CelE, XynZ), enzymes fused to a CBM (CelAcc and CelKcc), enzymes fused to different dockerins (CelAcc_D1 and XynYcc_D3). It also shows simultaneous expression of three enzymes (CelAcc_D1, CelKcc_D1, and XynYcc_D3).

Automated cell-free translation using, as a non-limiting example, the Protemist-DTII robot expression system (Cell-Free Sciences, Matsuyama Ehime, Japan) can be used with the methods and systems of the invention to allow for efficient high throughput testing of multiple combinations of target polypeptides. The DTII is optimized for wheat germ cell-free protein expression system, and can perform transcription, translation, and batch affinity purification unattended in a 24 hour plus cycle. A desktop DTII can run on either a 6-well format (×4 ml; transcription, translation, and purification) or a 24-well format (×1 ml; transcription and translation) to express up to 24 genes or gene combinations of interest. Other robots can be used to increase the throughput of protein expression. A stand alone Protemist100 can run on either a 8-well format (×4 ml; translation) or a 96 or 384-well format (×50 ul; transcription and translation) to express up to 384 genes or gene combinations of interest.

Figure 18A:
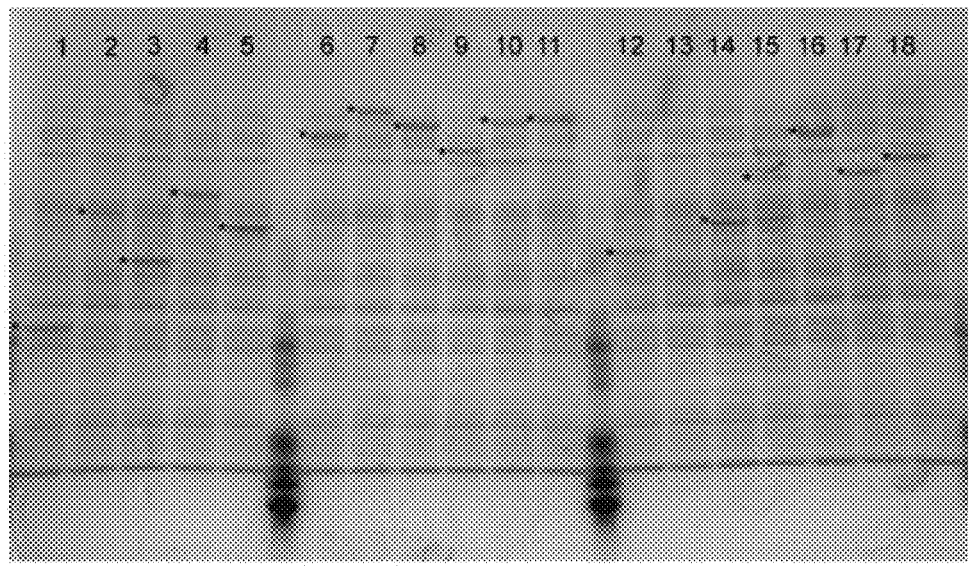
FIGS. 18A and 18B are SDS-PAGE analyses of cell-free translation results using various natural cellulolytic enzymes and fusion proteins in an automated DT-II system.
Figure 18B:
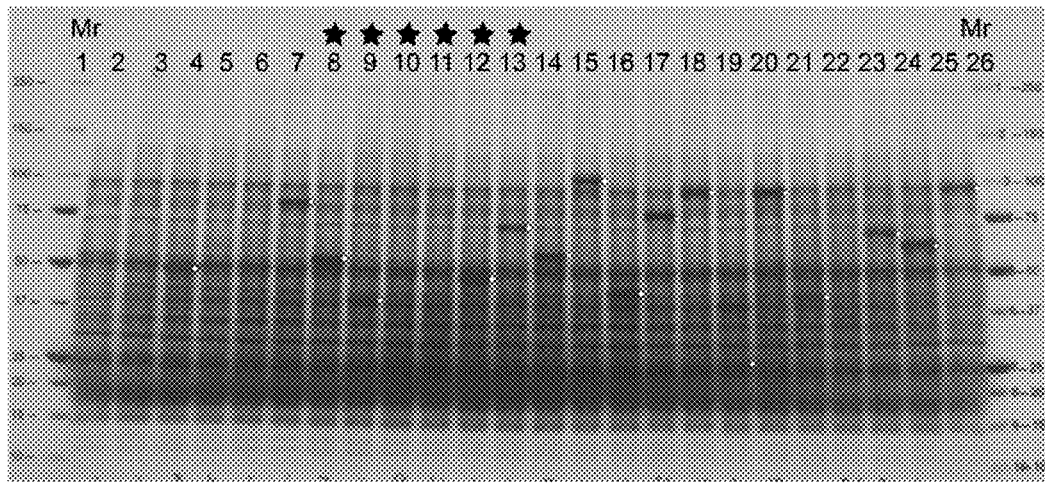

FIGS. 18A and 18b shows an SDS-PAGE analysis demonstrating the successful use of DTII in the cell-free expression of a number of different target polypeptides, including a number of the natural enzymes and fusion proteins discussed further herein. FIG. 18A shows the expression of 18 different polypeptides. Gel bands showing target polypeptide expression are designated by stars. Lane 1 shows the expression of the 28 kDa control GFP protein. Lane 2 shows the expression of the 50 kDa wild type CelA. Lane 3 shows expression of CelAcc (40 kDa), lane 4 shows expression of CelAcc_CBM (62 kDa), lane 5 shows expression of CelAcc_D1 (49 kDa), lane 6 shows expression of CelKcc (89 kDa), lane 7 shows expression of CelKcc_CBM (111 kDa), lane 8 shows expression of CelKcc_D1 (98 kDa), lane 9 shows expression of XynYcc (76 kDa), lane 10 shows expression of XynYcc_CBM (99 kDa), lane 11 shows expression of XynYcc_D3 (97 kDa), lane 12 shows expression of Cthe_0271 (31 kDa), lane 13 shows expression of Cthe_0399 (28 kDa), lane 14 shows expression of Cthe_0821 (51 kDa), lane 15 shows expression of wild type CelE, lane 16 shows expression of wild type XynZ, lane 17 shows expression of CelLcc_D3 (67 kDa), and lane 18 shows expression of CelGcc_D3 (72 kDa). Cthe_0271, Cthe_0399, and Cthe_0821 are encoded by genes annotated as hypothetical proteins, so this result shows the capability of cell-free translation for rapidly producing unknown proteins involved in biomass deconstruction.

FIG. 18B shows the expression of 25 different polypeptides, including 6 gene annotated hypotheticals (shown as stars at top of column). Lanes 1 and 26 show molecular weight reference markers. Lane 2 shows the expression of control GFP protein. Lane 3, Cbha; lane 4; CelA, lane 5, CelE, lane 6, CelK, lane 7, XynZ; lane 8, Cthe_0032; lane 9, Cthe_0271; lane 10; Cthe_0399; lane 11, Cthe_0640; lane 12, Cthe_0821: lane 13, Cthe_2761; lane 14, CelAcc_CBM; lane 15, CelKcc_CBM; lane 16, LicBcc_CBM; lane 17, XynCcc_CBM; lane 18, XynYcc_CBM; lane 19, CelAcc_D1; Lane 20, CelKcc_D1; lane 21, dsRed_D1; lane 22, GFP_D2; lane 23, CelGCcc_D3; lane 24, CelLcc_D3; lane 25, XynYcc_D3 50 kDa wild type CelA. Again, a number of the expressed proteins (Cthe_0032, Cthe_0271, Cthe_0821, Cthe_2761) are encoded by genes annotated as hypothetical proteins, so this result further shows the capability of cell-free translation for rapidly producing unknown proteins involved in biomass deconstruction.

In other embodiments, it is possible to express the Sca1, Sca2, Sca3, and Sca4 proteins either in *E. coli* or using cell-free expression.

Example 8

Cellulose Deconstruction Reactions and Assays

The assay conditions listed below, including pH, temperature, substrate loading, enzyme loading and duration, can be varied as necessary to optimize the assay for enzymes from varying sources. Conditions for the assay of *C. thermocellum* enzymes are described herein. The cell-free translation reaction is added to the cellulose deconstruction reaction at a volume ratio of 5 µL per mL for expression of a single gene or 10 µL per mL for simultaneous expression of two genes. Further scaling would proceed according to the number of additional genes translated. The buffer conditions are 100 mM citrate, pH 5.8, 2 mM EDTA, 7 mM $CaCl_2$, 5 mM cysteine, and 0.01% w/v azide. Substrate is added at a loading of 1% w/v. The reaction proceeds at 65° C. with constant shaking.

FIG. 11 illustrates one example of the utility of the discovery platform of the present invention, namely applied to the deconstruction of phosphoric acid treated cellulose. The graphs show glucose release as a function of time for deconstruction reactions given facilitated by the example target polypeptides CelA and CelK separately produced by cell-free translation, and for the combination of the two polypeptides after being separately produced. This result is compared with the measured cellulose deconstruction resulting from cellulose exposure to a cell-free system in which CelA and CelK are simultaneously cell-free translated. Both enzymes are active from cell-free translation.

The weak multi-phasic behavior shown in FIG. 11 is also observed in other studies. The nature of the products formed in the early rapid phase may provide important clues on how to increase the speed the deconstryction process. HPLC analysis, shown in FIG. 13, of the total products released during the time course of these experiments corroborates this result. Without being bound by any theory or algorithm, it is estimated that this experiment uses a ratio of 10 mg total protein (including components of the wheat germ extract) per g of cellulose substrate in the cell-free translation reactions. The cell-free translated enzymes represent less than 20% of the total protein in the cell-free lysate. Optionally, densitometry measurements can provide a more accurate estimate of enzyme present. It is further estimated 100% hydrolysis of the cellulose added to the cell-free translation reaction would yield about 50 mM glucose, so the above figure represents about 2% conversion. Assuming the cellulytic enzymes are ~20% of the total protein in the cell-free reaction, 2% conversion catalyzed by 2 mg of enzyme catalysts per 96 h is an efficiency of 1% per mg of total catalysts per 96 h ($1.0 \times 10^{2}$%/mg/h).

FIG. 12 is a graph showing measured glucose release as a function of time obtained from CelA/CelK co-translation (diamond outlines) and CelA/CelK co-translation in the presence of 1 µM of Sca2 (circle outlines). Sca2 is an artificial scaffoldin that the inventors designed and produced in *E. coli*. This combination of two enzymes and Sca2 gives ~5× the amount of glucose liberated, still with only two enzymes present in the same amounts as shown in FIG. 11. The result of FIG. 12 represents about 10% conversion. Assuming the two enzymes are present at 20% of the total lysate protein, 10% conversion catalyzed by 2 mg of enzyme catalysts is an efficiency of 5% conversion per mg of enzyme ($5.2 \times 10^{-2}$%/mg/h). This efficiency improves on the cell-tree translation result shown in FIG. 11 by 5-fold. The presence of the Sca2 protein increased the amplitude of the rapid first stages of reaction, and also increased the rate of the linear stage of reaction from 20 h to 96 h by ~3-fold. The continued linear reaction from 20 to 96 h at 65° C. indicates the enzymes maintained catalytic activity in these conditions.

Figure 19:
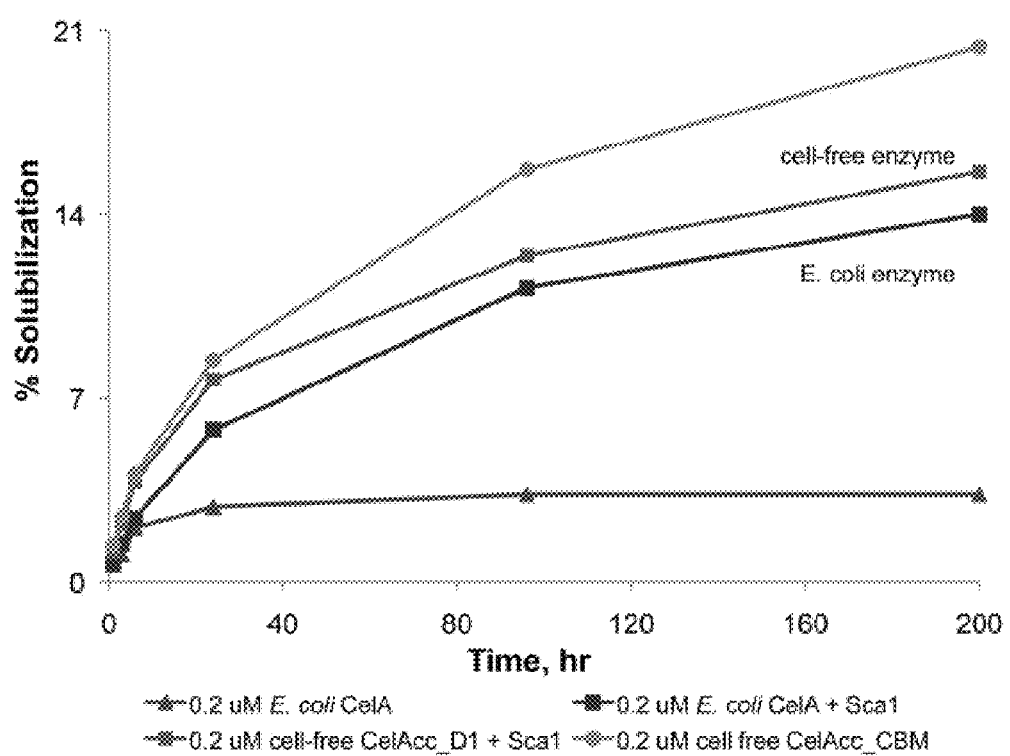
FIG. 19 is a graph showing % solubilization as a function of time for phosphoric acid swollen cellulose deconstruction for two enzyme or enzyme combinations expressed in E. coli (CelA and CelA plus Sca1) and for two enzymes or enzyme combinations expressed in cell-free systems (CelAcc_CBM and CelAcc_D1+Sca1). The % solubilization was measured at each indicated timepoint by first converting oligomers of glucose to monomers using C. thermocellum BglA and then using coupling enzymes to produce NADH from glucose. NADH was detected spectrophotometrically.

FIG. 19 shows percent solubilization as a function of time for four different experiments, one using 0.2 uM CelA produced in *E. coli* (solid triangles), one using a combination of 0.2 uM CelA produced in *E. coli* and Sca1 (black solid squares), one using a combination of 0.2 uM CelAcc_D1 produced in a cell-free system in combination with Sca1 (gray solid squares), and one using CelAcc_CBM in a cell-free system (gray solid circles). The results indicate that the context of expression affects the efficiency of biomass deconstruction. Specifically, wt CelA and the CelAcc_D1 construct behave equivalently 2) CelAcc_CBM in this assay is more efficient than the CelAcc_D1+Sca2 system, and 3) *E. coli* and cell free produced enzymes behave equivalently, validating our use of the more efficient cell-free translation system.

Figure 20:
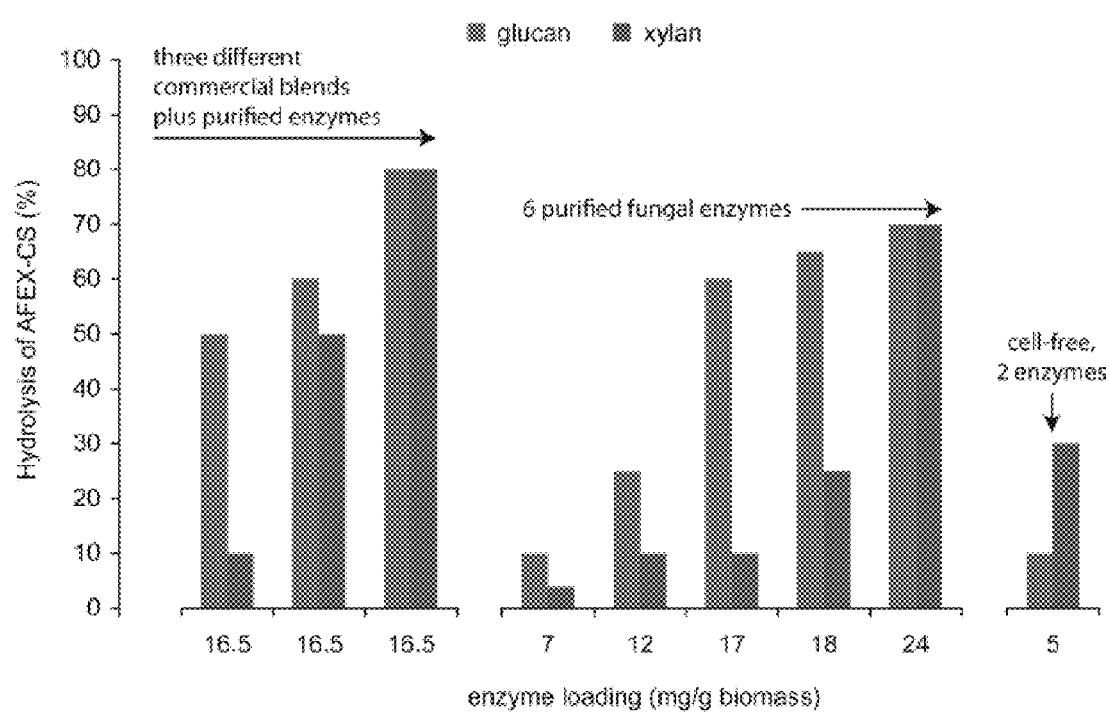
FIG. 20 is a bar graph showing endpoint yields (of glucan and xylan) as a function of enzyme loading (in mg/g biomass) for the hydrolysis of AFEX treated corn stover using three different commercial blends plus purified enzymes (leftmost grouping), 6 purified fungal enzymes (center grouping), and a two enzyme combination produced in a cell-free expression system with added scaffoldin protein Sca1 (rightmost grouping). The commercial preparations were, from left to right, Spezyme CP, Spezyme CP Multifect Pectinase and Spezyme CP Multifect Pectinase supplemented with xylanases NS50030 and NS22002 and the purified fungal enzymes were from Trichoderma reesei (Bruce Dale and Jonathan Walton, unpublished work). The enzymes produced by cell-free translation were CelA_D1 and XynZ with Sca1 produced in E. coli added as an additional reagent.
Figure 21:
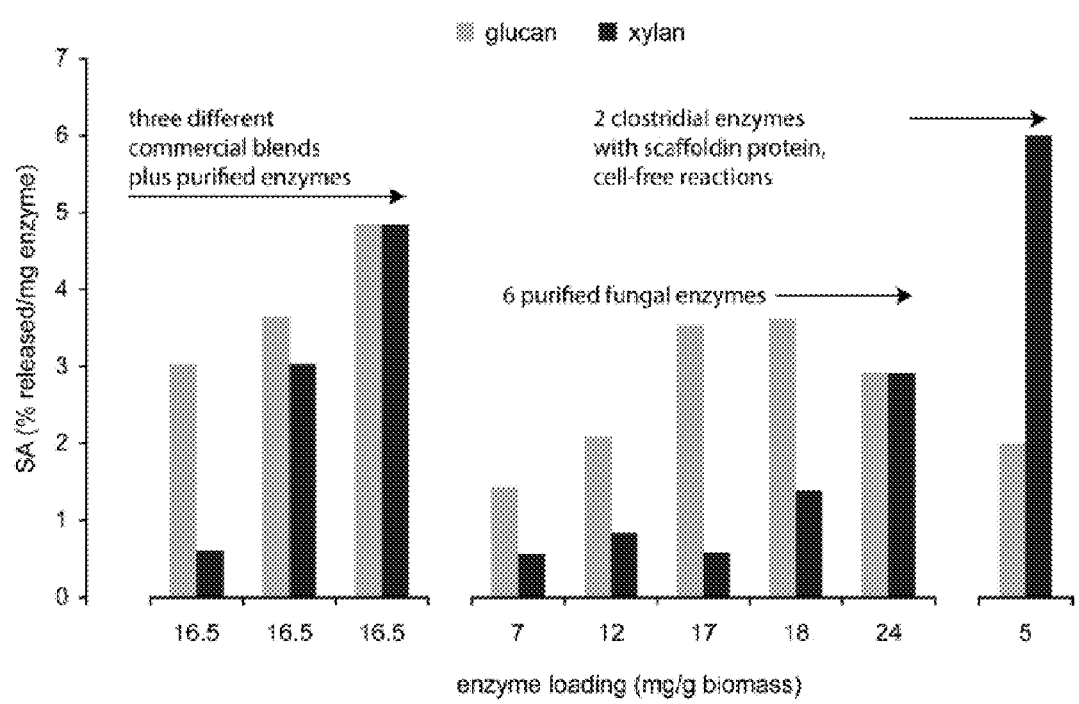
FIG. 21 is a bar graph showing specific activity for both glucan and xylan using coupling enzyme assays as a function of enzyme loading (in mg/g biomass) for the deconstruction of biomass using three different commercial blends plus purified enzymes (leftmost grouping), 6 purified fungal enzymes (center grouping), and a combination of two clostridium enzymes plus scaffoldin protein in a cell-free expression system (rightmost grouping). The commercial preparations were, from left to right, Spezyme CP, Spezyme CP Multifect Pectinase and Spezyme CP Multifect Pectinase supplemented with xylanases NS50030 and NS22002 and the fungal enzymes from Trichoderma reesei (Bruce Dale and Jonathan Walton, unpublished work). The enzymes produced by cell-free translation were CelA_D1 and XynZ with Sca1 produced in E. coli added as an additional reagent. Protein concentration of cell-free translation sample was determined by Coomassie Blue staining and densitometry.

FIGS. 20 and 21 shows the results of glycan and xylan-based enzyme assays measuring biomass deconstruction as a function of enzyme loading (mg/g biomass). FIG. 20 shows % hydrolysis of AFEX treated corn stover using for three different commercial blends plus purified enzyme (leftmost grouping, all having an enzyme load of 16.5 mg/g biomass), 6 purified fungal enzymes (center grouping), and for a combination of two enzymes produced in a cell-free system (rightmost grouping). This reaction contained CelAcc_D1, wt XynZ, and Sca1. It was allowed to continue for 72 hours. There was 2% w/v AFEX treated corn stover present and there was 0.05% w/w total enzyme loading. Note the two enzyme combination in a cell-free system exhibited high deconstruction efficiency at substantially lower enzyme loading than the conventional enzyme combinations.

FIG. 21 shows specific activity (SA) as % releasing/mg enzyme as a function of enzyme loading for same three different commercial blends plus purified enzyme (leftmost grouping, all having an enzyme load of 16.5 mg/g biomass), the same 6 purified fungal enzymes (center grouping), and for a combination of two clostridial enzymes produced in a cell-free system combined with scaffoldin protein (rightmost groping). The specific reactions were the same as reported above for FIG. 20, with the results normalized to % released/mg enzyme. Note the two enzyme combination in a cell-free system when combined with scaffoldin exhibited even higher deconstruction efficiency than that shown by the combination tested in FIG. 20, again at substantially lower enzyme loading than the conventional enzyme combinations.

Figure 22:
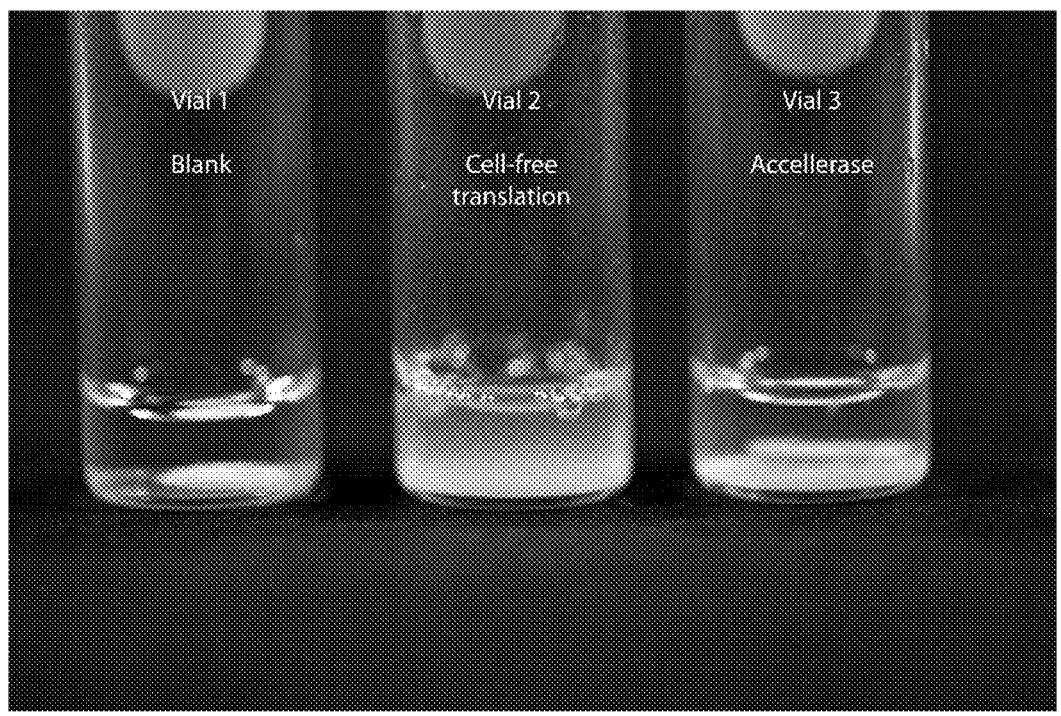
FIG. 22 shows enzymatic deconstruction of Whatman #1 filter paper, 3.6 mg paper punch at pH 5.8, 60° C. for 48 h using C. thermocellum enzymes produce by cell-free translation without purification. Vial 1 (left). Control containing buffer, filter paper and beta-glucosidase (Lucigen). Vial 2 (center). Clostridium thermocellum CelI, CelA_CBM, CelE_CBM, CelL, Sca1 and beta-glucosidase. All enzymes were produced using cell-free translation and added without purification to the reaction. Total protein loading ~0.8% weight of enzyme to weight of cellulose. Vial 3 (right). Accellerase 1000 (1% w/w loading of enzyme to weight of cellulose) plus beta-glucosidase (Lucigen).
Figure 23:
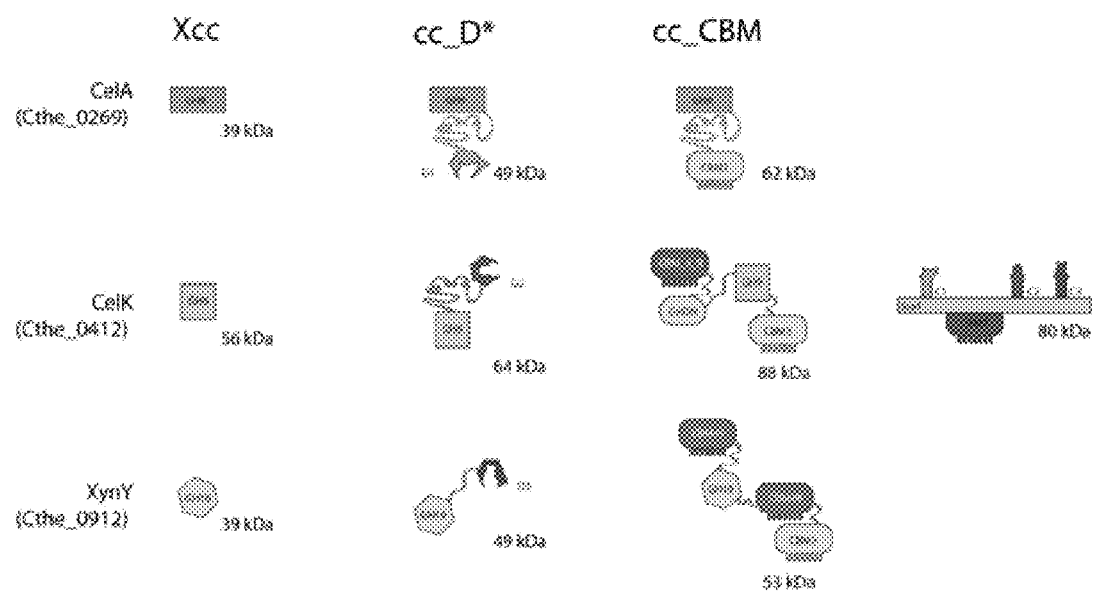
FIG. 23 includes schematic representations of the enzyme components and combinations used in the three-enzyme format experiments reported in Example 13.

Additionally, the inventors screened a control blank vial, a vial containing an Accellerase® solution, and a vial containing a solution of polypeptides produced by cell-free translation in a filter paper assay to compare the abilities of the solutions to facilitate cellulose breakdown. FIG. 22 shows enzymatic deconstruction of Whatman #1 filter paper, 3.6 mg paper punch at pH 5.8, 60° C. for 48 h using *C. thermocellum* enzymes produced by cell-free translation without purification. Vial 1 (left). Control containing buffer, filter paper and beta-glucosidase (Lucigen). Vial 2 (center). *Clostridium thermocellum* Cell, CelA_CBM, CelE_CBM, CelL, Sca1 and beta-glucosidase. All enzymes were produced using cell-free translation and added without purification to the reaction. Total protein loading was ~0.8% weight of enzyme to weight of cellulose. Vial 3 (right). Accellerase 1000 (1% w/w loading) plus beta-glucosidase (Lucigen). Accellerase is a commercially available enzyme complex for biomass hydrolysis (Danisco U.S.A.). The solution made using cell-free translation broke down the cellulose more quickly and completely than the Accellerase solution at the pH and temperature of the reaction. This demonstrates the catalytic efficacy and the temperature stability of the cell-free translated enzymes from *Clostridium thermocellum*.

Example 9

Assay of Total Soluble Products

HPLC analysis provides baseline separation of glucose, cellobiose, arabinose, mannose, xylose, xylobiose, and cellotriose. Cellotetrose and larger soluble oligosaccharides co-elute in this system. HPLC analysis is used to develop quantitative strategies for discovery of time-dependent effects of adding different enzymes to the reactions. The volume of an individual HPLC analysis sample is 200 μL of the cellulose degradation reaction supernatant. Quantification of products was performed using HPLC, in a buffer containing 0.5 ml of 100 mM citrate buffer, pH 6.0, 10 mM Pi, and 2 mM $Ca^{2+}$.

FIG. 13 shows multiple overlayed HPLC traces over time showing the total products released during the time course of four experiments, further corroborating the spectrophotometric results shown in FIGS. 11 and 12. The HPLC trace in FIG. 13 show the endpoint (96 h) products from the time courses shown in FIGS. 11 and 12. The bottom trace corresponds to the cellulose degradation by CelA alone that is shown in FIG. 11. The trace that is second from the bottom corresponds to the time course of cellulose degradation by CelK alone shown in FIG. 11. These HPLC traces illustrate the differences in soluble oligosaccharide release by different cellulases. For example, CelA alone releases a mixture of cellotriose and cellobiose, while CelK releases predominantly cellobiose. Note the dramatic increase in soluble oligosaccharides released when a scaffoldin construct capable of mediating enzyme-substrate binding is added to the system coexpressing CelA and CelK (top trace compared to the second trace from the top).

FIG. 14 shows two HPLC traces over time showing the total products released during the time course of two experiments. In one experiment, CelAcc_D1 and XynYcc_D3 were combined with Sca1 (dashed line), and were found to be capable of the deconstruction of AFEX-treated corn stover. In a separate experiment, CelA_D1 and XynZ were combined with Sca1, and were found to have improved capacity for the deconstruction of AFEX-treated corn stover (solid line). This improved capacity is evidenced by increased formation of cellotriose, xylobiose, and glucose. This result demonstrates the utility of the present invention for identifying improved enzymes, and combinations thereof, for biomass deconstruction. This result also demonstrates the ability to discover unique combinations of enzymes with customized properties for biomass deconstruction. The reactions of FIG. 14 were carried out with a 2% w/v loading of AFEX-treated corn stover in reaction buffer amended with 5 μL/mL of the cell-free translation of each of the indicated enzymes (providing an ~0.025% weight loading of enzyme preparation per weight of biomass) at 60° C. with shaking at 325 rpm for 72 h.

Example 10

Methods Used for Spectrophotometric Assays of Soluble Sugars

For glucose assays, a schematic of the method is provided in FIG. 3. An individual spectrophotometric reaction contains 10-100 μL of the cellulose deconstruction reaction supernatant incubated with BglA from *Clostridium thermocellum* (Cthe_0212) for 30 minutes at 60° C. This reaction mixture is then diluted to a final volume of 1 mL with 50 mM phosphate pH 7.2, 25 mM $Mg^{2+}$, 1 mM $NADP^+$, 1 mM ATP, 0.5 U hexokinase (Sigma, from *Saccharomyces cerevisiae*), and 0.5 U glucose 6-phosphate dehydrogenase (Sigma, from Bakers Yeast).

The assay readout is a spectrophotometric determination of NADPH from a coupled assay with hexokinase and glucose 6-phosphate dehydrogenase performed at room temperature. If desired, the volume of the spectrophotometric reaction can be scaled down to match 96- or 384-well plate formats.

For xylose assays, a schematic of this method is provided in FIG. 3. An individual spectrophotometric reaction mixture contains 10-100 μL of the cellulose deconstruction reaction supernatant incubated with β-xylosidase from Lucigen for 30 minutes at 60° C. This reaction is then assayed according to the D-Xylose. Assay kit from Megazyme, Wicklow Ireland. The assay readout is a spectrophotometric determination of NADH from a coupled assay with xylose mutarotase and β-xylose dehydrogenase to convert xylose to xylonic acid. If desired, the volume of the spectrophotometric reaction can be scaled down to match 96- or 384-well plate formats.

Example 11

Characterizing Enzymes from Cell-Free Translation using Small Molecule Analogs

In this Example, the inventors demonstrate that enzymatic activity can be successfully assayed in cell-free translation systems of the present invention without the need for intermediate purification steps. The inventors used three different 4-methylumbeliferyl derivatives to assay the enzymatic activity of CelAcc_CBM, CelKcc_CBM, CelLcc_CBM, and CelRcc_CBM, each produced in a cell free translation system. These small molecule assays were performed according to the method of J. L. Maddocks and M. J. Greenan (J. Clin Pathol (1975) 28:686-687, which is incorporated by reference herein. The results are shown in Table 5 below.

TABLE 5

Small Molecule Catalytic Assay Results

| Substrates | CelAcc_CBM | CelKcc_CBM | CelLcc_CBM | CelRcc_CBM |
|---|---|---|---|---|
| 4-Methylumbeliferyl-β-D-cellobioside (MUC) | 96 | 2737 | 32049 | 81 |
| MUC | 73 | 2628 | 34912 | 79 |
| MUC | 78 | 2612 | 37197 | 79 |
| 4-methylumbelliferyl-β-D-glucopyranoside (MUG) | 1797 | 809 | 1701 | 1843 |
| MUG | 1901 | 748 | 1569 | 1426 |
| MUG | 1877 | 752 | 1375 | 1352 |
| 4-Methylumbelliferyl-β-D-mannopyranoside (MUM) | 1603 | 1092 | 652 | 1494 |
| MUM | 1642 | 1034 | 596 | 1593 |

Example 12

Demonstration of Synergy for Enzyme Combinations of cc_CBM Enzymes

Table 6 shows an example of combining enzymes prepared by cell-free translation into combinatorial assemblies of enzymes that have improved performance relative to the individual enzymes. The calculated turnover numbers (expressed as the rate constants $k_{cat}$) for individual reactions of CelAcc_CBM, CelKcc_CBM, CelLcc_CBM and CelRcc_CBM with crystalline cellulose are indicated.

Any increase in activity for an enzyme combination as compared to the expected additive effects of the individual activities is known in the field as synergy. As further shown in Table 6, all the combinations of enzymes tested showed synergy after both 24 and 48 hours. For example, the combination of CelAcc_CBM and CelKcc_CBM gave 3.27 times higher release of glucose than the amount expected from their individual rates. CelKcc_CBM imparts synergy with each enzyme, demonstrating the importance of this enzyme for cellulose hydrolysis reactions.

TABLE 6

Synergy in Combinations of cc_CBM enzymes in Cell-Free Systems

| Enzymes | $k_{cat}$ (min$^{-1}$) | Synergy factor (24 h) | Synergy factor (48 h) |
|---|---|---|---|
| CelAcc_CBM (A) | 2.08 | | |
| CelKcc_CBM (K) | 6.72 | | |
| CelLcc_CBM (L) | 3.91 | | |
| CelRcc_CBM (R) | 4.05 | | |
| A + K | | 3.27 | 1.79 |
| A + L | | 1.51 | 1.40 |
| A + R | | 1.37 | 1.33 |
| K + L | | 2.86 | 2.07 |
| K + R | | 1.74 | 1.26 |
| L + R | | 1.89 | 1.97 |
| A + K + L + R | | 3.14 | 2.56 |

Example 13

Three or More Enzyme Combinations

In this Example, the inventors used the cell-free expression methods to assess deconstruction using a control system having no enzymes (reaction 1), several three-enzyme systems (reactions 2-5), and a ten-enzyme system having varying enzyme loading and corn stover concentrations (reactions 6-8). Tables 7 and 8 show the enzymes, other components, and reaction conditions used for reactions 1-5. Table 9 shows the enzymes, other components, and reaction conditions used in reactions 5-8.

TABLE 7

Components Included in Reactions 1-5

| | CelA | | | CelK | | | XynY | | | | | |
|---|---|---|---|---|---|---|---|---|---|---|---|---|
| | CelAcc | CelAcc_D1 | CelAcc_CBM | CelKcc | CelK_D1 | CelK_CMB | XynYcc | XynYcc_D1 | XynY_CBM | Sca1 | BglA | Bxl |
| 1 | | | | | | | | | | | | |
| 2 | X | | | X | | | X | | | | X | X |
| 3 | | X | | | X | | | X | | | X | X |
| 4 | | X | | | X | | | X | | X | X | X |
| 5 | | | X | | | X | | | X | | X | X |

TABLE 8

Enzymes, Components, and Reaction Conditions for Reactions 1-5

| Reaction | Enzymes | µg/mL Enzyme | Substrate | Enzyme loading % w/w protein/glucan |
|---|---|---|---|---|
| 1 | no enzymes | 0 | 1% w/v AFEX corn stover | na |
| 2 | 16 ug/mL CelAcc, CelKcc, XynYcc, 25 ug/mL BglA, 25 ug/mL Bxl | 98 | 1% w/v AFEX corn stover | 2.50% |
| 3 | 16 ug/mL CelAcc_D1, CelKcc_D1, XynYcc_D3, 25 ug/mL BglA, 25 ug/mL Bxl | 98 | 1% w/v AFEX corn stover | 2.50% |
| 4 | 16 ug/mL CelAcc_D1, CelKcc_D1, XynYcc_D3, 25 ug/mL BglA, 25 ug/mL Bxl, 1 uM Sca1 | 98 | 1% w/v AFEX corn stover | 2.50% |
| 5 | 16 ug/mL CelAcc_CBM, CelKcc_CBM, XynYcc_CBM, 25 ug/mL, BglA, 25 ug/mL Bxl | 98 | 1% w/v AFEX corn stover | 2.50% |

TABLE 9

Enzymes, Components, and Reaction Conditions for Reactions 5-8

| Reaction | A | B | C | Enzymes present | | | |
|---|---|---|---|---|---|---|---|
| 1 | 0 | 1% | na | none | | | |
| 5 | 98 | 1% | 2.5% | CelAcc_CBM | CelKcc_CBM | XynYcc_CBM | |
| 6 | 133 | 1% | 3.3% | CelAcc_CBM | CelKcc_CBM | XynYcc_CBM | CelRcc_CBM |
| 7 | 133 | 0.50% | 6.6% | " | " | " | " |
| 8 | 133 | 0.10% | 33.0% | " | " | " | " |

| Reaction |
|---|
| 1 |
| 5 |

TABLE 9-continued

Enzymes, Components, and Reaction Conditions for Reactions 5-8

| | | | | | | | |
|---|---|---|---|---|---|---|---|
| 6 | CelLcc_CBM | XynZ | XynCcc_CBM | ManAcc_CBM | ChiAcc_CBM | LicBcc_CBM | |
| 7 | " | " | " | " | " | " | |
| 8 | " | " | " | " | " | " | |

Figure 24A:
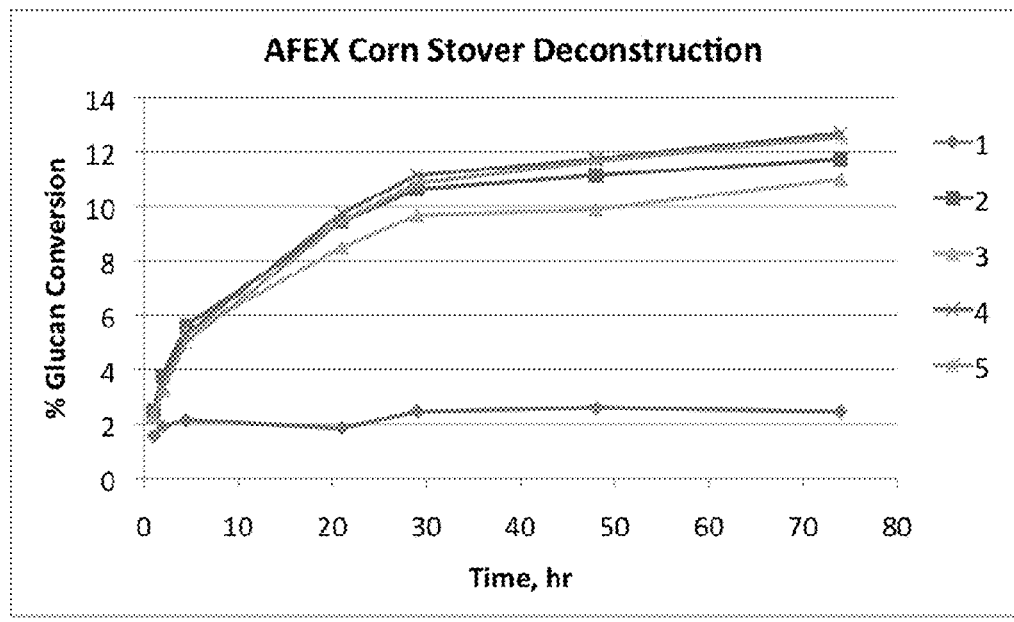
FIG. 24 are graphs showing percent glucose conversion (24A) and percent xylan conversion (24B) as a function of time for the deconstruction of AFEX corn stover for five different enzyme combinations/conditions, as further described in Example 13.
Figure 24B:
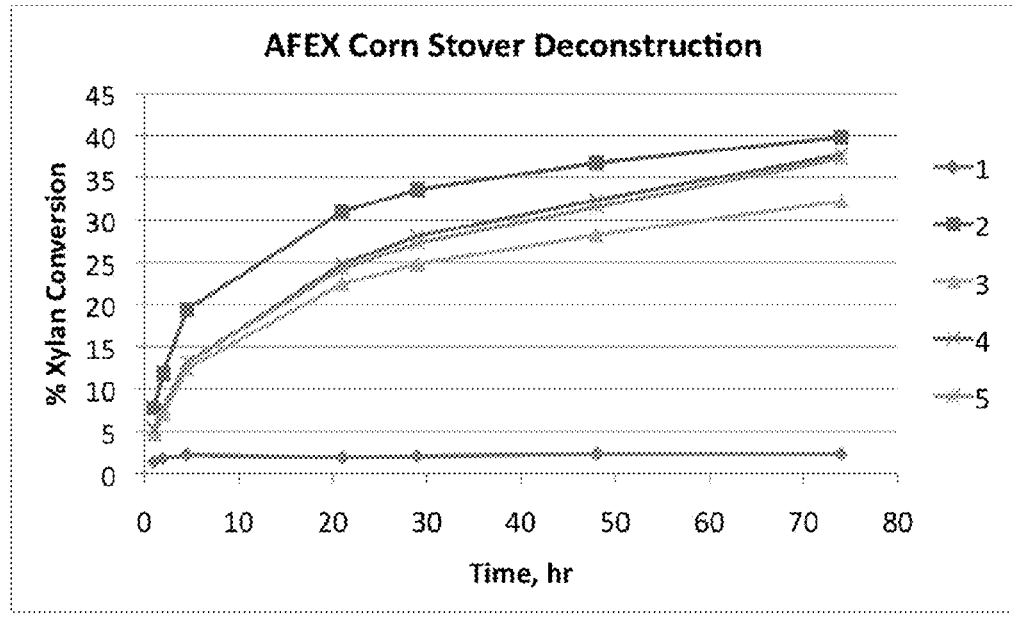
Figure 25A:
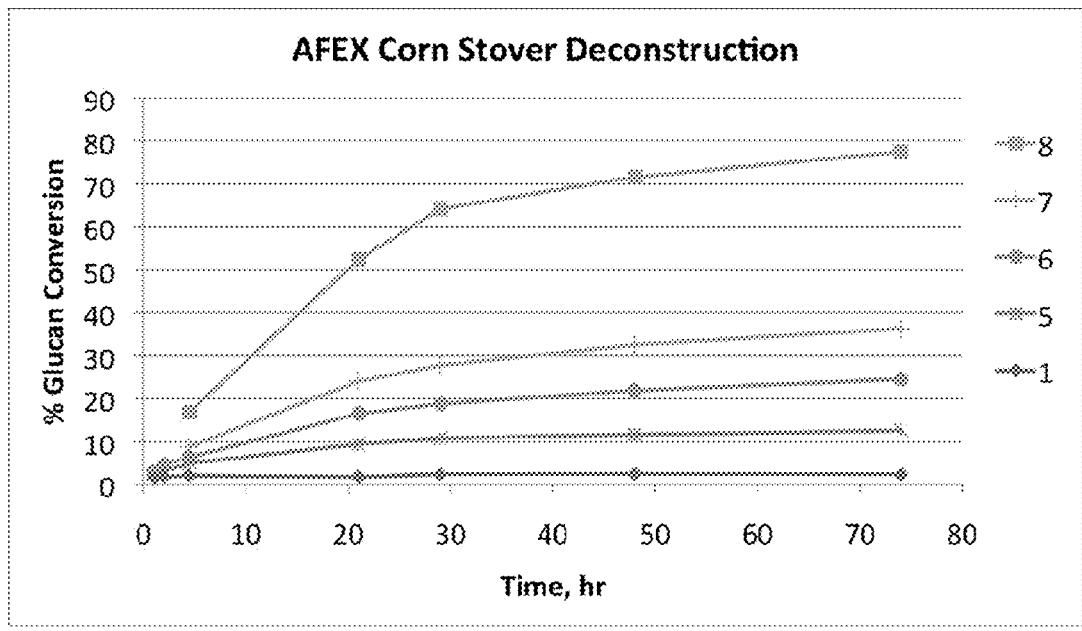
FIG. 25 are graphs showing percent glucose conversion (25A) and percent xylan conversion (25B) as a function of time for the deconstruction of AFEX corn stover for five different enzyme combinations/conditions, as further described in Example 13.
Figure 25B:
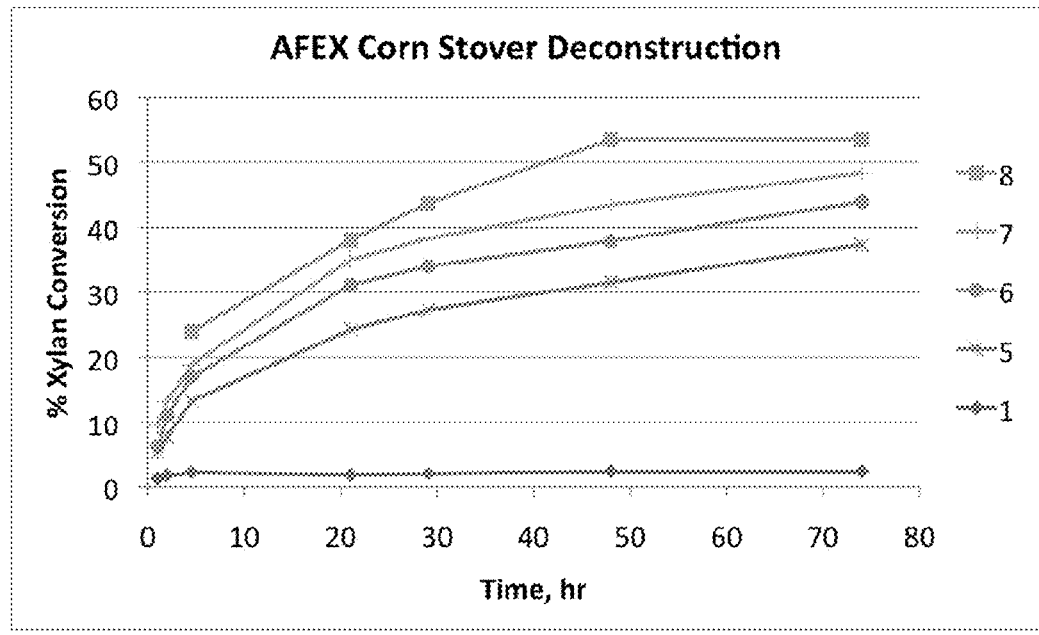

Reactions 5-8 contain BglA and Bxl.
A, Total enzyme µg/ml of reaction
B, AFEX corn stover, % w/v
C, Enzyme loading, % w/w protein/glucan As can be seen in the data shown in FIGS. 24A and B, effective corn stover deconstruction was achieved in three-enzyme systems. Furthermore, as can be seen in the data shown in FIGS. 25A and 25B, the ten-enzyme system worked substantially better than the three-enzyme systems, and can be made even more effective by systematically changing the biomass concentration and protein loading of the system. Although the ten-enzyme system approaches 80% conversion of AFEX-corn stover under certain reaction conditions (i.e. high protein loading), further optimization should lead to even better results using this combination of enzymes.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of genetic engineering, molecular biology, chemical engineering, and biochemistry, are within the scope of this invention. All publications, patents, and patent applications cited herein are incorporated by reference in their entirety for all purposes.

---

What is claimed is:

1. A polypeptide comprising a complete amino acid sequence selected from the group consisting of CelAcc CBM (SEQ ID NO:1) and CelRcc_CBM (SEQ ID NO:4).

2. The polypeptide of claim 1, wherein the complete amino acid sequence is SEQ ID NO:1.

3. The polypeptide of claim 1, wherein the complete amino acid sequence is SEQ ID NO:4.

* * * * *

SEQUENCE LISTING

<160> NUMBER OF SEQ ID NOS: 9

<210> SEQ ID NO 1
<211> LENGTH: 567
<212> TYPE: PRT
<213> ORGANISM: Clostridium thermocellum

<400> SEQUENCE: 1

```
Met Gly His His His His His His Ala Ile Ala Met Val Pro Phe Asn
1               5                   10                  15

Thr Lys Tyr Pro Tyr Gly Pro Thr Ser Ile Ala Asp Asn Gln Ser Glu
            20                  25                  30

Val Thr Ala Met Leu Lys Ala Glu Trp Glu Asp Trp Lys Ser Lys Arg
        35                  40                  45

Ile Thr Ser Asn Gly Ala Gly Gly Tyr Lys Arg Val Gln Arg Asp Ala
    50                  55                  60

Ser Thr Asn Tyr Asp Thr Val Ser Glu Gly Met Gly Tyr Gly Leu Leu
65                  70                  75                  80

Leu Ala Val Cys Phe Asn Glu Gln Ala Leu Phe Asp Asp Leu Tyr Arg
                85                  90                  95

Tyr Val Lys Ser His Phe Asn Gly Asn Gly Leu Met His Trp His Ile
            100                 105                 110

Asp Ala Asn Asn Asn Val Thr Ser His Asp Gly Gly Asp Gly Ala Ala
        115                 120                 125

Thr Asp Ala Asp Glu Asp Ile Ala Leu Ala Leu Ile Phe Ala Asp Lys
    130                 135                 140

Leu Trp Gly Ser Ser Gly Ala Ile Asn Tyr Gly Gln Glu Ala Arg Thr
145                 150                 155                 160

Leu Ile Asn Asn Leu Tyr Asn His Cys Val Glu His Gly Ser Tyr Val
                165                 170                 175

Leu Lys Pro Gly Asp Arg Trp Gly Gly Ser Ser Val Thr Asn Pro Ser
            180                 185                 190

Tyr Phe Ala Pro Ala Trp Tyr Lys Val Tyr Ala Gln Tyr Thr Gly Asp
        195                 200                 205
```

Thr Arg Trp Asn Gln Val Ala Asp Lys Cys Tyr Gln Ile Val Glu Glu
    210                 215                 220

Val Lys Lys Tyr Asn Asn Gly Thr Gly Leu Val Pro Asp Trp Cys Thr
225                 230                 235                 240

Ala Ser Gly Thr Pro Ala Ser Gly Gln Ser Tyr Asp Tyr Lys Tyr Asp
                245                 250                 255

Ala Thr Arg Tyr Gly Trp Arg Thr Ala Val Asp Tyr Ser Trp Phe Gly
                260                 265                 270

Asp Gln Arg Ala Lys Ala Asn Cys Asp Met Leu Thr Lys Phe Phe Ala
                275                 280                 285

Arg Asp Gly Ala Lys Gly Ile Val Asp Gly Tyr Thr Ile Gln Gly Ser
    290                 295                 300

Lys Ile Ser Asn Asn His Asn Ala Ser Phe Ile Gly Pro Val Ala Ala
305                 310                 315                 320

Ala Ser Met Thr Gly Tyr Asp Leu Asn Phe Ala Lys Glu Leu Tyr Arg
                325                 330                 335

Glu Thr Val Ala Val Lys Asp Ser Glu Tyr Tyr Gly Tyr Tyr Gly Asn
                340                 345                 350

Ser Leu Arg Leu Leu Thr Leu Leu Tyr Ile Thr Gly Gly Leu Asn Ala
                355                 360                 365

Thr Pro Thr Lys Gly Ala Thr Pro Thr Asn Thr Ala Thr Pro Thr Lys
    370                 375                 380

Ser Ala Thr Ala Thr Pro Thr Arg Pro Ser Val Pro Thr Asn Thr Pro
385                 390                 395                 400

Thr Asn Thr Pro Ala Asn Thr Pro Val Ser Gly Asn Leu Lys Val Glu
                405                 410                 415

Phe Tyr Asn Ser Asn Pro Ser Asp Thr Thr Asn Ser Ile Asn Pro Gln
                420                 425                 430

Phe Lys Val Thr Asn Thr Gly Ser Ser Ala Ile Asp Leu Ser Lys Leu
    435                 440                 445

Thr Leu Arg Tyr Tyr Tyr Thr Val Asp Gly Gln Lys Asp Gln Thr Phe
450                 455                 460

Trp Cys Asp His Ala Ala Ile Ile Gly Ser Asn Gly Ser Tyr Asn Gly
465                 470                 475                 480

Ile Thr Ser Asn Val Lys Gly Thr Phe Val Lys Met Ser Ser Ser Thr
                485                 490                 495

Asn Asn Ala Asp Thr Tyr Leu Glu Ile Ser Phe Thr Gly Gly Thr Leu
                500                 505                 510

Glu Pro Gly Ala His Val Gln Ile Gln Gly Arg Phe Ala Lys Asn Asp
    515                 520                 525

Trp Ser Asn Tyr Thr Gln Ser Asn Asp Tyr Ser Phe Lys Ser Ala Ser
530                 535                 540

Gln Phe Val Glu Trp Asp Gln Val Thr Ala Tyr Leu Asn Gly Val Leu
545                 550                 555                 560

Val Trp Gly Lys Glu Pro Gly
                565

<210> SEQ ID NO 2
<211> LENGTH: 996
<212> TYPE: PRT
<213> ORGANISM: Clostridium thermocellum

<400> SEQUENCE: 2

Met Gly His His His His His His Ala Ile Ala Met Glu Asp Lys Ser

-continued

```
1               5                   10                  15
Ser Lys Leu Pro Asp Tyr Lys Asn Asp Leu Leu Tyr Glu Arg Thr Phe
                20                  25                  30
Asp Glu Gly Leu Cys Phe Pro Trp His Thr Cys Glu Asp Ser Gly Gly
                35                  40                  45
Lys Cys Asp Phe Ala Val Val Asp Val Pro Gly Glu Pro Gly Asn Lys
                50                  55                  60
Ala Phe Arg Leu Thr Val Ile Asp Lys Gly Gln Asn Lys Trp Ser Val
65                  70                  75                  80
Gln Met Arg His Arg Gly Ile Thr Leu Glu Gln Gly His Thr Tyr Thr
                85                  90                  95
Val Arg Phe Thr Ile Trp Ser Asp Lys Ser Cys Arg Val Tyr Ala Lys
                100                 105                 110
Ile Gly Gln Met Gly Glu Pro Tyr Thr Glu Tyr Trp Asn Asn Asn Trp
                115                 120                 125
Asn Pro Phe Asn Leu Thr Pro Gly Gln Lys Leu Thr Val Glu Gln Asn
                130                 135                 140
Phe Thr Met Asn Tyr Pro Thr Asp Asp Thr Cys Glu Phe Thr Phe His
145                 150                 155                 160
Leu Gly Gly Glu Leu Ala Ala Gly Thr Pro Tyr Tyr Val Tyr Leu Asp
                165                 170                 175
Asp Val Ser Leu Tyr Asp Pro Arg Phe Val Lys Pro Val Glu Tyr Val
                180                 185                 190
Leu Pro Gln Pro Asp Val Arg Val Asn Gln Val Gly Tyr Leu Pro Phe
                195                 200                 205
Ala Lys Lys Tyr Ala Thr Val Val Ser Ser Thr Ser Pro Leu Lys
                210                 215                 220
Trp Gln Leu Leu Asn Ser Ala Asn Gln Val Val Leu Glu Gly Asn Thr
225                 230                 235                 240
Ile Pro Lys Gly Leu Asp Lys Asp Ser Gln Asp Tyr Val His Trp Ile
                245                 250                 255
Asp Phe Ser Asn Phe Lys Thr Glu Gly Lys Gly Tyr Tyr Phe Lys Leu
                260                 265                 270
Pro Thr Val Asn Ser Asp Thr Asn Tyr Ser His Pro Phe Asp Ile Ser
                275                 280                 285
Ala Asp Ile Tyr Ser Lys Met Lys Phe Asp Ala Leu Ala Phe Tyr
290                 295                 300
His Lys Arg Ser Gly Ile Pro Ile Glu Met Pro Tyr Ala Gly Gly Glu
305                 310                 315                 320
Gln Trp Thr Arg Pro Ala Gly His Ile Gly Ile Glu Pro Asn Lys Gly
                325                 330                 335
Asp Thr Asn Val Pro Thr Trp Pro Gln Asp Asp Glu Tyr Ala Gly Arg
                340                 345                 350
Pro Gln Lys Tyr Tyr Thr Lys Asp Val Thr Gly Gly Trp Tyr Asp Ala
                355                 360                 365
Gly Asp His Gly Lys Tyr Val Val Asn Gly Gly Ile Ala Val Trp Thr
                370                 375                 380
Leu Met Asn Met Tyr Glu Arg Ala Lys Ile Arg Gly Ile Ala Asn Gln
385                 390                 395                 400
Gly Ala Tyr Lys Asp Gly Gly Met Asn Ile Pro Glu Arg Asn Asn Gly
                405                 410                 415
Tyr Pro Asp Ile Leu Asp Glu Ala Arg Trp Glu Ile Glu Phe Phe Lys
                420                 425                 430
```

```
Lys Met Gln Val Thr Glu Lys Glu Asp Pro Ser Ile Ala Gly Met Val
            435                 440                 445

His His Lys Ile His Asp Phe Arg Trp Thr Ala Leu Gly Met Leu Pro
    450                 455                 460

His Glu Asp Pro Gln Pro Arg Tyr Leu Arg Pro Val Ser Thr Ala Ala
465                 470                 475                 480

Thr Leu Asn Phe Ala Ala Thr Leu Ala Gln Ser Ala Arg Leu Trp Lys
                485                 490                 495

Asp Tyr Asp Pro Thr Phe Ala Ala Asp Cys Leu Glu Lys Ala Glu Ile
            500                 505                 510

Ala Trp Gln Ala Ala Leu Lys His Pro Asp Ile Tyr Ala Glu Tyr Thr
        515                 520                 525

Pro Gly Ser Gly Gly Pro Gly Gly Pro Tyr Asn Asp Asp Tyr Val
    530                 535                 540

Gly Asp Glu Phe Tyr Trp Ala Ala Cys Glu Leu Tyr Val Thr Thr Gly
545                 550                 555                 560

Lys Asp Glu Tyr Lys Asn Tyr Leu Met Asn Ser Pro His Tyr Leu Glu
                565                 570                 575

Met Pro Ala Lys Met Gly Glu Asn Gly Gly Ala Asn Gly Glu Asp Asn
            580                 585                 590

Gly Leu Trp Gly Cys Phe Thr Trp Gly Thr Thr Gln Gly Leu Gly Thr
        595                 600                 605

Ile Thr Leu Ala Leu Val Glu Asn Gly Leu Pro Ala Thr Asp Ile Gln
    610                 615                 620

Lys Ala Arg Asn Asn Ile Ala Lys Ala Ala Asp Arg Trp Leu Glu Asn
625                 630                 635                 640

Ile Glu Glu Gln Gly Tyr Arg Leu Pro Ile Lys Gln Ala Glu Asp Glu
                645                 650                 655

Arg Gly Gly Tyr Pro Trp Gly Ser Asn Ser Phe Ile Leu Asn Gln Met
            660                 665                 670

Ile Val Met Gly Tyr Ala Tyr Asp Phe Thr Gly Asn Ser Lys Tyr Leu
        675                 680                 685

Asp Gly Met Gln Asp Gly Met Ser Tyr Leu Leu Gly Arg Asn Gly Leu
    690                 695                 700

Asp Gln Ser Tyr Val Thr Gly Tyr Gly Glu Arg Pro Leu Gln Asn Pro
705                 710                 715                 720

His Asp Arg Phe Trp Thr Pro Gln Thr Ser Lys Lys Phe Pro Ala Pro
                725                 730                 735

Pro Pro Gly Ile Ile Ala Gly Gly Pro Asn Ser Arg Phe Glu Asp Pro
            740                 745                 750

Thr Ile Thr Ala Ala Val Lys Lys Asp Thr Pro Pro Gln Lys Cys Tyr
        755                 760                 765

Ile Asp His Thr Asp Ser Trp Ser Thr Asn Glu Ile Thr Val Asn Trp
    770                 775                 780

Asn Ala Pro Phe Ala Trp Val Thr Ala Gly Leu Asn Ala Thr Pro Thr
785                 790                 795                 800

Lys Gly Ala Thr Pro Thr Asn Thr Ala Thr Pro Thr Lys Ser Ala Thr
                805                 810                 815

Ala Thr Pro Thr Arg Pro Ser Val Pro Thr Asn Thr Pro Thr Asn Thr
            820                 825                 830

Pro Ala Asn Thr Pro Val Ser Gly Asn Leu Lys Val Glu Phe Tyr Asn
835                 840                 845
```

```
Ser Asn Pro Ser Asp Thr Thr Asn Ser Ile Asn Pro Gln Phe Lys Val
    850                 855                 860

Thr Asn Thr Gly Ser Ser Ala Ile Asp Leu Ser Lys Leu Thr Leu Arg
865                 870                 875                 880

Tyr Tyr Tyr Thr Val Asp Gly Gln Lys Asp Gln Thr Phe Trp Cys Asp
                885                 890                 895

His Ala Ala Ile Ile Gly Ser Asn Gly Ser Tyr Asn Gly Ile Thr Ser
                900                 905                 910

Asn Val Lys Gly Thr Phe Val Lys Met Ser Ser Ser Thr Asn Asn Ala
            915                 920                 925

Asp Thr Tyr Leu Glu Ile Ser Phe Thr Gly Gly Thr Leu Glu Pro Gly
930                 935                 940

Ala His Val Gln Ile Gln Gly Arg Phe Ala Lys Asn Asp Trp Ser Asn
945                 950                 955                 960

Tyr Thr Gln Ser Asn Asp Tyr Ser Phe Lys Ser Ala Ser Gln Phe Val
                965                 970                 975

Glu Trp Asp Gln Val Thr Ala Tyr Leu Asn Gly Val Leu Val Trp Gly
                980                 985                 990

Lys Glu Pro Gly
        995

<210> SEQ ID NO 3
<211> LENGTH: 614
<212> TYPE: PRT
<213> ORGANISM: Clostridium thermocellum

<400> SEQUENCE: 3

Met Gly His His His His His His Ala Ile Ala Met Asp Pro Asn Asn
1               5                   10                  15

Asp Asp Trp Leu His Val Glu Gly Asn Lys Ile Val Asp Met Tyr Gly
            20                  25                  30

Asn Gln Val Trp Leu Thr Gly Cys Asn Trp Phe Gly Phe Asn Thr Gly
        35                  40                  45

Thr Asn Val Phe Asp Gly Val Trp Ser Cys Asn Met Arg Glu Ala Leu
50                  55                  60

Lys Gly Met Ala Asp Arg Gly Ile Asn Phe Leu Arg Ile Pro Ile Ser
65                  70                  75                  80

Thr Glu Leu Leu Tyr Gln Trp Ser Gln Gly Ile Tyr Pro Lys Ala Asn
                85                  90                  95

Val Asn Asp Phe Val Asn Pro Glu Leu Lys Gly Lys Asn Ser Leu Glu
            100                 105                 110

Leu Phe Asp Phe Ala Val Gln Cys Cys Lys Glu Phe Gly Ile Lys Ile
        115                 120                 125

Met Val Asp Ile His Ser Pro Ala Thr Asp Ala Met Gly His Met Tyr
130                 135                 140

Pro Leu Trp Tyr Asp Gly Gln Phe Thr Thr Glu Ile Trp Ile Ser Thr
145                 150                 155                 160

Leu Glu Trp Leu Thr Glu Arg Tyr Lys Asn Asp Asp Thr Ile Leu Ala
                165                 170                 175

Leu Asp Leu Lys Asn Glu Pro His Gly Thr Pro Gly Ser Glu Leu Met
            180                 185                 190

Ala Lys Trp Asp Gly Ser Thr Asp Leu Asn Asn Trp Lys His Ala Ala
        195                 200                 205

Glu Thr Cys Ala Lys Arg Ile Leu Ala Ile Asn Pro Asn Ile Leu Ile
210                 215                 220
```

-continued

Val Val Glu Gly Val Glu Val Tyr Pro Lys Pro Gly Tyr Asp Tyr Thr
225                 230                 235                 240

Ala Val Asp Glu Trp Gly Lys Glu Ser Lys Tyr Phe Tyr Asn Trp Trp
                245                 250                 255

Gly Gly Asn Leu Arg Gly Val Arg Asp Tyr Pro Ile Asp Leu Gly Lys
            260                 265                 270

His Gln Lys Gln Leu Val Tyr Ser Pro His Asp Tyr Gly Pro Leu Val
        275                 280                 285

His Lys Gln Pro Trp Phe Tyr Glu Gly Phe Asn Lys Glu Thr Leu Tyr
    290                 295                 300

Asn Asp Cys Trp Arg Asp Asn Trp Ala Tyr Ile His Glu Glu Asn Ile
305                 310                 315                 320

Ala Pro Leu Ile Val Gly Glu Trp Gly Gly Phe Met Asp Arg Gly Asp
                325                 330                 335

Asn Glu Lys Trp Met Lys Ala Leu Arg Asp Tyr Met Ile Glu Asn Lys
            340                 345                 350

Ile Ser His Thr Phe Trp Cys Tyr Asn Ala Asn Ser Gly Asp Thr Gly
        355                 360                 365

Gly Leu Val Tyr Tyr Asp Phe Ile Thr Trp Asp Glu Glu Lys Tyr Ala
    370                 375                 380

Leu Leu Lys Pro Ala Leu Trp Gln Thr Glu Asp Gly Lys Phe Ile Gly
385                 390                 395                 400

Leu Asp His Gln Ile Pro Leu Gly Ser Asn Gly Gly Leu Asn Ala Thr
                405                 410                 415

Pro Thr Lys Gly Ala Thr Pro Thr Asn Thr Ala Thr Pro Thr Lys Ser
            420                 425                 430

Ala Thr Ala Thr Pro Thr Arg Pro Ser Val Pro Thr Asn Thr Pro Thr
        435                 440                 445

Asn Thr Pro Ala Asn Thr Pro Val Ser Gly Asn Leu Lys Val Glu Phe
    450                 455                 460

Tyr Asn Ser Asn Pro Ser Asp Thr Thr Asn Ser Ile Asn Pro Gln Phe
465                 470                 475                 480

Lys Val Thr Asn Thr Gly Ser Ser Ala Ile Asp Leu Ser Lys Leu Thr
                485                 490                 495

Leu Arg Tyr Tyr Tyr Thr Val Asp Gly Gln Lys Asp Gln Thr Phe Trp
            500                 505                 510

Cys Asp His Ala Ala Ile Ile Gly Ser Asn Gly Ser Tyr Asn Gly Ile
        515                 520                 525

Thr Ser Asn Val Lys Gly Thr Phe Val Lys Met Ser Ser Ser Thr Asn
    530                 535                 540

Asn Ala Asp Thr Tyr Leu Glu Ile Ser Phe Thr Gly Gly Thr Leu Glu
545                 550                 555                 560

Pro Gly Ala His Val Gln Ile Gln Gly Arg Phe Ala Lys Asn Asp Trp
                565                 570                 575

Ser Asn Tyr Thr Gln Ser Asn Asp Tyr Ser Phe Lys Ser Ala Ser Gln
            580                 585                 590

Phe Val Glu Trp Asp Gln Val Thr Ala Tyr Leu Asn Gly Val Leu Val
        595                 600                 605

Trp Gly Lys Glu Pro Gly
    610

<210> SEQ ID NO 4
<211> LENGTH: 828

<212> TYPE: PRT
<213> ORGANISM: Clostridium thermocellum

<400> SEQUENCE: 4

```
Met Gly His His His His His Ala Ile Ala Met Asp Tyr Asn Tyr
1               5                   10                  15

Gly Glu Ala Leu Gln Lys Ala Ile Met Phe Tyr Glu Phe Gln Met Ser
            20                  25                  30

Gly Lys Leu Pro Asp Asn Ile Arg Asn Asn Trp Arg Gly Asp Ser Cys
            35                  40                  45

Leu Gly Asp Gly Ser Asp Val Gly Leu Asp Leu Thr Gly Gly Trp Phe
50                  55                  60

Asp Ala Gly Asp His Val Lys Phe Asn Leu Pro Met Ala Tyr Thr Ala
65                  70                  75                  80

Thr Met Leu Ala Trp Ala Val Tyr Glu Tyr Lys Asp Ala Leu Gln Lys
                85                  90                  95

Ser Gly Gln Leu Gly Tyr Leu Met Asp Gln Ile Lys Trp Ala Ser Asp
            100                 105                 110

Tyr Phe Ile Arg Cys His Pro Glu Lys Tyr Val Tyr Tyr Gln Val
        115                 120                 125

Gly Asn Gly Asp Met Asp His Arg Trp Trp Val Pro Ala Glu Cys Ile
130                 135                 140

Asp Val Gln Ala Pro Arg Pro Ser Tyr Lys Val Asp Leu Ser Asn Pro
145                 150                 155                 160

Gly Ser Thr Val Thr Ala Gly Thr Ala Ala Leu Ala Ala Thr Ala
            165                 170                 175

Leu Val Phe Lys Asp Thr Asp Pro Ala Tyr Ala Ala Leu Cys Ile Arg
            180                 185                 190

His Ala Lys Glu Leu Phe Asp Phe Ala Glu Thr Thr Met Ser Asp Lys
            195                 200                 205

Gly Tyr Thr Ala Ala Leu Asn Phe Tyr Thr Ser His Ser Gly Trp Tyr
            210                 215                 220

Asp Glu Leu Ser Trp Ala Gly Ala Trp Ile Tyr Leu Ala Asp Gly Asp
225                 230                 235                 240

Glu Thr Tyr Leu Glu Lys Ala Glu Lys Tyr Val Asp Lys Trp Pro Ile
            245                 250                 255

Glu Ser Gln Thr Thr Tyr Ile Ala Tyr Ser Trp Gly His Cys Trp Asp
            260                 265                 270

Asp Val His Tyr Gly Ala Ala Leu Leu Leu Ala Lys Ile Thr Asn Lys
            275                 280                 285

Ser Leu Tyr Lys Glu Ala Ile Glu Arg His Leu Asp Tyr Trp Thr Val
            290                 295                 300

Gly Phe Asn Gly Gln Arg Val Arg Tyr Thr Pro Lys Gly Leu Ala His
305                 310                 315                 320

Leu Thr Asp Trp Gly Val Leu Arg His Ala Thr Thr Ala Phe Leu
            325                 330                 335

Ala Cys Val Tyr Ser Asp Trp Ser Glu Cys Pro Arg Glu Lys Ala Asn
            340                 345                 350

Ile Tyr Ile Asp Phe Ala Lys Lys Gln Ala Asp Tyr Ala Leu Gly Ser
            355                 360                 365

Ser Gly Arg Ser Tyr Val Val Gly Phe Gly Val Asn Pro Pro Gln His
            370                 375                 380

Pro His His Arg Thr Ala His Ser Ser Trp Cys Asp Ser Gln Lys Val
385                 390                 395                 400
```

```
Pro Glu Tyr His Arg His Val Leu Tyr Gly Ala Leu Val Gly Gly Pro
            405                 410                 415

Asp Ala Ser Asp Ala Tyr Val Asp Ile Gly Asn Tyr Val Thr Asn
            420                 425                 430

Glu Val Ala Cys Asp Tyr Asn Ala Gly Phe Val Gly Leu Leu Ala Lys
            435                 440                 445

Met Tyr Glu Lys Tyr Gly Gly Asn Pro Ile Pro Asn Phe Met Ala Ile
            450                 455                 460

Glu Glu Lys Thr Asn Glu Glu Ile Tyr Val Glu Ala Thr Ala Asn Ser
465                 470                 475                 480

Asn Asn Gly Val Glu Leu Lys Thr Tyr Leu Tyr Asn Lys Ser Gly Trp
                485                 490                 495

Pro Ala Arg Val Cys Asp Lys Leu Ser Phe Arg Tyr Phe Met Asp Leu
            500                 505                 510

Thr Glu Tyr Val Ser Ala Gly Tyr Asn Pro Asn Asp Ile Thr Val Ser
            515                 520                 525

Ile Ile Tyr Ser Ala Ala Pro Thr Ala Lys Ile Ser Lys Pro Ile Leu
            530                 535                 540

Tyr Asp Ala Ser Lys Asn Ile Tyr Tyr Cys Glu Ile Asp Leu Ser Gly
545                 550                 555                 560

Thr Lys Ile Phe Pro Gly Ser Asn Ser Asp His Gln Lys Glu Thr Gln
            565                 570                 575

Phe Arg Ile Gln Pro Pro Ala Gly Ala Pro Trp Asp Asn Thr Asn Asp
            580                 585                 590

Phe Ser Tyr Gln Gly Ile Lys Lys Asn Gly Glu Val Val Lys Glu Met
            595                 600                 605

Pro Val Tyr Glu Asp Gly Ile Leu Ile Phe Gly Val Glu Pro Asn Gly
            610                 615                 620

Thr Gly Leu Asn Ala Thr Pro Thr Lys Gly Ala Thr Pro Thr Asn Thr
625                 630                 635                 640

Ala Thr Pro Thr Lys Ser Ala Thr Ala Thr Pro Thr Arg Pro Ser Val
                645                 650                 655

Pro Thr Asn Thr Pro Thr Asn Thr Pro Ala Asn Thr Pro Val Ser Gly
            660                 665                 670

Asn Leu Lys Val Glu Phe Tyr Asn Ser Asn Pro Ser Asp Thr Thr Asn
            675                 680                 685

Ser Ile Asn Pro Gln Phe Lys Val Thr Asn Thr Gly Ser Ser Ala Ile
            690                 695                 700

Asp Leu Ser Lys Leu Thr Leu Arg Tyr Tyr Tyr Thr Val Asp Gly Gln
705                 710                 715                 720

Lys Asp Gln Thr Phe Trp Cys Asp His Ala Ala Ile Ile Gly Ser Asn
            725                 730                 735

Gly Ser Tyr Asn Gly Ile Thr Ser Asn Val Lys Gly Thr Phe Val Lys
            740                 745                 750

Met Ser Ser Ser Thr Asn Asn Ala Asp Thr Tyr Leu Glu Ile Ser Phe
            755                 760                 765

Thr Gly Gly Thr Leu Glu Pro Gly Ala His Val Gln Ile Gln Gly Arg
            770                 775                 780

Phe Ala Lys Asn Asp Trp Ser Asn Tyr Thr Gln Ser Asn Asp Tyr Ser
785                 790                 795                 800

Phe Lys Ser Ala Ser Gln Phe Val Glu Trp Asp Gln Val Thr Ala Tyr
                805                 810                 815
```

Leu Asn Gly Val Leu Val Trp Gly Lys Glu Pro Gly
        820                 825

<210> SEQ ID NO 5
<211> LENGTH: 579
<212> TYPE: PRT
<213> ORGANISM: Clostridium thermocellum

<400> SEQUENCE: 5

Met Gly His His His His His His Ala Ile Ala Met Ser Leu Pro Thr
1               5                   10                  15

Lys Arg Ile Val Gly Tyr Phe Ala Glu Trp Asn Ile Tyr Leu Glu Asn
            20                  25                  30

Asn Tyr Tyr Glu Val Ser Asp Ile Pro Trp Asp Met Val Thr His Ile
        35                  40                  45

Asn Tyr Ala Phe Ala Lys Ile Glu Asn Gly Arg Ile Ala Ile Ile Asp
    50                  55                  60

Lys Trp Ala Ala Ile Gln Lys Pro Phe Gly Asp Asp Thr Trp Asp Thr
65                  70                  75                  80

Pro Ile Arg Gly His Phe Gly Gln Leu Ile Lys Tyr Lys Glu Gln Tyr
                85                  90                  95

Pro His Val Lys Thr Leu Ile Ser Val Gly Gly Trp Thr Glu Ser Lys
            100                 105                 110

Tyr Phe Ser Asp Val Ala Leu Thr Glu Glu Ser Arg Asn Thr Phe Ala
        115                 120                 125

Asp Ser Cys Val Glu Phe Ile Arg Thr Tyr Arg Phe Asp Gly Val Asp
    130                 135                 140

Ile Asp Trp Glu Tyr Pro Val Ser Gly Gly Met Pro Glu Asn Ile Arg
145                 150                 155                 160

Arg Pro Glu Asp Lys Gln Asn Phe Thr Leu Leu Leu Lys Cys Leu Arg
                165                 170                 175

Glu Lys Leu Asp Ala Ala Gly Ala Glu Asp Gly Lys His Tyr Leu Leu
            180                 185                 190

Thr Ile Ala Ala Pro Ala Gly Ser Phe Asn Ile Lys Asn Thr Glu Pro
        195                 200                 205

Glu Ile Tyr His Gln Tyr Leu Asp Phe Ile Asn Ile Met Thr Tyr Asp
    210                 215                 220

Tyr Ser Gly Ser Trp Glu Asn Val Ala Asn His Leu Ala Pro Leu Tyr
225                 230                 235                 240

Met Asn Pro Asn Asp Pro Ser Tyr Pro Glu Arg Lys Glu Lys Phe Asn
                245                 250                 255

Val Asp Trp Thr Val Lys Glu Tyr Leu Arg Leu Gly Val Pro Ala Glu
            260                 265                 270

Lys Ile Asn Val Gly Val Pro Tyr Tyr Ala Ala Gly Trp Gln Glu Val
        275                 280                 285

Asn Gly Gly Ile Asn Gly Leu Phe Gly Thr Ser Ser Lys Pro Leu Ser
    290                 295                 300

Ser Thr Gln Phe His Tyr Ile Asn Ser Leu Leu Lys Ser Pro Asp Leu
305                 310                 315                 320

Gly Phe Thr Arg Tyr Trp Asp Tyr Ala Met Val Pro Tyr Leu Trp
                325                 330                 335

Asn Pro Glu Ser Ala Thr Phe Tyr Ser Tyr Glu Asp Glu Ile Ser Leu
            340                 345                 350

Lys Asn Lys Cys Asp Tyr Val Ile Glu Asn Asn Leu Gly Gly Ile Met
        355                 360                 365

```
Ile Trp Glu Leu Ser Gly Asp Tyr Gly Leu Asn Ala Thr Pro Thr Lys
    370                 375                 380

Gly Ala Thr Pro Thr Asn Thr Ala Thr Pro Thr Lys Ser Ala Thr Ala
385                 390                 395                 400

Thr Pro Thr Arg Pro Ser Val Pro Thr Asn Thr Pro Thr Asn Thr Pro
                405                 410                 415

Ala Asn Thr Pro Val Ser Gly Asn Leu Lys Val Glu Phe Tyr Asn Ser
                420                 425                 430

Asn Pro Ser Asp Thr Thr Asn Ser Ile Asn Pro Gln Phe Lys Val Thr
                435                 440                 445

Asn Thr Gly Ser Ser Ala Ile Asp Leu Ser Lys Leu Thr Leu Arg Tyr
    450                 455                 460

Tyr Tyr Thr Val Asp Gly Gln Lys Asp Gln Thr Phe Trp Cys Asp His
465                 470                 475                 480

Ala Ala Ile Ile Gly Ser Asn Gly Ser Tyr Asn Gly Ile Thr Ser Asn
                485                 490                 495

Val Lys Gly Thr Phe Val Lys Met Ser Ser Thr Asn Asn Ala Asp
                500                 505                 510

Thr Tyr Leu Glu Ile Ser Phe Thr Gly Gly Thr Leu Glu Pro Gly Ala
    515                 520                 525

His Val Gln Ile Gln Gly Arg Phe Ala Lys Asn Asp Trp Ser Asn Tyr
    530                 535                 540

Thr Gln Ser Asn Asp Tyr Ser Phe Lys Ser Ala Ser Gln Phe Val Glu
545                 550                 555                 560

Trp Asp Gln Val Thr Ala Tyr Leu Asn Gly Val Leu Val Trp Gly Lys
                565                 570                 575

Glu Pro Gly

<210> SEQ ID NO 6
<211> LENGTH: 431
<212> TYPE: PRT
<213> ORGANISM: Clostridium thermocellum

<400> SEQUENCE: 6

Met Gly His His His His His His Ala Ile Ala Met Ala Ala Thr Val
1               5                   10                  15

Val Asn Thr Pro Phe Val Ala Val Phe Ser Asn Phe Asp Ser Ser Gln
                20                  25                  30

Trp Glu Lys Ala Asp Trp Ala Asn Gly Ser Val Phe Asn Cys Val Trp
            35                  40                  45

Lys Pro Ser Gln Val Thr Phe Ser Asn Gly Lys Met Ile Leu Thr Leu
50                  55                  60

Asp Arg Glu Tyr Gly Gly Ser Tyr Pro Tyr Lys Ser Gly Glu Tyr Arg
65                  70                  75                  80

Thr Lys Ser Phe Phe Gly Tyr Gly Tyr Tyr Glu Val Arg Met Lys Ala
                85                  90                  95

Ala Lys Asn Val Gly Ile Val Ser Ser Phe Phe Thr Tyr Thr Gly Pro
                100                 105                 110

Ser Asp Asn Asn Pro Trp Asp Glu Ile Asp Ile Glu Phe Leu Gly Lys
            115                 120                 125

Asp Thr Thr Lys Val Gln Phe Asn Trp Tyr Lys Asn Gly Val Gly Gly
130                 135                 140

Asn Glu Tyr Leu His Asn Leu Gly Phe Asp Ala Ser Gln Asp Phe His
145                 150                 155                 160
```

```
Thr Tyr Gly Phe Glu Trp Arg Pro Asp Tyr Ile Asp Phe Tyr Val Asp
                165                 170                 175

Gly Lys Lys Val Tyr Arg Gly Thr Arg Asn Ile Pro Val Thr Pro Gly
            180                 185                 190

Lys Ile Met Met Asn Leu Trp Pro Gly Ile Gly Val Asp Glu Trp Leu
        195                 200                 205

Gly Arg Tyr Asp Gly Arg Thr Pro Leu Gln Ala Glu Tyr Glu Tyr Val
    210                 215                 220

Lys Tyr Tyr Pro Gly Leu Asn Ala Thr Pro Thr Lys Gly Ala Thr Pro
225                 230                 235                 240

Thr Asn Thr Ala Thr Pro Thr Lys Ser Ala Thr Ala Thr Pro Thr Arg
                245                 250                 255

Pro Ser Val Pro Thr Asn Thr Pro Thr Asn Pro Ala Asn Thr Pro
                260                 265                 270

Val Ser Gly Asn Leu Lys Val Glu Phe Tyr Asn Ser Asn Pro Ser Asp
        275                 280                 285

Thr Thr Asn Ser Ile Asn Pro Gln Phe Lys Val Thr Asn Thr Gly Ser
    290                 295                 300

Ser Ala Ile Asp Leu Ser Lys Leu Thr Leu Arg Tyr Tyr Tyr Thr Val
305                 310                 315                 320

Asp Gly Gln Lys Asp Gln Thr Phe Trp Cys Asp His Ala Ala Ile Ile
                325                 330                 335

Gly Ser Asn Gly Ser Tyr Asn Gly Ile Thr Ser Asn Val Lys Gly Thr
            340                 345                 350

Phe Val Lys Met Ser Ser Ser Thr Asn Asn Ala Asp Thr Tyr Leu Glu
        355                 360                 365

Ile Ser Phe Thr Gly Gly Thr Leu Glu Pro Gly Ala His Val Gln Ile
    370                 375                 380

Gln Gly Arg Phe Ala Lys Asn Asp Trp Ser Asn Tyr Thr Gln Ser Asn
385                 390                 395                 400

Asp Tyr Ser Phe Lys Ser Ala Ser Gln Phe Val Glu Trp Asp Gln Val
                405                 410                 415

Thr Ala Tyr Leu Asn Gly Val Leu Val Trp Gly Lys Glu Pro Gly
            420                 425                 430

<210> SEQ ID NO 7
<211> LENGTH: 679
<212> TYPE: PRT
<213> ORGANISM: Clostridium thermocellum

<400> SEQUENCE: 7

Met Gly His His His His His His Ala Ile Ala Val Leu Ser Asp Gly
1               5                   10                  15

Asp Lys Tyr Glu Phe Glu Asp Gly Ile His Lys Gly Ala Gln Ile Tyr
                20                  25                  30

Thr Asp Tyr Val Gly Gln Asn Glu Tyr Gly Glu Val Phe Asp Leu Thr
            35                  40                  45

Gly Ser Thr Cys Ser Phe Ile Ala Gln Lys Gly Thr Ser Thr Ser Val
        50                  55                  60

Asn Val Glu Val Asp Lys Glu Gly Leu Tyr Glu Ile Phe Ile Cys Tyr
65                  70                  75                  80

Val Gln Pro Tyr Asp Lys Asn Lys Val Gln Tyr Leu Asn Val Asn
                85                  90                  95

Gly Val Asn Gln Gly Glu Ile Ser Phe Pro Phe Thr Leu Lys Trp Arg
```

```
                100                 105                 110
Glu Ile Ser Ala Gly Ile Val Lys Leu Asn Ala Gly Ile Asn Asn Ile
            115                 120                 125

Glu Leu Glu Ser Tyr Trp Gly Tyr Thr Tyr Phe Asp Tyr Leu Ile Val
            130                 135                 140

Lys Pro Ala Asp Glu Ser Ile Val Glu Leu Lys Val Pro Lys Lys Leu
145                 150                 155                 160

Val Asn Pro Asn Ala Thr Lys Glu Ala Lys Ala Leu Met Ser Tyr Leu
                165                 170                 175

Val Asp Ile Tyr Gly Lys His Ile Leu Ser Gly Gln Gln Glu Ile Cys
            180                 185                 190

Gly Ser His Asn Tyr Pro Gly Ser Glu Ala Glu Phe Thr Tyr Ile Gln
            195                 200                 205

Glu Lys Thr Gly Lys Leu Pro Ala Ile Arg Gly Phe Asp Phe Met Asn
            210                 215                 220

Tyr Arg Gly Asn Gly Leu Met Trp Asp Asp Gln Cys Ala Glu Arg Val
225                 230                 235                 240

Ile Glu Trp Tyr Lys Glu Lys Gly Gly Ile Pro Thr Val Cys Trp His
                245                 250                 255

Trp Phe Ser Pro Gly Asp Ile Gly Lys Lys Ala Asp Asn Ser Phe Tyr
            260                 265                 270

Thr Glu Ser Thr Thr Phe Ser Ile Ser Arg Ala Leu Thr Pro Gly Thr
            275                 280                 285

Arg Lys Ile Leu His Cys Leu Thr Ile Ser Thr Pro Trp Pro Glu Ala
            290                 295                 300

Gln Ala Gly Ser Gly Cys Glu Phe Val Leu Phe Arg Pro Leu His Glu
305                 310                 315                 320

Ala Glu Gly Gly Trp Phe Trp Trp Gly Ala Glu Gly Pro Glu Pro Cys
                325                 330                 335

Val Arg Leu Tyr Arg Leu Leu Tyr Asp Lys Tyr Thr Asn Glu Tyr Gly
            340                 345                 350

Leu Asn Asn Leu Ile Trp Val Trp Thr Ser Tyr Asp Tyr Glu Thr Ser
            355                 360                 365

Ala Ala Trp Tyr Pro Gly Asp Asp Val Val Asp Ile Ile Gly Tyr Asp
            370                 375                 380

Lys Tyr Asn Ala Lys Asp Gly Lys Pro Asn Gly Ser Ala Ile Ser Ser
385                 390                 395                 400

Thr Phe Tyr Asn Leu Val Lys Leu Thr Asn Gly Lys Lys Leu Val Ala
                405                 410                 415

Met Thr Glu Asn Asp Thr Ile Pro Arg Val Ser Asn Leu Val Asn Glu
            420                 425                 430

Lys Ala Gly Trp Leu Tyr Phe Cys Pro Trp Tyr Gly Trp Trp Leu Thr
            435                 440                 445

Ser Glu Gln Asn Asn Pro Val Asp Trp Leu Val Glu Met Tyr Gln Ser
            450                 455                 460

Asp Tyr Cys Ile Thr Leu Asp Glu Leu Pro Asp Leu Gly Leu Asn Ala
465                 470                 475                 480

Thr Pro Thr Lys Gly Ala Thr Pro Thr Asn Thr Ala Thr Pro Thr Lys
                485                 490                 495

Ser Ala Thr Ala Thr Pro Thr Arg Pro Ser Val Pro Thr Asn Thr Pro
            500                 505                 510

Thr Asn Thr Pro Ala Asn Thr Pro Val Ser Gly Asn Leu Lys Val Glu
            515                 520                 525
```

```
Phe Tyr Asn Ser Asn Pro Ser Asp Thr Thr Asn Ser Ile Asn Pro Gln
        530                 535                 540

Phe Lys Val Thr Asn Thr Gly Ser Ser Ala Ile Asp Leu Ser Lys Leu
545                 550                 555                 560

Thr Leu Arg Tyr Tyr Thr Val Asp Gly Gln Lys Asp Gln Thr Phe
                565                 570                 575

Trp Cys Asp His Ala Ala Ile Ile Gly Ser Asn Gly Ser Tyr Asn Gly
                580                 585                 590

Ile Thr Ser Asn Val Lys Gly Thr Phe Val Lys Met Ser Ser Ser Thr
            595                 600                 605

Asn Asn Ala Asp Thr Tyr Leu Glu Ile Ser Phe Thr Gly Gly Thr Leu
        610                 615                 620

Glu Pro Gly Ala His Val Gln Ile Gln Gly Arg Phe Ala Lys Asn Asp
625                 630                 635                 640

Trp Ser Asn Tyr Thr Gln Ser Asn Asp Tyr Ser Phe Lys Ser Ala Ser
                645                 650                 655

Gln Phe Val Glu Trp Asp Gln Val Thr Ala Tyr Leu Asn Gly Val Leu
                660                 665                 670

Val Trp Gly Lys Glu Pro Gly
                675

<210> SEQ ID NO 8
<211> LENGTH: 726
<212> TYPE: PRT
<213> ORGANISM: Clostridium thermocellum

<400> SEQUENCE: 8

Met Gly His His His His His His Ala Ile Ala Met Ala Ala Leu Ile
1               5                   10                  15

Tyr Asp Asp Phe Glu Thr Gly Leu Asn Gly Trp Gly Pro Arg Gly Pro
            20                  25                  30

Glu Thr Val Glu Leu Thr Glu Glu Ala Tyr Ser Gly Arg Tyr Ser
        35                  40                  45

Leu Lys Val Ser Gly Arg Thr Ser Thr Trp Asn Gly Pro Met Val Asp
50                  55                  60

Lys Thr Asp Val Leu Thr Leu Gly Glu Ser Tyr Lys Leu Gly Val Tyr
65                  70                  75                  80

Val Lys Phe Val Gly Asp Ser Tyr Ser Asn Glu Gln Arg Phe Ser Leu
                85                  90                  95

Gln Leu Gln Tyr Asn Asp Gly Ala Gly Asp Val Tyr Gln Asn Ile Lys
            100                 105                 110

Thr Ala Thr Val Tyr Lys Gly Thr Trp Thr Leu Leu Glu Gly Gln Leu
        115                 120                 125

Thr Val Pro Ser His Ala Lys Asp Val Lys Ile Tyr Val Glu Thr Glu
    130                 135                 140

Phe Lys Asn Ser Pro Ser Pro Gln Asp Leu Met Asp Phe Tyr Ile Asp
145                 150                 155                 160

Asp Phe Thr Ala Thr Pro Ala Asn Leu Pro Glu Ile Glu Lys Asp Ile
                165                 170                 175

Pro Ser Leu Lys Asp Val Phe Ala Gly Tyr Phe Lys Val Gly Gly Ala
            180                 185                 190

Ala Thr Val Ala Glu Leu Ala Pro Lys Pro Ala Lys Glu Leu Phe Leu
        195                 200                 205

Lys His Tyr Asn Ser Leu Thr Phe Gly Asn Glu Leu Lys Pro Glu Ser
```

-continued

```
            210                 215                 220
Val Leu Asp Tyr Asp Ala Thr Ile Ala Tyr Met Glu Ala Asn Gly Gly
225                 230                 235                 240

Asp Gln Val Asn Pro Gln Ile Thr Leu Arg Ala Ala Arg Pro Leu Leu
                245                 250                 255

Glu Phe Ala Lys Glu His Asn Ile Pro Val Arg Gly His Thr Leu Val
            260                 265                 270

Trp His Ser Gln Thr Pro Asp Trp Phe Phe Arg Glu Asn Tyr Ser Gln
        275                 280                 285

Asp Glu Asn Ala Pro Trp Ala Ser Lys Glu Val Met Leu Gln Arg Leu
    290                 295                 300

Glu Asn Tyr Ile Lys Asn Leu Met Glu Ala Leu Ala Thr Glu Tyr Pro
305                 310                 315                 320

Thr Val Lys Phe Tyr Ala Trp Asp Val Val Asn Glu Ala Val Asp Pro
                325                 330                 335

Asn Thr Ser Asp Gly Met Arg Thr Pro Gly Ser Asn Asn Lys Asn Pro
            340                 345                 350

Gly Ser Ser Leu Trp Met Gln Thr Val Gly Arg Asp Phe Ile Val Lys
        355                 360                 365

Ala Phe Glu Tyr Ala Arg Lys Tyr Ala Pro Ala Asp Cys Lys Leu Phe
    370                 375                 380

Tyr Asn Asp Tyr Asn Glu Tyr Glu Asp Arg Lys Cys Asp Phe Ile Ile
385                 390                 395                 400

Glu Ile Leu Thr Glu Leu Lys Ala Lys Gly Leu Val Asp Gly Met Gly
                405                 410                 415

Met Gln Ser His Trp Val Met Asp Tyr Pro Ser Ile Ser Met Phe Glu
            420                 425                 430

Lys Ser Ile Arg Arg Tyr Ala Ala Leu Gly Leu Glu Ile Gln Leu Thr
        435                 440                 445

Glu Leu Asp Ile Arg Asn Pro Asp Asn Ser Gln Trp Ala Leu Glu Arg
    450                 455                 460

Gln Ala Asn Arg Tyr Lys Glu Leu Val Thr Lys Leu Val Asp Leu Lys
465                 470                 475                 480

Lys Glu Gly Ile Asn Ile Thr Ala Leu Val Phe Trp Gly Ile Thr Asp
                485                 490                 495

Ala Thr Ser Trp Leu Gly Gly Tyr Pro Leu Leu Phe Asp Ala Glu Tyr
            500                 505                 510

Lys Ala Lys Pro Ala Phe Tyr Ala Ile Val Asn Gly Leu Asn Ala Thr
        515                 520                 525

Pro Thr Lys Gly Ala Thr Pro Thr Asn Thr Ala Thr Pro Thr Lys Ser
    530                 535                 540

Ala Thr Ala Thr Pro Thr Arg Pro Ser Val Pro Thr Asn Thr Pro Thr
545                 550                 555                 560

Asn Thr Pro Ala Asn Thr Pro Val Ser Gly Asn Leu Lys Val Glu Phe
                565                 570                 575

Tyr Asn Ser Asn Pro Ser Asp Thr Thr Asn Ser Ile Asn Pro Gln Phe
            580                 585                 590

Lys Val Thr Asn Thr Gly Ser Ser Ala Ile Asp Leu Ser Lys Leu Thr
        595                 600                 605

Leu Arg Tyr Tyr Tyr Thr Val Asp Gly Gln Lys Asp Gln Thr Phe Trp
    610                 615                 620

Cys Asp His Ala Ala Ile Ile Gly Ser Asn Gly Ser Tyr Asn Gly Ile
625                 630                 635                 640
```

```
Thr Ser Asn Val Lys Gly Thr Phe Val Lys Met Ser Ser Thr Asn
            645                 650                 655

Asn Ala Asp Thr Tyr Leu Glu Ile Ser Phe Thr Gly Gly Thr Leu Glu
            660                 665                 670

Pro Gly Ala His Val Gln Ile Gln Gly Arg Phe Ala Lys Asn Asp Trp
            675                 680                 685

Ser Asn Tyr Thr Gln Ser Asn Asp Tyr Ser Phe Lys Ser Ala Ser Gln
            690                 695                 700

Phe Val Glu Trp Asp Gln Val Thr Ala Tyr Leu Asn Gly Val Leu Val
705                 710                 715                 720

Trp Gly Lys Glu Pro Gly
                725

<210> SEQ ID NO 9
<211> LENGTH: 902
<212> TYPE: PRT
<213> ORGANISM: Clostridium thermocellum

<400> SEQUENCE: 9

Met Gly His His His His His His Ala Ile Ala Met Tyr Glu Val Val
1               5                   10                  15

His Asp Thr Phe Glu Val Asn Phe Asp Gly Trp Cys Asn Leu Gly Val
            20                  25                  30

Asp Thr Tyr Leu Thr Ala Val Glu Asn Glu Gly Asn Asn Gly Thr Arg
            35                  40                  45

Gly Met Met Val Ile Asn Arg Ser Ser Ala Ser Asp Gly Ala Tyr Ser
        50                  55                  60

Glu Lys Gly Phe Tyr Leu Asp Gly Gly Val Glu Tyr Lys Tyr Ser Val
65                  70                  75                  80

Phe Val Lys His Asn Gly Thr Gly Thr Glu Thr Phe Lys Leu Ser Val
            85                  90                  95

Ser Tyr Leu Asp Ser Glu Thr Glu Glu Asn Lys Glu Val Ile Ala
            100                 105                 110

Thr Lys Asp Val Val Ala Gly Glu Trp Thr Glu Ile Ser Ala Lys Tyr
            115                 120                 125

Lys Ala Pro Lys Thr Ala Val Asn Ile Thr Leu Ser Ile Thr Thr Asp
        130                 135                 140

Ser Thr Val Asp Phe Ile Phe Asp Asp Val Thr Ile Thr Arg Lys Gly
145                 150                 155                 160

Met Ala Glu Ala Asn Thr Val Tyr Ala Ala Asn Ala Val Leu Lys Asp
            165                 170                 175

Met Tyr Ala Asn Tyr Phe Arg Val Gly Ser Val Leu Asn Ser Gly Thr
            180                 185                 190

Val Asn Asn Ser Ser Ile Lys Ala Leu Ile Leu Arg Glu Phe Asn Ser
        195                 200                 205

Ile Thr Cys Glu Asn Glu Met Lys Pro Asp Ala Thr Leu Val Gln Ser
        210                 215                 220

Gly Ser Thr Asn Thr Asn Ile Arg Val Ser Leu Asn Arg Ala Ala Ser
225                 230                 235                 240

Ile Leu Asn Phe Cys Ala Gln Asn Asn Ile Ala Val Arg Gly His Thr
            245                 250                 255

Leu Val Trp His Ser Gln Thr Pro Gln Trp Phe Phe Lys Asp Asn Phe
            260                 265                 270

Gln Asp Asn Gly Asn Trp Val Ser Gln Ser Val Met Asp Gln Arg Leu
```

```
            275                 280                 285
Glu Ser Tyr Ile Lys Asn Met Phe Ala Glu Ile Gln Arg Gln Tyr Pro
290                 295                 300
Ser Leu Asn Leu Tyr Ala Tyr Asp Val Val Asn Glu Ala Val Ser Asp
305                 310                 315                 320
Asp Ala Asn Arg Thr Arg Tyr Tyr Gly Gly Ala Arg Glu Pro Gly Tyr
                325                 330                 335
Gly Asn Gly Arg Ser Pro Trp Val Gln Ile Tyr Gly Asp Asn Lys Phe
                340                 345                 350
Ile Glu Lys Ala Phe Thr Tyr Ala Arg Lys Tyr Ala Pro Ala Asn Cys
                355                 360                 365
Lys Leu Tyr Tyr Asn Asp Tyr Asn Glu Tyr Trp Asp His Lys Arg Asp
370                 375                 380
Cys Ile Ala Ser Ile Cys Ala Asn Leu Tyr Asn Lys Gly Leu Leu Asp
385                 390                 395                 400
Gly Val Gly Met Gln Ser His Ile Asn Ala Asp Met Asn Gly Phe Ser
                405                 410                 415
Gly Ile Gln Asn Tyr Lys Ala Ala Leu Gln Lys Tyr Ile Asn Ile Gly
                420                 425                 430
Cys Asp Val Gln Ile Thr Glu Leu Asp Ile Ser Thr Glu Asn Gly Lys
                435                 440                 445
Phe Ser Leu Gln Gln Ala Asp Lys Tyr Lys Ala Val Phe Gln Ala
450                 455                 460
Ala Val Asp Ile Asn Arg Thr Ser Ser Lys Gly Lys Val Thr Ala Val
465                 470                 475                 480
Cys Val Trp Gly Pro Asn Asp Ala Asn Thr Trp Leu Gly Ser Gln Asn
                485                 490                 495
Ala Pro Leu Leu Phe Asn Ala Asn Asn Gln Pro Lys Pro Ala Tyr Asn
                500                 505                 510
Ala Val Ala Ser Ile Ile Pro Gln Ser Glu Trp Gly Asp Gly Asn Asn
                515                 520                 525
Pro Ala Gly Gly Gly Gly Gly Lys Pro Glu Glu Pro Asp Ala Asn
530                 535                 540
Gly Tyr Tyr Tyr His Asp Thr Phe Glu Gly Ser Val Gly Gln Trp Thr
545                 550                 555                 560
Ala Arg Gly Pro Ala Glu Val Leu Leu Ser Gly Arg Thr Ala Tyr Lys
                565                 570                 575
Gly Ser Glu Ser Leu Leu Val Arg Asn Arg Thr Ala Ala Trp Asn Gly
                580                 585                 590
Ala Gln Arg Ala Leu Asn Pro Arg Thr Phe Val Pro Gly Asn Thr Tyr
                595                 600                 605
Cys Phe Ser Val Val Ala Ser Phe Ile Glu Gly Ala Ser Ser Thr Thr
610                 615                 620
Phe Cys Met Lys Leu Gln Tyr Val Asp Gly Ser Gly Thr Gln Arg Tyr
625                 630                 635                 640
Asp Thr Ile Asp Met Lys Thr Val Gly Pro Asn Gln Trp Val His Leu
                645                 650                 655
Tyr Asn Pro Gln Tyr Arg Ile Pro Ser Asp Ala Thr Asp Met Tyr Val
                660                 665                 670
Tyr Val Glu Thr Ala Asp Asp Thr Ile Asn Phe Tyr Ile Asp Glu Ala
                675                 680                 685
Ile Gly Ala Val Ala Gly Thr Val Ile Glu Gly Gly Leu Asn Ala Thr
690                 695                 700
```

-continued

```
Pro Thr Lys Gly Ala Thr Pro Thr Asn Thr Ala Thr Pro Lys Ser
705                 710                 715                 720

Ala Thr Ala Thr Pro Thr Arg Pro Ser Val Pro Thr Asn Thr Pro Thr
                725                 730                 735

Asn Thr Pro Ala Asn Thr Pro Val Ser Gly Asn Leu Lys Val Glu Phe
            740                 745                 750

Tyr Asn Ser Asn Pro Ser Asp Thr Thr Asn Ser Ile Asn Pro Gln Phe
        755                 760                 765

Lys Val Thr Asn Thr Gly Ser Ser Ala Ile Asp Leu Ser Lys Leu Thr
        770                 775                 780

Leu Arg Tyr Tyr Tyr Thr Val Asp Gly Gln Lys Asp Gln Thr Phe Trp
785                 790                 795                 800

Cys Asp His Ala Ala Ile Ile Gly Ser Asn Gly Ser Tyr Asn Gly Ile
                805                 810                 815

Thr Ser Asn Val Lys Gly Thr Phe Val Lys Met Ser Ser Ser Thr Asn
            820                 825                 830

Asn Ala Asp Thr Tyr Leu Glu Ile Ser Phe Thr Gly Gly Thr Leu Glu
        835                 840                 845

Pro Gly Ala His Val Gln Ile Gln Gly Arg Phe Ala Lys Asn Asp Trp
        850                 855                 860

Ser Asn Tyr Thr Gln Ser Asn Asp Tyr Ser Phe Lys Ser Ala Ser Gln
865                 870                 875                 880

Phe Val Glu Trp Asp Gln Val Thr Ala Tyr Leu Asn Gly Val Leu Val
                885                 890                 895

Trp Gly Lys Glu Pro Gly
            900
```